United States Patent
Brown et al.

(10) Patent No.: US 7,960,567 B2
(45) Date of Patent: Jun. 14, 2011

(54) COMPOUNDS AND METHODS USEFUL FOR TREATING ASTHMA AND ALLERGIC INFLAMMATION

(75) Inventors: Matthew Brown, San Francisco, CA (US); Michael G. Johnson, San Francisco, CA (US); An-Rong Li, San Mateo, CA (US); Jiwen Liu, Foster City, CA (US); Sarah E. Lively, San Carlos, CA (US); Julio C. Medina, San Carlos, CA (US); Wang Shen, San Mateo, CA (US); Xuemei Wang, Thousand Oaks, CA (US); Yingcai Wang, Fremont, CA (US)

(73) Assignee: Amgen Inc., Thousand Oaks, CA (US)

( * ) Notice: Subject to any disclaimer, the term of this patent is extended or adjusted under 35 U.S.C. 154(b) by 339 days.

(21) Appl. No.: 12/113,121

(22) Filed: Apr. 30, 2008

(65) Prior Publication Data

US 2008/0312270 A1 Dec. 18, 2008

Related U.S. Application Data

(60) Provisional application No. 60/927,545, filed on May 2, 2007.

(51) Int. Cl.
*C07D 209/08* (2006.01)
*C07D 209/12* (2006.01)
*C07D 209/30* (2006.01)
*C07D 209/42* (2006.01)
*C07D 209/48* (2006.01)
*A61K 31/404* (2006.01)
*A61K 31/4035* (2006.01)

(52) U.S. Cl. ........ 548/469; 548/473; 548/490; 514/415; 514/417

(58) Field of Classification Search ............... 548/469, 548/473, 490; 514/415, 417
See application file for complete search history.

(56) References Cited

U.S. PATENT DOCUMENTS

| 5,545,669 | A | 8/1996 | Adams et al. |
| 5,849,780 | A | 12/1998 | Di Malta et al. |
| 5,929,250 | A | 7/1999 | Widdowson et al. |
| 7,321,001 | B2 | 1/2008 | Fu et al. |
| 7,709,521 | B2 * | 5/2010 | Bonnert et al. ............... 514/419 |
| 2008/0085891 | A1 | 4/2008 | Fu et al. |

FOREIGN PATENT DOCUMENTS

| WO | WO 95/33461 | 12/1995 |
| WO | WO 0051971 A1 * | 9/2000 |
| WO | WO 01/57020 A1 | 8/2001 |
| WO | WO 02051805 A1 * | 7/2002 |
| WO | WO 2004/037788 A1 | 5/2004 |
| WO | WO 2004/058164 A2 | 7/2004 |
| WO | WO 2005/054176 A1 | 6/2005 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
West, Anthony R., "Solid State Chemistry and its Applications", Wiley, New York, 1988, pp. 358 & 365.*
Armer et. al. "Indole-3-acetic Acid Antagonists of the Prostaglandin D2 Receptor CRTH2" Journal of Medicinal Chemistry 2005, 48, 6174-6177.*
Sturino et. al. "Discovery of a Potent and Selective Prostaglandin D2 Receptor Antagonist, [(3R)-4-(4-Chlorobenzyl)-7-fluoro-5-(methylsulfonyl)-1,2,3,4-tetrahydrocyclopenta[b]indol-3-yl]-acetic Acid (MK-0524)†" Journal of Medicinal Chemistry 2007, 50, 794-806.*
PCT International Search Report dated Nov. 20, 2008; for International Application No. PCT/US2008/005611, filed May 1, 2008.

* cited by examiner

*Primary Examiner* — Janet Andres
*Assistant Examiner* — David K O Dell
(74) *Attorney, Agent, or Firm* — Bernard P. Friedrichsen

(57) ABSTRACT

Compounds, compositions and methods that are useful in the treatment of inflammatory and immune-related diseases and conditions are provided herein. In particular, the invention provides compounds which modulate the function and/or expression of proteins involved in atopic diseases, inflammatory conditions and cancer. The subject compounds are carboxylic acid derivatives.

19 Claims, 1 Drawing Sheet

Scheme A

COMPOUNDS AND METHODS USEFUL FOR TREATING ASTHMA AND ALLERGIC INFLAMMATION

1. RELATED APPLICATIONS

Figure 1:
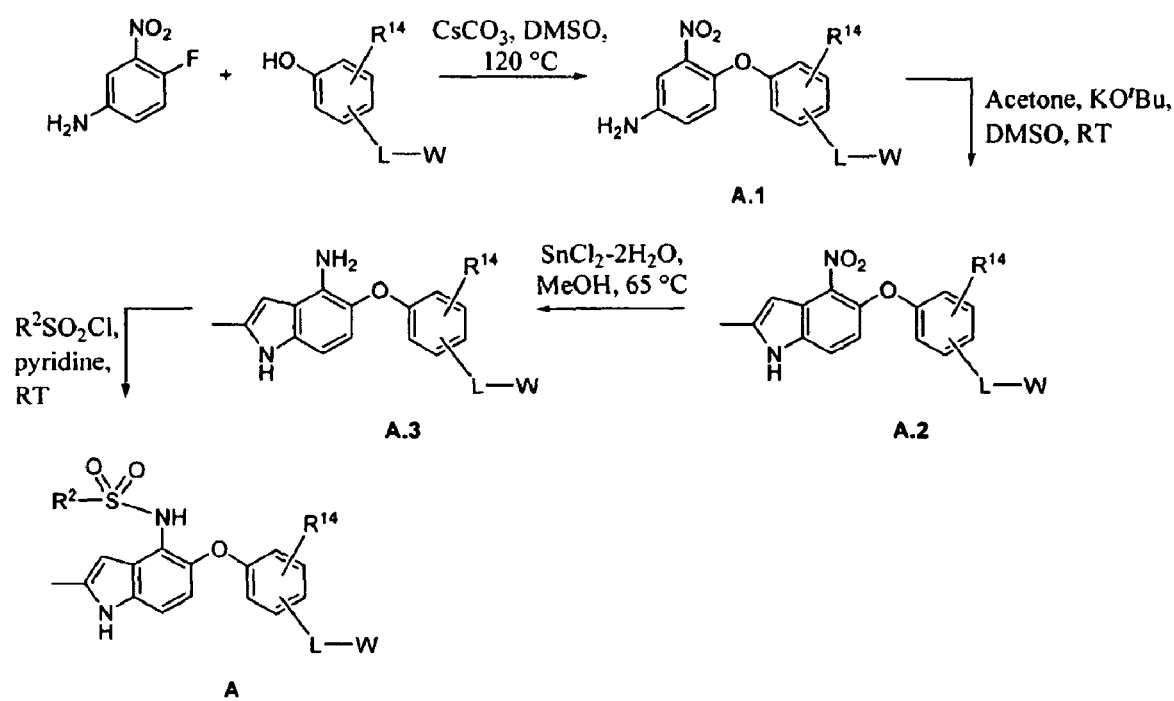

This application claims the benefit of U.S. Provisional Application No. 60/927,545 filed May 2, 2007, which is incorporated by reference herein in its entirety for all purposes.

2. FIELD OF THE INVENTION

The present invention is directed to compounds, compositions and methods useful for treating inflammatory and immune-related diseases and conditions. The compounds are modulators of prostaglandin $D_2$ ($PGD_2$) receptors including CRTH2 and DP receptors.

3. BACKGROUND OF THE INVENTION

G-protein coupled receptors play important roles in diverse signaling processes, including those involved in host defense mechanisms. Immune responses to infectious diseases, injury, tumors and organ transplantation and in diseases and conditions such as asthma, allergy, rheumatoid arthritis and neoplasia have been linked to GPCR regulation. Exaggerated or misdirected immune responses are responsible for many inflammatory and hypersensitivity diseases which, left untreated, can result in tissue or organ damage, pain and/or loss of function. Tissue inflammation is largely implicated in the pathogenesis of such diseases, of which asthma and allergic diseases are among the most well characterized. The mechanisms underlying airway inflammation and hyperreactivity are similar to those underlying allergic inflammation in other tissues, such as the skin and gut.

Prostaglandins are lipid-derived inflammatory mediators that recruit macrophages, T cells, eosinophils, basophils and neutrophils from peripheral blood to damaged or inflamed tissues. In addition, prostaglandins can, depending on the target cell type, induce or inhibit intracellular $Ca^{2+}$ mobilization, cAMP production, platelet aggregation, leukocyte aggregation, T cell proliferation, lymphocyte migration, Th2 cell chemotaxis, IL-1a and IL-2 secretion and vascular and non-vascular smooth muscle contraction in responsive cells. Prostaglandins have been implicated in fever, various allergic diseases, vascular and non-vascular smooth muscle relaxation, pain perception, sleep, platelet aggregation and reproductive processes. Prostaglandins exert their effects by interacting with specific GPCRs.

Prostaglandin $D_2$ ($PGD_2$) is the major inflammatory mediator released by activated mast cells, typically found near skin surfaces, mucous membranes and blood vessels, upon immunological challenge (Lewis et al. (1982) *J. Immunol.* 129:1627-1631). During asthma and allergic responses, $PGD_2$ is released in large amounts. The role of $PGD_2$ in the initiation and maintenance of allergic inflammation has been well established in mouse models of asthma. For example, it has been demonstrated that overproduction of $PGD_2$ in vivo by $PGD_2$ synthase exacerbates airway inflammation in a mouse model of asthma (Fujitani et al. (2002) *J. Immunol.* 168:443-449).

A $PGD_2$-selective receptor, designated DP, has been identified (Boie et al. (1995) *J. Biol. Chem.* 270:18910-18916). In humans, DP is expressed in smooth muscle, platelets, small intestine and brain, and its expression in lung epithelium is induced by allergic challenge. Receptor activation induces cAMP production and intracellular $Ca^{2+}$ mobilization, and is believed to inhibit platelet aggregation and cell migration and induce relaxation of various smooth muscles. DP is coupled primarily to Gαs protein.

Significantly, in an OVA induced asthma model, $DP^{-/-}$ mice exhibited reduced asthma symptoms, e.g., reduced cellular infiltration of eosinophils and lymphocytes in BAL fluid, reduced Th2 cytokine levels in BAL fluid and reduced airway hyperreactivity to acetylcholine (Matsuoka et al. (2002) *Science* 287:2013-2019). The increased cellular infiltration in lung tissue and mucus secretion by airway epithelial cells, characteristic of asthma in humans and observed in wild-type mice, was not observed in DP-deficient mice.

Recently, an additional $PGD_2$-selective receptor, designated chemoattractant receptor-homologous molecule expressed on Th2 cells, or CRTH2, has been identified (Hirai et al. (2001) *J. Exp. Med.* 193(2):255-261). The receptor was previously referred to as GPR44 or DL1R. Among peripheral blood T lymphocytes, human CRTH2 is selectively expressed on Th2 cells, and is highly expressed on cell types associated with allergic inflammation such as eosinophils, basophils and Th2 cells. It has been shown that CRTH2 activation induces intracellular $Ca^{2+}$ mobilization and infiltration of Th2 cells, eosinophils and basophils.

Protein sequence analysis indicates that CRTH2 has no significant homology to DP, but rather, is related to members of the N-formyl peptide receptor (FPR) subfamily (Nagata et al. (1999) *J. Immunol.* 162:1278-1286). In contrast to DP, CRTH2 has been shown to couple primarily to Gαi protein.

These observations suggest that CRTH2 and DP may function independently to regulate aspects of allergic inflammation.

The increasing incidence of asthma, allergic diseases and immunologic diseases worldwide underscores the need for new therapies to effectively treat or prevent these diseases. The discovery of small molecules that modulate CRTH2 and/or one or more other $PGD_2$ receptors, e.g., DP, is useful for the study of physiological processes mediated by CRTH2 and/or one or more other $PGD_2$ receptors, e.g., DP, and the development of therapeutic agents for asthma, allergic diseases and other immunologic diseases. Novel compounds which display such desirable activity are described herein.

4. SUMMARY OF THE INVENTION

The invention provides compounds, pharmaceutical compositions and methods useful for treating or preventing conditions and disorders associated with inflammation processes. In particular, the invention provides compounds, pharmaceutical compositions and methods useful for treating or preventing asthma, allergic diseases, inflammatory conditions, cancer and viral infection.

In one aspect, the invention provides compounds of formula I:

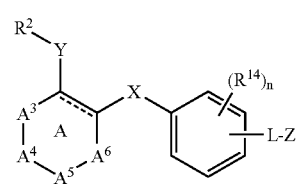

wherein

A is 6-membered ring in which $A^3$ is —C($R^3$)=, —N($R^3$)—, or —N=;

$A^4$ is —C($R^4$)=, —N($R^4$)—, or —N=;

$A^5$ is —C($R^5$)=, —N($R^5$)—, or —N=;

$A^6$ is —C($R^6$)=, —N($R^6$)—, or —N=;

provided that at least one pair of $R^3$ and $R^4$, $R^4$ and $R^5$ or $R^5$ and $R^6$ form a 5- or 6-membered ring fused with A;

X represents a divalent linkage selected from —O—, —S(O)$_k$—, —$CR^aR^b$—, —C(O)—, —$NR^8$— and C($NR^9$)—;

Y represents a divalent linkage selected from a single bond, —S(O)$_k NR^{10}$—, —C(O)$NR^{10}$—, ($C_1$-$C_4$)alkylene, hetero($C_2$-$C_4$)alkylene, —N($R^{11}$)C(O)$NR^{10}$—, —N($R^{11}$)S(O)$_k NR^{10}$—, —N($R^{11}$)$CO_2$—, —$NR^{11}$—, —O— and —S(O)$_k$—;

Z represents —$CO_2 R^{12}$, —C(O)$NR^{12} R^{13}$ or heteroaryl;

L represents a divalent linkage selected from a single bond, ($C_1$-$C_6$)alkylene, ($C_2$-$C_6$)alkenylene, ($C_2$-$C_6$)alkynylene and ($C_2$-$C_4$)heteroalkylene;

$R^2$ is hydrogen, ($C_1$-$C_8$)alkyl, cyclo($C_3$-$C_8$)alkyl, cyclo($C_3$-$C_8$)alkenyl, hetero($C_2$-$C_8$)alkyl, heterocyclo($C_3$-$C_8$)alkyl, heterocyclo($C_3$-$C_8$)alkenyl, aryl, heteroaryl or aryl($C_1$-$C_4$)alkyl;

$R^3$, $R^4$, $R^5$ and $R^6$ are independently hydrogen, halogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —NR'R", —OR', —$NO_2$, —CN, —C(O)R', —$CO_2$R', —C(O)NR'R", ($C_1$-$C_4$)alkylene-C(O)NR'R", —S(O)$_m$R', —S(O)$_k$NR'R", —OC(O)OR', —OC(O)R', —OC(O)NR'R", —N(R''')C(O)NR'R", —N(R")C(O)R', —N(R")S(O)$_k$R' or —N(R")C(O)OR', provided that at least one pair of adjacent substituents of $R^3$ and $R^4$, $R^4$ and $R^5$, or $R^5$ and $R^6$ form a 5- or 6-membered ring containing 0, 1, 2 or 3 heteroatoms selected from N, O and S that is fused with ring A; optionally the fused 5- or 6-membered ring is substituted with halogen, ($C_1$-$C_3$)alkyl, halo($C_1$-$C_3$)alkyl, cyclo($C_3$-$C_5$)alkyl, cyclo($C_3$-$C_5$)alkenyl, amino($C_1$-$C_3$)alkyl, hydroxy, oxo, —OR', —CONR'R", —N(R")C(O)R', —$CO_2$R', —CN, aryl, or heteroaryl;

$R^8$, $R^{10}$ and $R^{11}$ are independently hydrogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —C(O)R', —$CO_2$R', —C(O)NR'R", —S(O)$_m$R' or —S(O)$_k$NR'R";

$R^9$ is hydrogen, ($C_1$-$C_6$)alkyl, hetero($C_2$-$C_6$)alkyl, aryl($C_1$-$C_4$)alkyl, —OR' or —NR'R";

$R^{12}$ and $R^{13}$ are independently hydrogen, ($C_1$-$C_6$)alkyl, hetero($C_2$-$C_6$)alkyl, aryl, aryl($C_1$-$C_4$)alkyl or heteroaryl;

each $R^{14}$ is independently halogen, ($C_1$-$C_8$)alkyl, fluoro($C_1$-$C_4$)alkyl, ($C_2$-$C_5$)alkenyl, —OR', —NR'R", —$NO_2$, —CN, —C(O)R' or aryl; optionally, a $R^{14}$ group and L taken together form a 5-, 6-, 7- or 8-membered fused ring containing from 0 to 3 heteroatoms selected from N, O and S;

$R^a$ and $R^b$ are independently hydrogen, ($C_1$-$C_6$)alkyl, hetero($C_2$-$C_6$)alkyl, aryl($C_1$-$C_4$)alkyl, —OR' or —NR'R";

each R', R" and R''' is independently hydrogen, ($C_1$-$C_6$)alkyl, cyclo($C_3$-$C_8$)alkyl, cyclo($C_3$-$C_8$)alkenyl, aryl or aryl($C_1$-$C_4$)alkyl;

each subscript k is 0, 1 or 2;

each subscript m is 0, 1, 2 or 3; and the subscript n is 0, 1, 2, 3 or 4.

In some embodiments, the compounds of the invention have formula II:

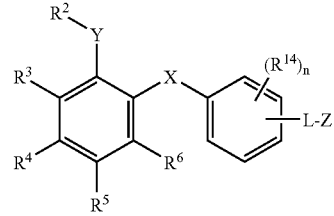

wherein

X, Y, Z, L, and $R^2$ are as defined above with regard to formula I;

$R^3$, $R^4$, $R^5$ and $R^6$ are independently hydrogen, halogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —NR'R", —OR', —$NO_2$, —CN, —C(O)R', —$CO_2$R', —C(O)NR'R", ($C_1$-$C_4$)alkylene-C(O)NR'R", —S(O)$_m$R', —S(O)$_k$NR'R", —OC(O)OR', OC(O)R', —OC(O)NR'R", —N(R''')C(O)NR'R", —N(R")C(O)R', —N(R")S(O)$_k$R' or —N(R")C(O)OR', provided that at least one pair of adjacent substituents of $R^3$ and $R^4$, $R^4$ and $R^5$, or $R^5$ and $R^6$ form a fused 5- or 6-membered ring containing 0, 1, 2 or 3 heteroatoms selected from N, O and S; optionally, the fused 5- or 6-membered ring is substituted with halogen, ($C_1$-$C_3$)alkyl, halo($C_1$-$C_3$)alkyl, cyclo($C_3$-$C_5$)alkyl, cyclo($C_3$-$C_5$)alkenyl, amino($C_1$-$C_3$)alkyl, hydroxy, oxo, —OR', —CONR'R", —N(R")C(O)R', —$CO_2$R', —CN, aryl, or heteroaryl;

each $R^{14}$ is independently halogen, ($C_1$-$C_8$)alkyl, fluoro($C_1$-$C_4$)alkyl, ($C_2$-$C_5$)alkenyl, —OR', —NR'R", —$NO_2$, —CN, —C(O)R' or aryl; optionally, a $R^{14}$ group and L taken together form a 5-, 6-, 7- or 8-membered fused ring containing from 0 to 3 heteroatoms selected from N, O and S;

each R', R" and R''' is independently hydrogen, ($C_1$-$C_6$) alkyl, cyclo($C_3$-$C_8$)alkyl, cyclo($C_3$-$C_8$)alkenyl, aryl or aryl ($C_1$-$C_4$)alkyl;

each subscript k is 0, 1 or 2;

each subscript m is 0, 1, 2 or 3; and the subscript n is 0, 1, 2, 3 or 4.

In certain embodiments, the invention provides compounds of formula VI, XI, XV, XXI, XXV, XXX, XXXIV, XXXX or XXXXIV:

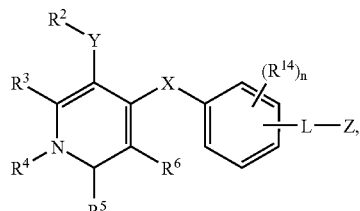

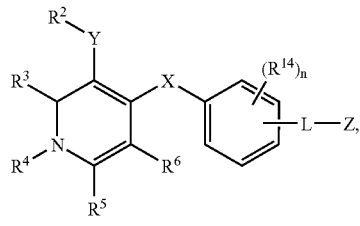

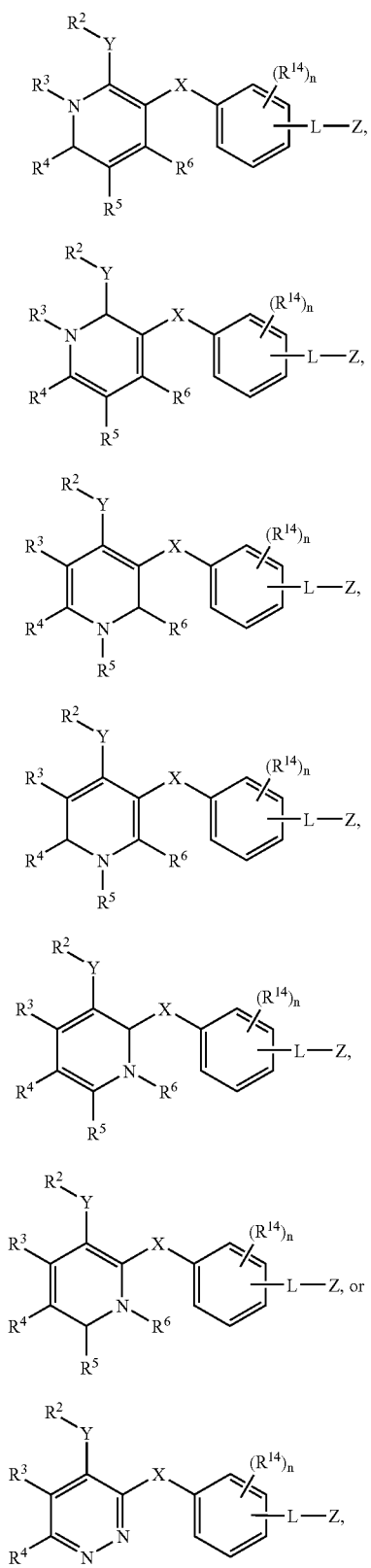

wherein X, Y, Z, L, $R^2$, $R^3$, $R^4$, $R^5$, $R^6$, $R^{14}$ and subscript n have the meanings and groupings provided above in formula II.

In certain embodiments, the invention provides compounds of formula X, XIX, XX, XXIX, XXXVIII, or XXXIX:

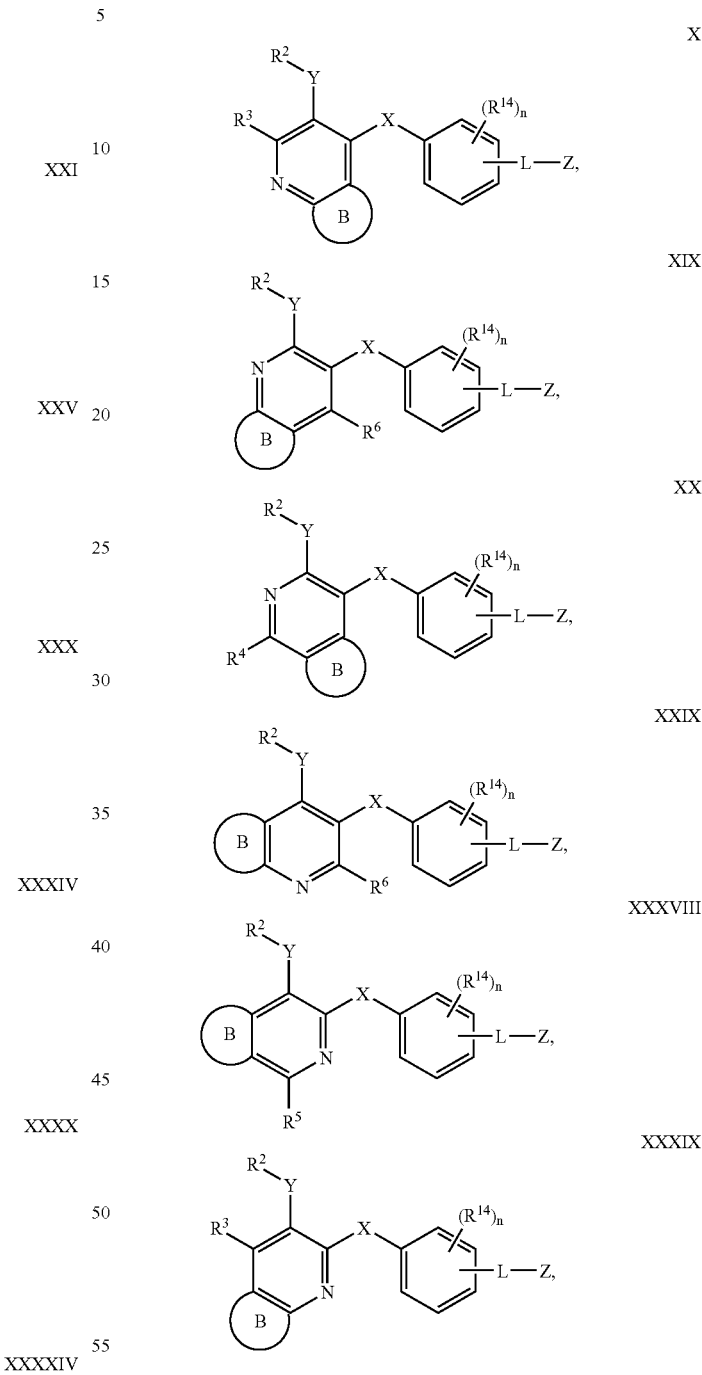

wherein X, Y, Z, L, $R^2$, $R^3$, $R^4$, $R^5$, $R^6$, $R^{14}$ and subscript n have the meanings and groupings provided above in formula II, and structure B represents a fused 5- or 6-membered ring containing 0, 1, 2 or 3 heteroatoms selected from N, O and S; optionally, structure B is substituted with halogen, $(C_1\text{-}C_3)$ alkyl, halo$(C_1\text{-}C_3)$alkyl, cyclo$(C_3\text{-}C_5)$alkyl, cyclo$(C_3\text{-}C_8)$ alkenyl, amino$(C_1\text{-}C_3)$alkyl, hydroxy, oxo, —OR', —CONR'R", —N(R")C(O)R', —$CO_2$R', —CN, aryl, or heteroaryl, wherein R' and R" are each independently hydrogen, $(C_1\text{-}C_6)$alkyl, cyclo$(C_3\text{-}C_8)$alkyl, cyclo$(C_3\text{-}C_8)$alkenyl, aryl or aryl$(C_1\text{-}C_4)$alkyl.

Unless otherwise indicated, the compounds provided in the formulas described herein are meant to include pharmaceutically acceptable salts, solvates and prodrugs thereof.

The invention also provides pharmaceutical compositions comprising a compound of formula I and a pharmaceutically acceptable carrier, excipient or diluent.

The invention also provides methods for treating or preventing inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion and urticaria, comprising administering to a subject in need thereof a therapeutically effective amount of a compound of formula I.

The invention also provides methods for treating or preventing a condition or disorder mediated, regulated or influenced by Th2 cells, eosinophils, basophils, platelets, Langerhans cells, dendritic cells or mast cells, comprising administering to a subject in need thereof a therapeutically effective amount of a compound of formula I.

The invention also provides methods for treating or preventing a condition or disorder mediated, regulated or influenced by $PGD_2$ and metabolites thereof, such as 13,14-dihydro-15-keto-$PGD_2$ and 15-deoxy-$\Delta^{12,14}$-$PGD_2$, comprising administering to a subject in need thereof a therapeutically effective amount of a compound of formula I.

The invention further provides methods for treating or preventing a condition or disorder responsive to modulation of CRTH2 and/or one or more other $PGD_2$ receptors, e.g., DP, comprising administering to a subject in need thereof a therapeutically effective amount of a compound of formula I.

The invention also provides methods for treating or preventing a condition or disorder mediated by CRTH2 and/or one or more other $PGD_2$ receptors, e.g., DP, comprising administering to a subject in need thereof a therapeutically effective amount of a compound of formula I.

The invention also provides methods for modulating CRTH2 and/or one or more other $PGD_2$ receptors, e.g., DP, comprising contacting a cell with a compound of formula I.

Other objects, features and advantages of the invention will become apparent to those skilled in the art from the following description and claims.

5. BRIEF DESCRIPTION OF THE FIGURES

FIG. 1 illustrates a general synthesis scheme for exemplary compounds of the invention.

6. DETAILED DESCRIPTION

6.1. Definitions

The abbreviations used herein are conventional, unless otherwise defined.

As used herein, the term "condition or disorder responsive to another $PGD_2$ receptor" and related terms and phrases refer to a condition or disorder associated with inappropriate, e.g., less than or greater than normal, activity of another $PGD_2$ receptor and at least partially responsive to or affected by modulation of another $PGD_2$ receptor (e.g., another $PGD_2$ receptor antagonist or agonist results in some improvement in patient well-being in at least some patients). Inappropriate functional activity of another $PGD_2$ receptor might arise as the result of expression of another $PGD_2$ receptor in cells which normally do not express the receptor, increased expression of another $PGD_2$ receptor or degree of intracellular activation (leading to, e.g., inflammatory and immune-related disorders and diseases) or decreased expression of another $PGD_2$ receptor. A condition or disorder associated with another $PGD_2$ receptor may include a condition or disorder mediated by another $PGD_2$ receptor.

As used herein, the phrase "condition or disorder mediated by another $PGD_2$ receptor" and related phrases and terms refer to a condition or disorder characterized by inappropriate, e.g., less than or greater than normal, activity of another $PGD_2$ receptor. Inappropriate functional activity of another $PGD_2$ receptor might arise as the result of expression of another $PGD_2$ receptor in cells which normally do not express the receptor, increased expression of another $PGD_2$ receptor or degree of intracellular activation (leading to, e.g., inflammatory and immune-related disorders and diseases) or decreased expression of another $PGD_2$ receptor. A condition or disorder mediated by another $PGD_2$ receptor may be completely or partially mediated by inappropriate functional activity of another $PGD_2$ receptor. However, a condition or disorder mediated by of another $PGD_2$ receptor is one in which modulation of another $PGD_2$ receptor results in some effect on the underlying condition or disorder (e.g., another $PGD_2$ receptor antagonist or agonist results in some improvement in patient well-being in at least some patients).

As used herein, the term "CRTH2" refers to a CRTH2 protein (RefSeq Accession No. NP_007469) or variant thereof that is capable of mediating a cellular response to $PGD_2$ in vitro or in vivo. CRTH2 variants include proteins substantially homologous to native CRTH2, i.e., proteins having one or more naturally or non-naturally occurring amino acid deletions, insertions or substitutions (e.g., CRTH2 derivatives, homologs and fragments). The amino acid sequence of CRTH2 variant preferably is at least about 80% identical to a native CRTH2, more preferably at least about 90% identical, and most preferably at least about 95% identical.

As used herein, the phrases "CRTH2-mediated condition or disorder," "a condition or disorder mediated by CRTH2" and related phrases and terms refer to a condition or disorder characterized by inappropriate, e.g., less than or greater than normal, CRTH2 activity. Inappropriate CRTH2 functional activity might arise as the result of CRTH2 expression in cells which normally do not express CRTH2, increased CRTH2 expression or degree of intracellular activation (leading to, e.g., inflammatory and immune-related disorders and diseases) or decreased CRTH2 expression. A CRTH2-mediated condition or disorder may be completely or partially mediated by inappropriate CRTH2 functional activity. However, a CRTH2-mediated condition or disorder is one in which modulation of CRTH2 results in some effect on the underlying condition or disorder (e.g., an CRTH2 antagonist or agonist results in some improvement in patient well-being in at least some patients).

The term "CRTH2-modulating amount" refers to that amount of a compound that is needed to produce a desired effect in any one of the cell-based assays, biochemical assays or animal models described herein or otherwise known to the skilled artisan. Typically, a CRTH2-modulating amount of a compound will be at least that amount which exhibits an $EC_{50}$ in a reporter-gene cell-based assay (relative to an untreated control).

As used herein, the terms "CRTH2-responsive condition or disorder," "condition or disorder responsive to CRTH2" and related terms and phrases refer to a condition or disorder associated with inappropriate, e.g., less than or greater than normal, CRTH2 activity and at least partially responsive to or affected by CRTH2 modulation (e.g., a CRTH2 antagonist or agonist results in some improvement in patient well-being in at least some patients). Inappropriate CRTH2 functional activity might arise as the result of CRTH2 expression in cells which normally do not express CRTH2, increased CRTH2 expression or degree of intracellular activation (leading to, e.g., inflammatory and immune-related disorders and diseases) or decreased CRTH2 expression. A CRTH2-associated condition or disorder may include a CRTH2-mediated condition or disorder.

As used herein, the term "DP" refers to a DP protein (RefSeq Accession No. NP_000944) or variant thereof that is capable of mediating a cellular response to $PGD_2$ in vitro or in vivo. DP variants include proteins substantially homologous to native DP, i.e., proteins having one or more naturally or non-naturally occurring amino acid deletions, insertions or substitutions (e.g., DP derivatives, homologs and fragments). The amino acid sequence of DP variant preferably is at least about 80% identical to a native DP, more preferably at least about 90% identical, and most preferably at least about 95% identical.

The term "DP-modulating amount" refers to that amount of a compound that is needed to produce a desired effect in any one of the cell-based assays, biochemical assays or animal models described herein or otherwise known to the skilled artisan. Typically, a DP-modulating amount of a compound will be at least that amount which exhibits an $EC_{50}$ in a reporter-gene cell-based assay (relative to an untreated control).

As used herein, the terms "DP-responsive condition or disorder," "condition or disorder responsive to DP" and related terms and phrases refer to a condition or disorder associated with inappropriate, e.g., less than or greater than normal, DP activity and at least partially responsive to or affected by DP modulation (e.g., a DP antagonist or agonist results in some improvement in patient well-being in at least some patients). Inappropriate DP functional activity might arise as the result of DP expression in cells which normally do not express DP, increased DP expression or degree of intracellular activation (leading to, e.g., inflammatory and immune-related disorders and diseases) or decreased DP expression. A DP-associated condition or disorder may include a DP-mediated condition or disorder.

As used herein, the phrases "DP-mediated condition or disorder," "a condition or disorder mediated by DP" and related phrases and terms refer to a condition or disorder characterized by inappropriate, e.g., less than or greater than normal, DP activity. Inappropriate DP functional activity might arise as the result of DP expression in cells which normally do not express DP, increased DP expression or degree of intracellular activation (leading to, e.g., inflammatory and immune-related disorders and diseases) or decreased DP expression. A DP-mediated condition or disorder may be completely or partially mediated by inappropriate DP functional activity. However, a DP-mediated condition or disorder is one in which modulation of DP results in some effect on the underlying condition or disorder (e.g., an DP antagonist or agonist results in some improvement in patient well-being in at least some patients).

The terms "modulate", "modulation" and the like refer to the ability of a compound to increase or decrease the function and/or expression of CRTH2 and/or one or more other $PGD_2$ receptors, e.g., DP, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with CRTH2 and/or one or more other $PGD_2$ receptors, either directly or indirectly, and/or the upregulation or downregulation of the expression of CRTH2 and/or one or more other $PGD_2$ receptors, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of CRTH2 and/or one or more other $PGD_2$ receptors can be demonstrated in a biochemical assay, e.g., binding assay, or a cell-based assay, e.g., a transient transfection assay.

As used herein, the terms "other $PGD_2$ receptor", "another $PGD_2$ receptor" and the like refer to a prostanoid receptor protein other than CRTH2, or variant thereof, that is capable of mediating a cellular response to $PGD_2$ in vitro or in vivo. Another $PGD_2$ receptor may be selective for $PGD_2$, e.g., DP (RefSeq Accession No. NP_000944), or other one or more other prostanoids (e.g., $EP_1$, $EP_2$, $EP_3$ and $EP_4$, FP, IP and TP). Other $PGD_2$ receptor variants include proteins substantially homologous to a corresponding native prostanoid receptor other than CRTH2, i.e., proteins having one or more naturally or non-naturally occurring amino acid deletions, insertions or substitutions (e.g., derivatives, homologs and fragments of another $PGD_2$ receptor). The amino acid sequence of other $PGD_2$ receptor variants preferably is at least about 80% identical to the corresponding native other $PGD_2$ receptors, more preferably at least about 90% identical, and most preferably at least about 95% identical. Preferably, another $PGD_2$ receptor is DP.

The term "$PGD_2$ receptor-modulating amount" and related terms and phrases refer to that amount of a compound that is needed to produce a desired effect in any one of the cell-based assays, biochemical assays or animal models described herein or otherwise known to the skilled artisan. Typically, a $PGD_2$ receptor-modulating amount of a compound will be at least that amount which exhibits an $EC_{50}$ in a reporter-gene cell-based assay (relative to an untreated control).

The terms "prevent", "preventing" and "prevention", as used herein, refer to a method of delaying or precluding the onset of a disease and/or its attendant symptoms, barring a subject from acquiring a disease or reducing a subject's risk of acquiring a disease.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The terms "treat", "treating" and "treatment", as used herein, are meant to include alleviating or abrogating a disease and/or its attendant symptoms and alleviating or eradicating the cause of the disease itself.

The term "alkyl," by itself or as part of another substituent, means, unless otherwise stated, a straight or branched chain hydrocarbon radical, or combination thereof, which is fully saturated, having the number of carbon atoms designated (i.e., $C_1$-$C_8$ means one to eight carbons). Examples of alkyl groups include methyl, ethyl, n-propyl, isopropyl, n-butyl, t-butyl, isobutyl, sec-butyl, homologs and isomers of, for example, n-pentyl, n-hexyl, n-heptyl, n-octyl and the like.

The term "alkenyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain hydrocarbon radical, or combinations thereof, consisting of the stated number of carbon atoms and from one to three heteroatoms selected from O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —Si(CH$_3$)$_3$, and —CH$_2$—CH=N—OCH$_3$. Up to two heteroatoms may be consecutive, such as, for example, —CH$_2$—NH—OCH$_3$ and —CH$_2$—O—Si(CH$_3$)$_3$. When a prefix such as ($C_2$-$C_8$) is used to refer to a heteroalkyl group, the number of carbons (2-8, in this example) is meant to include the heteroatoms as well. For example, a $C_2$-heteroalkyl group is meant to include, for example, —CH$_2$OH (one carbon atom and one heteroatom replacing a carbon atom) and —CH$_2$SH.

The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The term "heteroalkenyl," by itself or in combination with another term, means, unless otherwise stated, a stable straight or branched chain hydrocarbon radical, or combinations thereof, which may be mono- or polyunsaturated, having one or more double bonds, and having the stated number of carbon atoms and from one to three heteroatoms selected from O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH=CH—O—CH$_3$, —CH=CH—NH—CH$_3$, —CH=CH—N(CH$_3$)—CH$_3$, —CH$_2$—S—CH=CH$_2$ and —CH=CH—S(O)—CH$_3$.

The terms "cycloalkyl" and "heterocycloalkyl", by themselves or in combination with other terms, represent, unless otherwise stated, cyclic versions of "alkyl"and "heteroalkyl", respectively. Thus, the terms "cycloalkyl" and "heterocycloalkyl" are meant to be included in the terms "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "cycloalkenyl" and "heterocycloalkenyl", by themselves or in combination with other terms, represent, unless otherwise stated, cyclic versions of "alkenyl" and "heteroalkenyl", respectively. Thus, the terms "cycloalkenyl" and "heterocycloalkenyl" are meant to be included in the terms "alkenyl" and heteroalkenyl", respectively. Additionally, for heterocycloalkenyl, a heteroatom can occupy the position at which the heterocycle is attached to the remainder of the molecule.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, purinyl, 2-benzimidazolyl, 5-indolyl, 1H-indazole, carbazole, α-carboline, β-carboline, γ-carboline, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl or quinolyl group which is unsubstituted or substituted.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R'", —CN and —NO$_2$, in a number ranging from zero to three, with those groups having zero, one or two substituents being particularly preferred. R', R" and R'" each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R', —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R', —CN and —NO$_2$.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Otherwise, R' is as defined above.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chiral auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, e.g., cancer therapeutic agents, research reagents, e.g., CRTH2 assay reagents, and diagnostic agents, e.g., in vivo imaging agents. All isotopic variations of the compounds of the invention, whether radioactive or not, are intended to be encompassed within the scope of the invention.

6.2. Embodiments

A class of compounds that modulate CRTH2 and/or DP and/or one or more other PGD2 receptors has been discovered. Depending on the biological environment (e.g., cell type, pathological condition of the host, etc.), these compounds can activate or inhibit the actions of CRTH2 and/or one or more other PGD2 receptors (e.g., ligand binding). By activating or inhibiting CRTH2 and/or one or more other PGD2 receptors, the compounds will find use as therapeutic agents capable of modulating diseases and conditions responsive to modulation of CRTH2 and/or one or more other PGD2 receptors and/or mediated by CRTH2 and/or one or more other PGD2 receptors. As noted above, examples of such diseases and conditions include inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion and urticaria. Additionally, the compounds are useful for the treatment and/or prevention of complications of these diseases and disorders (e.g., cardiovascular disease).

While the compounds of the invention are believed to exert their effects by interacting with CRTH2, the mechanism of action by which the compounds act is not a limiting embodiment of the invention. For example, compounds of the invention may interact with PGD2 receptor subtypes other than CRTH2, e.g., DP receptor, and/or other prostanoid receptors, e.g., thromboxane A2 (TXA2) receptor. Indeed, as alluded to above, the present invention specifically contemplates the use of the disclosed compounds to modulate one or more PGD2 receptors other than CRTH2.

Compounds contemplated by the invention include, but are not limited to, the exemplary compounds provided herein.

Compounds

In one aspect, the invention provides compounds of formula I:

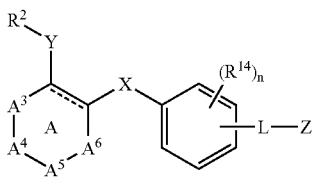

wherein A is 6-membered ring in which
$A^3$ is —C($R^3$)═, —N($R^3$)—, or —N═;
$A^4$ is —C($R^4$)═, —N($R^4$)—, or —N═;
$A^5$ is —C($R^5$)═, —N($R^5$)—, or —N═; and
$A^6$ is —C($R^6$)═, —N($R^6$)—, or —N═;
provided that at least one pair of $R^3$ and $R^4$, $R^4$ and $R^5$ or $R^5$ and $R^6$ form a 5- or 6-membered ring fused with A as defined below. In certain embodiments, ring A is aromatic. In some embodiments, ring A is not aromatic.

In formula I, X represents a divalent linkage selected from —O—, —S(O)$_k$—, —CR$^a$R$^b$—, —C(O)—, —NR$^8$— and —C(NR$^9$)—. Exemplary X groups are —O—, —SO$_2$—, —CH$_2$—, —C(O)—, —CH(OH)— and —NH—.

Y represents a divalent linkage selected from a single bond, —S(O)$_k$NR$^{10}$—, —C(O)NR$^{10}$—, (C$_1$-C$_4$)alkylene, hetero(C$_2$-C$_4$)alkylene, —N(R$^{11}$)C(O)NR$^{10}$—, —N(R$^{11}$)S(O)$_k$NR$^{10}$—, —N(R$^{11}$)CO$_2$—, —NR$^{11}$—, —O— and —S(O)$_k$—. Exemplary Y groups are —SO$_2$NH—, —SO$_2$NMe-, —C(O)NH—, —NH—, —NHCO$_2$— and —NHC(O)NMe-.

Z represents —CO$_2$R$^{12}$, —C(O)NR$^{12}$R$^{13}$ or heteroaryl. Exemplary Z groups are —CO$_2$H, —C(O)NHEt, —C(O)NH$_2$, —CO$_2$Et, —CO$_2$Me, —CO$_2$CH$_2$S(O)Me, 5-tetrazolyl and —C(O)NHOH.

L represents a divalent linkage selected from a single bond, (C$_1$-C$_6$)alkylene, (C$_2$-C$_6$)alkenylene, (C$_2$-C$_6$)alkynylene and (C$_2$-C$_4$)heteroalkylene. Exemplary L groups are methylene, ethylene, chloromethylene, hydroxymethylene and methylmethylene.

The substituent $R^2$ is hydrogen, (C$_1$-C$_8$)alkyl, cyclo(C$_3$-C$_8$)alkyl, cyclo(C$_3$-C$_8$)alkenyl, hetero(C$_2$-C$_8$)alkyl, heterocyclo(C$_3$-C$_8$)alkyl, heterocyclo(C$_3$-C$_8$)alkenyl, aryl, heteroaryl or aryl(C$_1$-C$_4$)alkyl. Exemplary $R^2$ groups are 4-tolyl, 2-naphthyl, methyl, phenyl, 2,4-dichlorophenyl, 4-methoxyphenyl, 4-trifluoromethoxyphenyl, 2-chlorophenyl, 4-chlorophenyl, 3-chlorophenyl, 2,4-dichloro-5-methylphenyl, 4-n-pentylphenyl, 4-cyanophenyl, 4-n-butoxyphenyl, 2-cyano-3-chlorophenyl, 3-chloro-4-methylphenyl, 2-methoxy-5-bromophenyl, 5-trifluoromethoxy-2-pyridyl, 8-quinolyl, 2-thienyl, 3-methyl-7-chlorobenzothienyl, 1-methyl-4-imidazolyl, benzyl and 2,4-difluorophenyl.

$R^3$, $R^4$, $R^5$ and $R^6$ are independently hydrogen, halogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —NR'R", —OR', —NO$_2$, —CN, —C(O)R', —CO$_2$R', —C(O)NR'R", (C$_1$-C$_4$)alkylene-C(O)NR'R", —S(O)$_m$R', —S(O)$_k$NR'R", —OC(O)OR', —OC(O)R', —OC(O)NR'R", —N(R''')C(O)NR'R", —N(R")C(O)R', —N(R")S(O)$_k$R' or —N(R")C(O)OR', provided that at least one pair of adjacent substituents of $R^3$ and $R^4$, $R^4$ and $R^5$, or $R^5$ and $R^6$ form a 5- or 6-membered ring containing 0, 1, 2 or 3 heteroatoms selected from N, O and S that is fused with ring A. Optionally, the fused 5- or 6-membered ring is substituted with halogen, (C$_1$-C$_3$)alkyl, halo(C$_1$-C$_3$)alkyl, cyclo(C$_3$-C$_5$)alkyl, cyclo(C$_3$-C$_5$)alkenyl, amino(C$_1$-C$_3$)alkyl, hydroxy, oxo, —OR', —CONR'R", —N(R")C(O)R', —CO$_2$R', —CN, aryl, or heteroaryl. In some embodiments, the fused 5- or 6-membered ring is aromatic. In certain embodiments, the fused 5- or 6-membered ring is not aromatic.

$R^8$, $R^{10}$ and $R^{11}$ are independently hydrogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —C(O)R', —CO$_2$R', —C(O)NR'R", —S(O)$_m$R' or —S(O)$_k$NR'R".

$R^9$ is hydrogen, (C$_1$-C$_6$)alkyl, hetero(C$_2$-C$_6$)alkyl, aryl(C$_1$-C$_4$)alkyl, —OR' or —NR'R".

$R^{12}$ and $R^{13}$ are independently hydrogen, (C$_1$-C$_6$)alkyl, hetero(C$_2$-C$_6$)alkyl, aryl, aryl(C$_1$-C$_4$)alkyl or heteroaryl.

Each $R^{14}$ is independently halogen, (C$_1$-C$_8$)alkyl, fluoro(C$_1$-C$_4$)alkyl, (C$_2$-C$_5$)alkenyl, —OR', —NR'R", —NO$_2$, —CN, C(O)R' or aryl. Optionally, a $R^{14}$ group and L taken together form a 5-, 6-, 7- or 8-membered fused ring containing from 0 to 3 heteroatoms selected from N, O and S.

$R^a$ and $R^b$ are independently hydrogen, (C$_1$-C$_6$)alkyl, hetero(C$_2$-C$_6$)alkyl, aryl(C$_1$-C$_4$)alkyl, —OR' or —NR'R".

Each R', R" and R''' is independently hydrogen, (C$_1$-C$_6$)alkyl, cyclo(C$_3$-C$_8$)alkyl, cyclo(C$_3$-C$_8$)alkenyl, aryl or aryl(C$_1$-C$_4$)alkyl.

Each subscript k is 0, 1 or 2.
The subscript m is 0, 1, 2 or 3.
The subscript n is 0, 1, 2, 3 or 4.

In certain embodiments of the compounds of formula I, the bond represented by "- - - - -" in ring A is a single bond. In other embodiments, the bond represented by "- - - - -" in ring A is a double bond.

In some embodiments, ring A is a nonaromatic ring and "- - - - -" is a double bond.

In certain embodiments, the invention provides compounds of formula II:

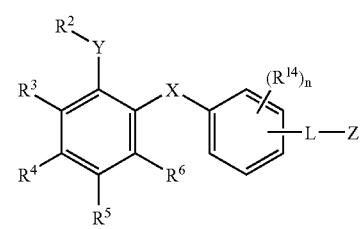

wherein X, Y, Z, L, $R^2$, $R^3$, $R^4$, $R^5$, $R^6$, $R^{14}$ and subscript n are as defined below.

In formula II, X represents a divalent linkage selected from —O—, —S(O)$_k$—, —CR$^a$R$^b$—, —C(O)—, —NR$^8$— and —C(NR$^9$)—. Exemplary X groups are —O—, —SO$_2$—, —CH$_2$—, —C(O)—, —CH(OH)— and —NH—.

Y represents a divalent linkage selected from a single bond, —S(O)$_k$NR$^{10}$—, —C(O)NR$^{10}$—, (C$_1$-C$_4$)alkylene, hetero(C$_2$-C$_4$)alkylene, —N(R$^{11}$)C(O)NR$^{10}$—, —N(R$^{11}$)S(O)$_k$NR$^{10}$—, —N(R$^{11}$)CO$_2$—, —NR$^{11}$—, —O— and —S(O)$_k$—. Exemplary Y groups are —SO$_2$NH—, —SO$_2$NMe-, —C(O)NH—, —NH—, —NHCO$_2$— and —NHC(O)NMe-.

Z represents —CO$_2$R$^{12}$, —C(O)NR$^{12}$R$^{13}$ or heteroaryl. Exemplary Z groups are —CO$_2$H, —C(O)NHEt, —C(O)NH$_2$, —CO$_2$Et, —CO$_2$Me, —CO$_2$CH$_2$S(O)Me, 5-tetrazolyl and —C(O)NHOH.

L represents a divalent linkage selected from a single bond, $(C_1-C_6)$alkylene, $(C_2-C_6)$alkenylene, $(C_2-C_6)$alkynylene and $(C_2-C_4)$heteroalkylene. Exemplary L groups are methylene, ethylene, chloromethylene, hydroxymethylene and methylmethylene.

The substituent $R^2$ is hydrogen, $(C_1-C_8)$alkyl, cyclo$(C_3-C_8)$alkyl, cyclo$(C_3-C_8)$alkenyl, hetero$(C_2-C_8)$alkyl, heterocyclo$(C_3-C_8)$alkyl, heterocyclo$(C_3-C_8)$alkenyl, aryl, heteroaryl or aryl$(C_1-C_4)$alkyl. Exemplary $R^2$ groups are 4-tolyl, 2-naphthyl, methyl, phenyl, 2,4-dichlorophenyl, 4-methoxyphenyl, 4-trifluoromethoxyphenyl, 2-chlorophenyl, 4-chlorophenyl, 3-chlorophenyl, 2,4-dichloro-5-methylphenyl, 4-n-pentylphenyl, 4-cyanophenyl, 4-n-butoxyphenyl, 2-cyano-3-chlorophenyl, 3-chloro-4-methylphenyl, 2-methoxy-5-bromophenyl, 5-trifluoromethoxy-2-pyridyl, 8-quinolyl, 2-thienyl, 3-methyl-7-chlorobenzothienyl, 1-methyl-4-imidazolyl, benzyl and 2,4-difluorophenyl.

$R^3$, $R^4$, $R^5$ and $R^6$ are independently hydrogen, halogen, $(C_1-C_8)$alkyl, fluoro$(C_1-C_4)$alkyl, hetero$(C_2-C_8)$alkyl, aryl, heteroaryl, aryl$(C_1-C_4)$alkyl, —NR'R", —OR', —NO$_2$, —CN, —C(O)R', —CO$_2$R', —C(O)NR'R", $(C_1-C_4)$alkylene-C(O)NR'R", —S(O)$_m$R', —S(O)$_k$NR'R", —OC(O)OR', —OC(O)R', —OC(O)NR'R", —N(R''')C(O)NR'R", —N(R")C(O)R', —N(R")S(O)$_k$R' or —N(R")C(O)OR', provided that at least one pair of adjacent substituents of $R^3$ and $R^4$, $R^4$ and $R^5$, or $R^5$ and $R^6$ form a fused 5- or 6-membered ring containing 0, 1, 2 or 3 heteroatoms selected from N, O and S. Optionally, the fused 5- or 6-membered ring is substituted with halogen, $(C_1-C_3)$alkyl, halo$(C_1-C_3)$alkyl, cyclo$(C_3-C_5)$alkyl, cyclo$(C_3-C_5)$alkenyl, amino$(C_1-C_3)$alkyl, hydroxy, oxo, —OR', —CONR'R", —N(R")C(O)R', —CO$_2$R', —CN, aryl, or heteroaryl. In some embodiments, the fused 5- or 6-membered ring is aromatic. In certain embodiments, the fused 5- or 6-membered ring is not aromatic.

$R^8$, $R^{10}$ and $R^{11}$ are independently hydrogen, $(C_1-C_8)$alkyl, fluoro$(C_1-C_4)$alkyl, hetero$(C_2-C_8)$alkyl, aryl, heteroaryl, aryl$(C_1-C_4)$alkyl, —C(O)R', —CO$_2$R', —C(O)NR'R", —S(O)$_m$R' or —S(O)$_k$NR'R".

$R^9$ is hydrogen, $(C_1-C_6)$alkyl, hetero$(C_2-C_6)$alkyl, aryl$(C_1-C_4)$alkyl, —OR' or —NR'R".

$R^{12}$ and $R^{13}$ are independently hydrogen, $(C_1-C_6)$alkyl, hetero$(C_2-C_6)$alkyl, aryl, aryl$(C_1-C_4)$alkyl or heteroaryl.

Each $R^{14}$ is independently halogen, $(C_1-C_8)$alkyl, fluoro$(C_1-C_4)$alkyl, $(C_2-C_5)$alkenyl, —OR', —NR'R", —NO$_2$, CN, —C(O)R' or aryl. Optionally, a $R^{14}$ group and L taken together form a 5-, 6-, 7- or 8-membered fused ring containing from 0 to 3 heteroatoms selected from N, O and S.

$R^a$ and $R^b$ are independently hydrogen, $(C_1-C_6)$alkyl, hetero$(C_2-C_6)$alkyl, aryl$(C_1-C_4)$alkyl, —OR' or —NR'R".

Each R', R" and R''' is independently hydrogen, $(C_1-C_6)$alkyl, cyclo$(C_3-C_8)$alkyl, cyclo$(C_3-C_8)$alkenyl, aryl or aryl$(C_1-C_4)$alkyl.

Each subscript k is 0, 1 or 2.

The subscript m is 0, 1, 2 or 3.

The subscript n is 0, 1, 2, 3 or 4.

In certain embodiments, the fused 5- or 6-membered ring formed by a pair of adjacent substituents of $R^3$ and $R^4$, $R^4$ and $R^5$, or $R^5$ and $R^6$ in formula II, can be a compound having formula III, IV or V:

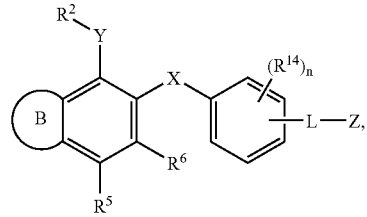

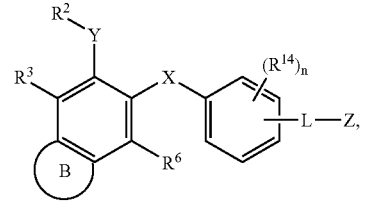

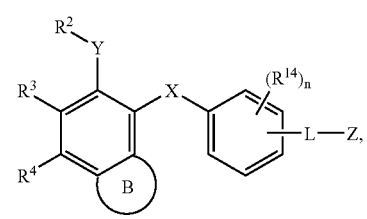

wherein X, Y, Z, L, $R^2$, $R^3$, $R^4$, $R^5$, $R^6$, $R^{14}$ and subscript n have the meanings and groupings provided above in formula II. In formulas III, IV and V, structure B represents a fused 5- or 6-membered ring containing 0, 1, 2 or 3 heteroatoms selected from N, O and S. Optionally, structure B is substituted with halogen, $(C_1-C_3)$alkyl, halo$(C_1-C_3)$alkyl, cyclo$(C_3-C_5)$alkyl, cyclo$(C_3-C_8)$alkenyl, amino$(C_1-C_3)$alkyl, hydroxy, oxo, —OR', —CONR'R", —N(R")C(O)R', —CO$_2$R', —CN, aryl, or heteroaryl, wherein R' and R" are each independently hydrogen, $(C_1-C_6)$alkyl, cyclo$(C_3-C_8)$alkyl, cyclo$(C3-C_8)$alkenyl, aryl or aryl$(C_1-C_4)$alkyl.

In some embodiments of formula III, IV or V, ring B is aromatic.

In certain embodiments, ring B is not aromatic.

Exemplary embodiments of the fused 5- or 6-membered ring formed by a pair of adjacent substituents of $R^3$ and $R^4$, $R^4$ and $R^5$, or $R^5$ and $R^6$ in formula I, including, for example, structure B in formulas III, IV and V, are as shown below, where dotted lines indicate the carbon atoms that form a common bond in the fused ring structure of formula II, III, IV or V:

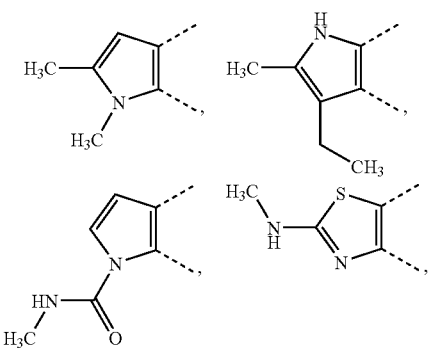

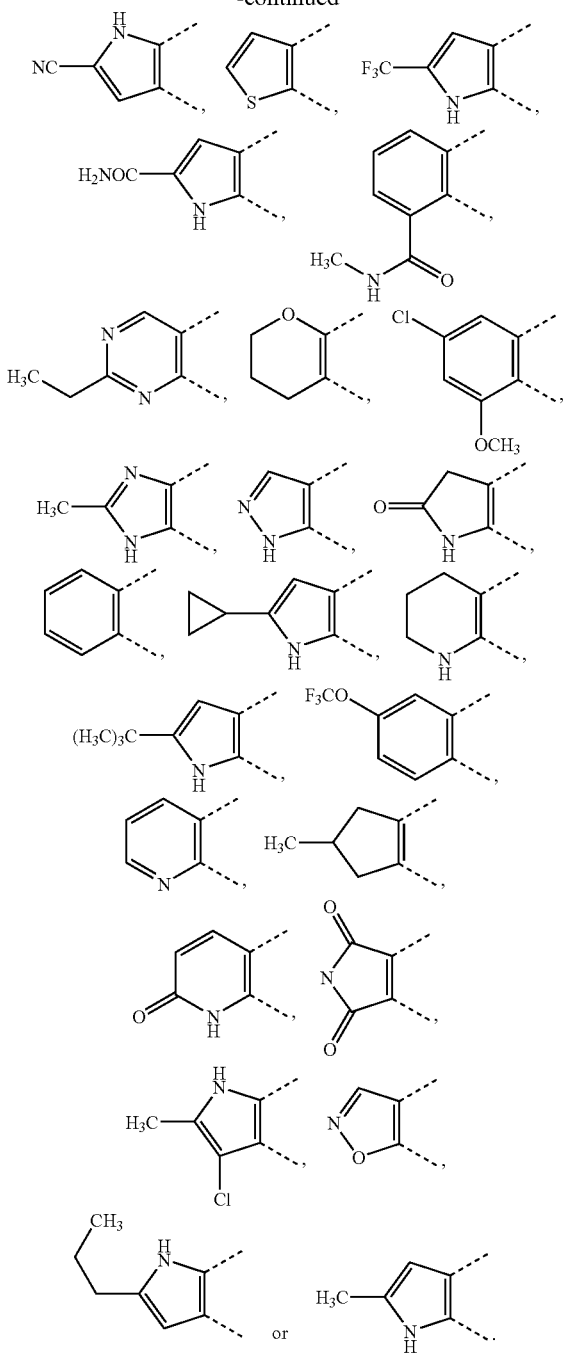

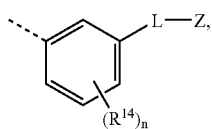

One of skill in the art will understand that a number of structural isomers are represented by formula II, III, IV or V. For example, structural isomers a, b and c of formula II, III, IV or V, where the dotted line represents the attachment to X in formula II, III, IV or V, are:

IIa, IIIa, IVa, or Va

IIb, IIIb, IVb, or Vb

IIc, IIIc, IVc, or Vc

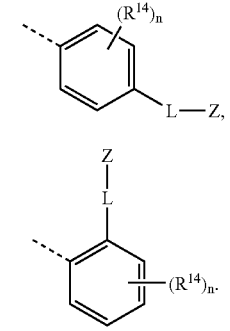

In another embodiment, the invention provides compounds of formula VI:

VI

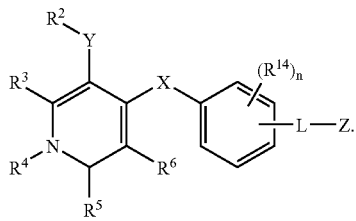

In formula VI, X represents a divalent linkage selected from —O—, —S(O)$_k$—, CR$^a$R$^b$—, —C(O)—, —NR$^8$— and —C(NR$^9$)—. Exemplary X groups are —O—, —SO$_2$—, —CH$_2$—, —C(O)—, —CH(OH)— and —NH—.

Y represents a divalent linkage selected from a single bond, —S(O)$_k$NR$^{10}$—, —C(O)NR$^{10}$—, (C$_1$-C$_4$)alkylene, hetero(C$_2$-C$_4$)alkylene, —N(R$^{11}$)C(O)NR$^{10}$—, —N(R$^{11}$)S(O)$_k$NR$^{10}$—, —N(R$^{11}$)CO$_2$—, —NR$^{11}$—, —O— and —S(O)$_k$—. Exemplary Y groups are —SO$_2$NH—, —SO$_2$NMe-, —C(O)NH—, —NH—, —NHCO$_2$— and —NHC(O)NMe-.

Z represents —CO$_2$R$^{12}$, —C(O)NR$^{12}$R$^{13}$ or heteroaryl. Exemplary Z groups are —CO$_2$H, —C(O)NHEt, —C(O)NH$_2$, —CO$_2$Et, —CO$_2$Me, —CO$_2$CH$_2$S(O)Me, 5-tetrazolyl and —C(O)NHOH.

L represents a divalent linkage selected from a single bond, (C$_1$-C$_6$)alkylene, (C$_2$-C$_6$)alkenylene, (C$_2$-C$_6$)alkynylene and (C$_2$-C$_4$)heteroalkylene. Exemplary L groups are methylene, ethylene, chloromethylene, hydroxymethylene and methylmethylene.

The substituent R$^2$ is hydrogen, (C$_1$-C$_8$)alkyl, cyclo(C$_3$-C$_8$)alkyl, cyclo(C$_3$-C$_8$)alkenyl, hetero(C$_2$-C$_8$)alkyl, heterocyclo(C$_3$-C$_8$)alkyl, heterocyclo(C$_3$-C$_8$)alkenyl, aryl, heteroaryl or aryl(C$_1$-C$_4$)alkyl. Exemplary R$^2$ groups are 4-tolyl, 2-naphthyl, methyl, phenyl, 2,4-dichlorophenyl, 4-methoxyphenyl, 4-trifluoromethoxyphenyl, 2-chlorophenyl, 4-chlorophenyl, 3-chlorophenyl, 2,4-dichloro-5-methylphenyl, 4-n-pentylphenyl, 4-cyanophenyl, 4-n-butoxyphenyl, 2-cyano-3-chlorophenyl, 3-chloro-4-methylphenyl, 2-methoxy-5-bromophenyl, 5-trifluoromethoxy-2-pyridyl, 8-quinolyl, 2-thienyl, 3-methyl-7-chlorobenzothienyl, 1-methyl-4-imidazolyl, benzyl and 2,4-difluorophenyl.

R$^3$, R$^4$, R$^5$ and R$^6$ are independently hydrogen, halogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —NR'R'', —OR', —NO$_2$, —CN, —C(O)R', —CO$_2$R', —C(O)NR'R'', (C$_1$-C$_4$)alkylene-C(O)NR'R'', —S(O)$_m$R', —S(O)$_k$NR'R'', —OC(O)OR', —OC(O)R', —OC(O)NR'R'', —N(R''')C(O)NR'R'', —N(R")C(O)R', —N(R")S(O)$_k$R' or —N(R")C(O)OR', provided that at least one pair of adjacent substituents of R$^3$ and R$^4$, R$^4$ and R$^5$, or R$^5$ and R$^6$ form a fused 5- or 6-membered ring containing 0, 1, 2 or 3 heteroatoms selected from N, O and S. Optionally, the fused 5- or 6-membered ring is substituted with halogen, (C$_1$-C$_3$)alkyl, halo(C$_1$-C$_3$)alkyl, cyclo(C$_3$-C$_5$)alkyl, cyclo(C$_3$-C$_5$)alkenyl, amino(C$_1$-C$_3$)alkyl, hydroxy, oxo, —OR', —CONR'R", —N(R")C(O)R', —CO$_2$R', —CN, aryl, or heteroaryl. In some embodiments, the fused 5- or 6-membered ring is aromatic. In certain embodiments, the fused 5- or 6-membered ring is not aromatic.

R$^8$, R$^{10}$ and R$^{11}$ are independently hydrogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —C(O)R', —CO$_2$R', C(O)NR'R", —S(O)$_m$R' or —S(O)$_k$NR'R".

R$^9$ is hydrogen, (C$_1$-C$_6$)alkyl, hetero(C$_2$-C$_6$)alkyl, aryl(C$_1$-C$_4$)alkyl, —OR' or —NR'R".

R$^{12}$ and R$^{13}$ are independently hydrogen, (C$_1$-C$_6$)alkyl, hetero(C$_2$-C$_6$)alkyl, aryl, aryl(C$_1$-C$_4$)alkyl or heteroaryl.

Each R$^{14}$ is independently halogen, (C$_1$-C$_8$)alkyl, fluoro(C$_1$-C$_4$)alkyl, (C$_2$-C$_5$)alkenyl, —OR', —NR'R", —NO$_2$, CN, C(O)R' or aryl. Optionally, a R$^{14}$ group and L taken together form a 5-, 6-, 7- or 8-membered fused ring containing from 0 to 3 heteroatoms selected from N, O and S.

R$^a$ and R$^b$ are independently hydrogen, (C$_1$-C$_6$)alkyl, hetero(C$_2$-C$_6$)alkyl, aryl(C$_1$-C$_4$)alkyl, —OR' or —NR'R". Each R', R" and R''' is independently hydrogen, (C$_1$-C$_6$)alkyl, cyclo(C$_3$-C$_8$)alkyl, cyclo(C$_3$-C$_8$)alkenyl, aryl or aryl(C$_1$-C$_4$)alkyl.

Each subscript k is 0, 1 or 2.
The subscript in is 0, 1, 2 or 3.
The subscript n is 0, 1, 2, 3 or 4.

In certain embodiments, the fused 5- or 6-membered ring formed by a pair of adjacent substituents of R$^3$ and R$^4$, R$^4$ and R$^5$, or R$^5$ and R$^6$ in formula VI, can be a compound having formula VII, VIII or IX:

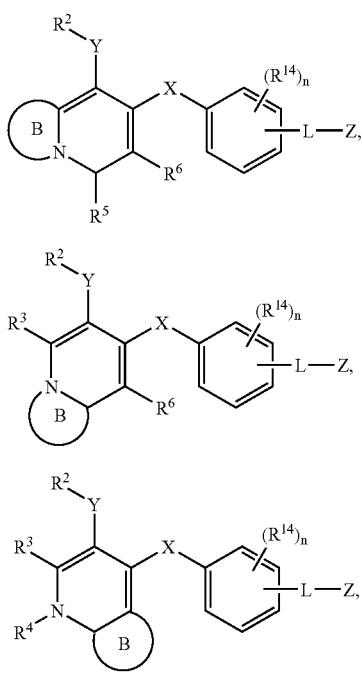

wherein X, Y, Z, L, R$^2$, R$^3$, R$^4$, R$^5$, R$^6$, R$^{14}$ and subscript n have the meanings and groupings provided above in formula VI. In formulas VII, VIII and IX, structure B represents a fused 5- or 6-membered ring containing 0, 1, 2 or 3 heteroatoms selected from N, O and S. Optionally, structure B is substituted with halogen, (C$_1$-C$_3$)alkyl, halo(C$_1$-C$_3$)alkyl, cyclo(C$_3$-C$_5$)alkyl, cyclo(C$_3$-C$_5$)alkenyl, amino(C$_1$-C$_3$)alkyl, hydroxy, oxo, —OR', —CONR'R", —N(R")C(O)R', —CO$_2$R', —CN, aryl, or heteroaryl, wherein R' and R" are each independently hydrogen, (C$_1$-C$_6$)alkyl, cyclo(C$_3$-C$_8$)alkyl, cyclo(C$_3$-C$_8$)alkenyl, aryl or aryl(C$_1$-C$_4$)alkyl.

In some embodiments of formula VII, VIII or IX, ring B is aromatic.

In certain embodiments, ring B is not aromatic.

Exemplary embodiments of the fused 5- or 6-membered ring formed by a pair of ajdacent substituents of R$^5$ and R$^6$ in formula VI, for instance, structure B in formula IX, include those described above with respect to formula II.

Exemplary embodiments of the fused 5- or 6-membered ring formed by a pair of adjacent substituents of R$^3$ and R$^4$, or R$^4$ and R$^5$ in formula VI, including, for example, structure B in formulas VII and VIII, are as shown below, where dotted lines indicate the two atoms that form a common bond in the fused ring structure of formula VII, or VIII:

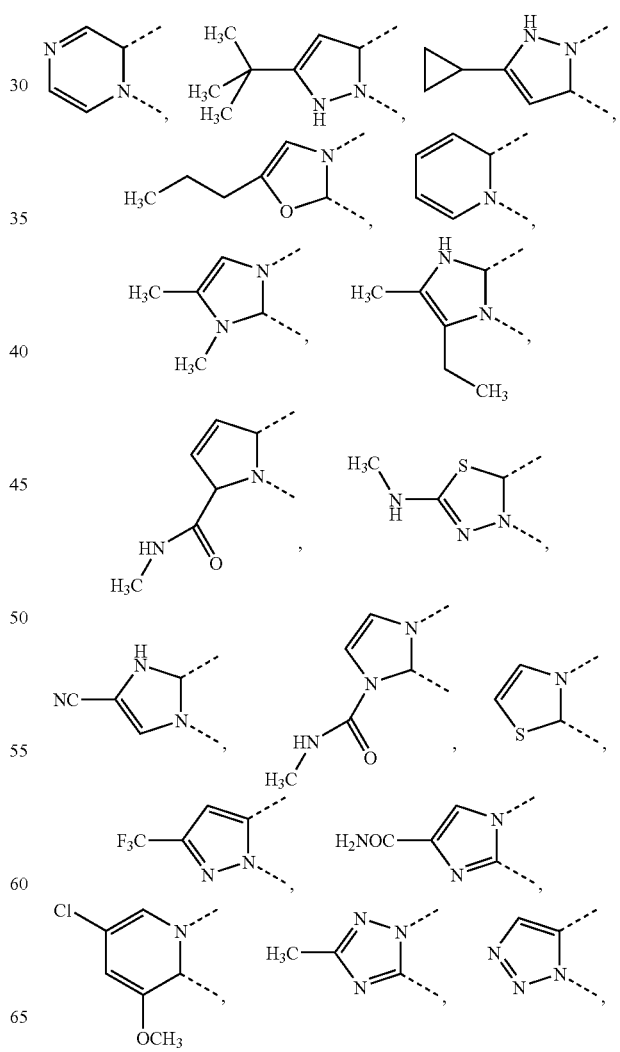

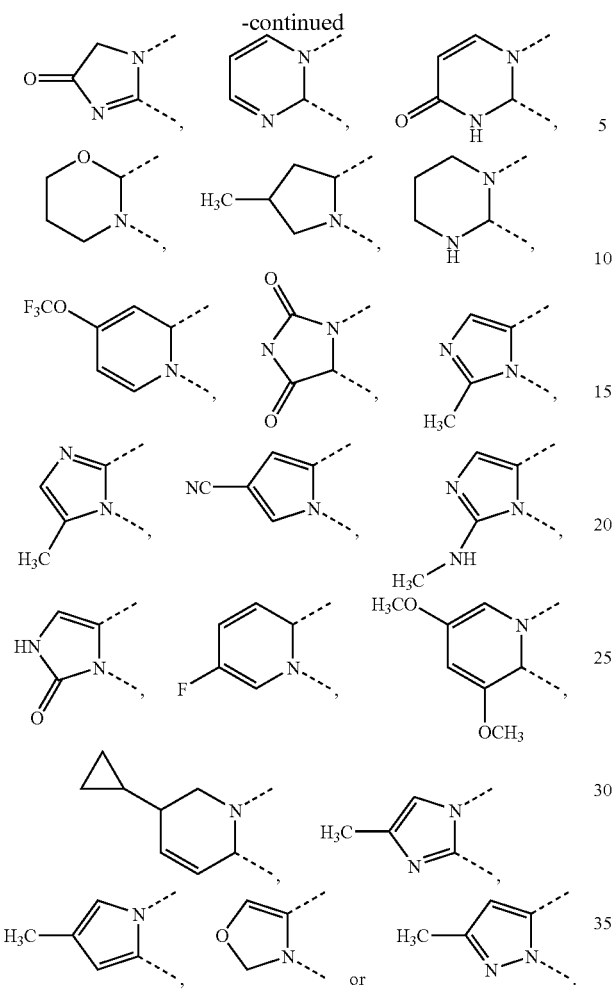

In certain embodiments, the invention provides compounds of formula X:

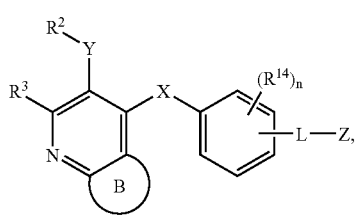

wherein symbols X, Y, Z, L, $R^2$, $R^3$, $R^{14}$ and subscript n are as described above with regard to formula VI, and wherein structure B represents a fused 5- or 6-membered ring containing 0, 1, 2 or 3 heteroatoms selected from N, O and S. Optionally, structure B is substituted with halogen, $(C_1\text{-}C_3)$alkyl, halo$(C_1\text{-}C_3)$alkyl, cyclo$(C_3\text{-}C_5)$alkyl, cyclo$(C_3\text{-}C_5)$alkenyl, amino$(C_1\text{-}C_3)$alkyl, hydroxy, oxo, —OR', —CONR'R", —N(R")C(O)R', —CO$_2$R', —CN, aryl, or heteroaryl, wherein R' and R" are each independently hydrogen, $(C_1\text{-}C_6)$alkyl, cyclo$(C_3\text{-}C_8)$alkyl, cyclo$(C_3\text{-}C_8)$alkenyl, aryl or aryl$(C_1\text{-}C_4)$alkyl. In some embodiments, structure B is aromatic. In other embodiments, structure B is not aromatic. Exemplary embodiments of structure B in formula X, include those described above with respect to formula II.

In another aspect, the invention provides compounds of formula XI:

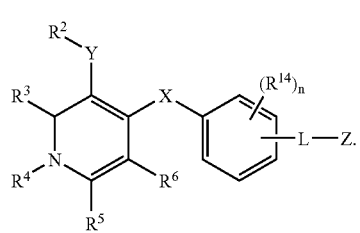

In formula XI, the symbols X, Y, Z, L, $R^2$, $R^3$, $R^4$, $R^5$, $R^6$, $R^{14}$ and subscript n are as described above with regard to formula VI.

In certain embodiments, the fused 5- or 6-membered ring formed by a pair of adjacent substituents of $R^3$ and $R^4$, $R^4$ and $R^5$, or $R^5$ and $R^6$ in formula XI, can be a compound having formula XII, XIII or XIV:

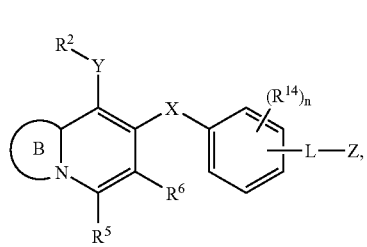

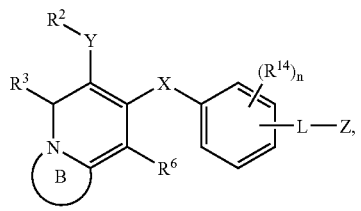

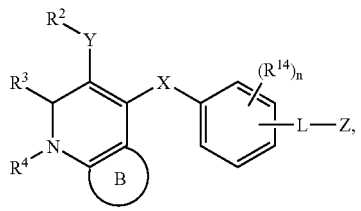

wherein X, Y, Z, L, $R^2$, $R^3$, $R^4$, $R^5$, $R^6$, $R^{14}$ and subscript n have the meanings and groupings provided above in formula VI. In formulas XII, XIII and XIV, structure B represents a fused 5- or 6-membered ring containing 0, 1, 2 or 3 heteroatoms selected from N, O and S. Optionally, structure B is substituted with halogen, $(C_1\text{-}C_3)$alkyl, halo$(C_1\text{-}C_3)$alkyl, cyclo$(C_3\text{-}C_5)$alkyl, cyclo$(C_3\text{-}C_5)$alkenyl, amino$(C_1\text{-}C_3)$alkyl, hydroxy, oxo, —OR', —CONR'R", —N(R")C(O)R', —CO$_2$R', —CN, aryl, or heteroaryl, wherein R' and R" are each independently hydrogen, $(C_1\text{-}C_6)$alkyl, cyclo$(C_3\text{-}C_8)$alkyl, cyclo$(C_3\text{-}C_8)$alkenyl, aryl or aryl$(C_1\text{-}C_4)$alkyl.

In some embodiments of formula XII, XIII or XIV, ring B is aromatic.

In certain embodiments, ring B is not aromatic.

Exemplary embodiments of the fused 5- or 6-membered ring formed by a pair of adjacent substituents of $R^5$ and $R^6$ in formula XI, for instance, structure B in formula XIV, include those described above with respect to formula II.

Exemplary embodiments of the fused 5- or 6-membered ring formed by a pair of adjacent substituents of $R^3$ and $R^4$, or $R^4$ and $R^5$ in formula XI, including, for example, structure B in formulas XII and XIII, include those described above with regard to formulas VII or VIII.

In another aspect, the invention provides compounds of formula XV:

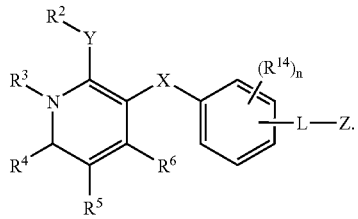

XV

In formula XV, the symbols X, Y, Z, L, $R^2$, $R^3$, $R^4$, $R^5$, $R^6$, $R^{14}$ and subscript n are as described above with regard to formula VI.

In certain embodiments, the fused 5- or 6-membered ring formed by a pair of adjacent substituents of $R^3$ and $R^4$, $R^4$ and $R^5$, or $R^5$ and $R^6$ in formula XV, can be a compound having formula XVI, XVII or XVIIII:

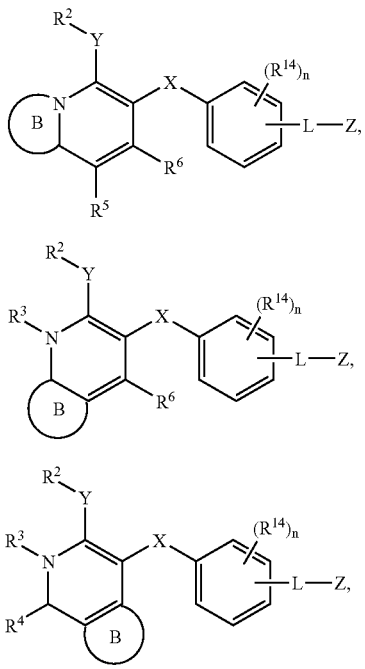

XVI

XVII

XVIII wherein X, Y, Z, L, $R^2$, $R^3$, $R^4$, $R^5$, $R^6$, $R^{14}$ and subscript n have the meanings and groupings provided above in formula VI. In formulas XVI, XVII and XVIII, structure B represents a fused 5- or 6-membered ring containing 0, 1, 2 or 3 heteroatoms selected from N, O and S. Optionally, structure B is substituted with halogen, $(C_1$-$C_3)$alkyl, halo$(C_1$-$C_3)$alkyl, cyclo$(C_3$-$C_5)$alkyl, cyclo$(C_3$-$C_5)$alkenyl, amino$(C_1$-$C_3)$ alkyl, hydroxy, oxo, —OR', —CONR'R", —N(R")C(O)R', —CO$_2$R', —CN, aryl, or heteroaryl, wherein R' and R" are each independently hydrogen, $(C_1$-$C_6)$alkyl, cyclo$(C_3$-$C_8)$ alkyl, cyclo$(C_3$-$C_8)$alkenyl, aryl or aryl$(C_1$-$C_4)$alkyl.

In some embodiments of formula XVI, XVII and XVIII, ring B is aromatic.

In certain embodiments, ring B is not aromatic.

Exemplary embodiments of the fused 5- or 6-membered ring formed by a pair of adjacent substituents of $R^4$ and $R^5$ or $R^5$ and $R^6$ in formula XV, for instance, structure B in formulas XVII and XVIII, include those described above with respect to formula II.

Exemplary embodiments of the fused 5- or 6-membered ring formed by a pair of adjacent substituents of $R^3$ and $R^4$ in formula XV, including, for example, structure B in formula XVI, include those described above with regard to formulas VII or VIII.

In certain embodiments, the invention provides compounds of formula XIX or XX:

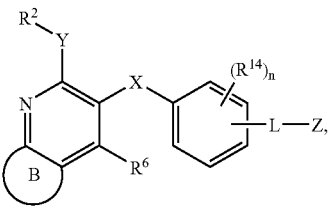

XIX

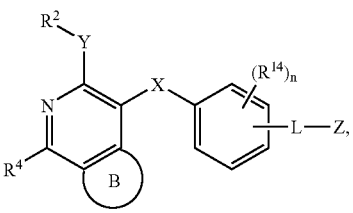

XX wherein symbols X, Y, Z, L, $R^2$, $R^4$, $R^6$, $R^{14}$ and subscript n are as described above with regard to formula VI, and wherein structure B represents a fused 5- or 6-membered ring containing 0, 1, 2 or 3 heteroatoms selected from N, O and S. Optionally, structure B is substituted with halogen, $(C_1$-$C_3)$ alkyl, halo$(C_1$-$C_3)$alkyl, cyclo$(C_3$-$C_5)$alkyl, cyclo$(C_3$-$C_5)$ alkenyl, amino$(C_1$-$C_3)$alkyl, hydroxy, oxo, —OR', —CONR'R", —N(R")C(O)R', —CO$_2$R', —CN, aryl, or heteroaryl, wherein R' and R" are each independently hydrogen, $(C_1$-$C_6)$alkyl, cyclo$(C_3$-$C_8)$alkyl, cyclo$(C_3$-$C_8)$alkenyl, aryl or aryl$(C_1$-$C_4)$alkyl. In some embodiments, structure B is aromatic. In other embodiments, structure B is not aromatic. Exemplary embodiments of structure B in formulas XIX and XX, include those described above with respect to formula II.

In some embodiments, the invention provides compounds of formula XXI:

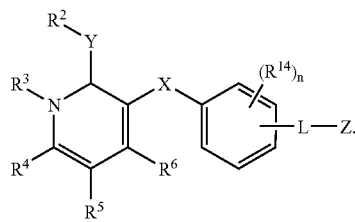

XXI

In formula XXI, the symbols X, Y, Z, L, $R^2$, $R^3$, $R^4$, $R^5$, $R^6$, $R^{14}$ and subscript n are as described above with regard to formula VI.

In certain embodiments, the fused 5- or 6-membered ring formed by a pair of adjacent substituents of $R^3$ and $R^4$, $R^4$ and $R^5$, or $R^5$ and $R^6$ in formula XXI, can be a compound having formula XXII, XXIII or XXIV:

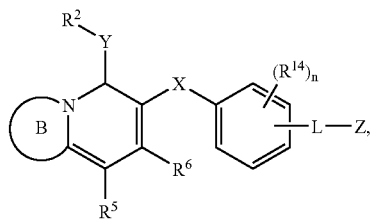

XXII

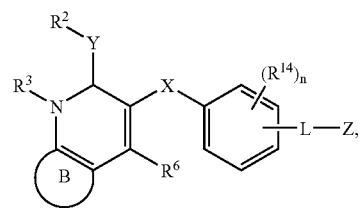

XXIII

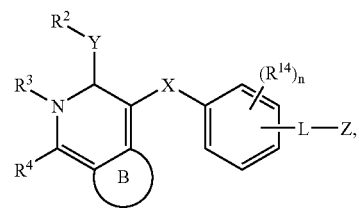

XXIV wherein X, Y, Z, L, $R^2$, $R^3$, $R^4$, $R^5$, $R^6$, $R^{14}$ and subscript n have the meanings and groupings provided above in formula VI. In formulas XXII, XXIII or XXIV, structure B represents a fused 5- or 6-membered ring containing 0, 1, 2 or 3 heteroatoms selected from N, O and S. Optionally, structure B is substituted with halogen, ($C_1$-$C_3$)alkyl, halo($C_1$-$C_3$)alkyl, cyclo($C_3$-$C_5$)alkyl, cyclo($C_3$-$C_5$)alkenyl, amino($C_1$-$C_3$)alkyl, hydroxy, oxo, —OR', —CONR'R", —N(R")C(O)R', —$CO_2$R', —CN, aryl, or heteroaryl, wherein R' and R" are each independently hydrogen, ($C_1$-$C_6$)alkyl, cyclo($C_3$-$C_8$)alkyl, cyclo($C_3$-$C_8$)alkenyl, aryl or aryl($C_1$-$C_4$)alkyl.

In some embodiments of formula XXII, XXIII or XXIV, ring B is aromatic.

In certain embodiments, ring B is not aromatic.

Exemplary embodiments of the fused 5- or 6-membered ring formed by a pair of adjacent substituents of $R^4$ and $R^5$ or $R^5$ and $R^6$ in formula XXI, for instance, structure B in formulas XXIII and XXIV, include those described above with respect to formula II.

Exemplary embodiments of the fused 5- or 6-membered ring formed by a pair of adjacent substituents of $R^3$ and $R^4$ in formula XXI, including, for example, structure B in formula XXII, include those described above with regard to formulas VII and VIII.

In certain embodiments, the invention provides compounds of formula XXV:

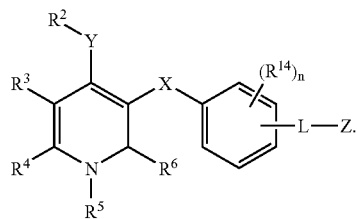

XXV

In formula XXV, the symbols X, Y, Z, L, $R^2$, $R^3$, $R^4$, $R^5$, $R^6$, $R^{14}$ and subscript n are as described above with regard to formula VI.

In certain embodiments, the fused 5- or 6-membered ring formed by a pair of adjacent substituents of $R^3$ and $R^4$, $R^4$ and $R^5$, or $R^5$ and $R^6$ in formula XXV, can be a compound having formula XXVI, XXVII or XXVIII:

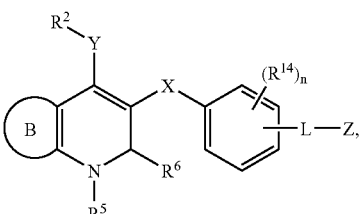

XXVI

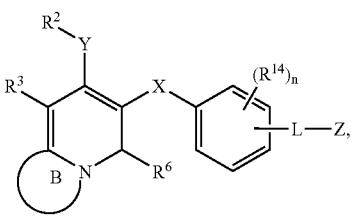

XXVII

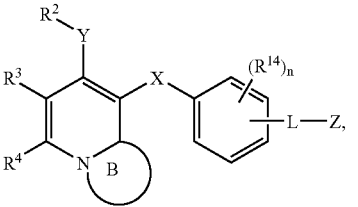

XXVIII wherein X, Y, Z, L, $R^2$, $R^3$, $R^4$, $R^5$, $R^6$, $R^{14}$ and subscript n have the meanings and groupings provided above in formula VI. In formulas XXVI, XXVII or XXVIII, structure B represents a fused 5- or 6-membered ring containing 0, 1, 2 or 3 heteroatoms selected from N, O and S. Optionally, structure B is substituted with halogen, ($C_1$-$C_3$)alkyl, halo($C_1$-$C_3$)alkyl, cyclo($C_3$-$C_5$)alkyl, cyclo($C_3$-$C_5$)alkenyl, amino($C_1$-$C_3$)alkyl, hydroxy, oxo, —OR', —CONR'R", —N(R")C(O)R', —$CO_2$R', —CN, aryl, or heteroaryl, wherein R' and R" are each independently hydrogen, ($C_1$-$C_6$)alkyl, cyclo($C_3$-$C_8$)alkyl, cyclo($C_3$-$C_8$)alkenyl, aryl or aryl($C_1$-$C_4$)alkyl.

In some embodiments of formula XXVI, XXVII or XXVIII, ring B is aromatic.

In certain embodiments, ring B is not aromatic.

Exemplary embodiments of the fused 5- or 6-membered ring formed by a pair of adjacent substituents of $R^3$ and $R^4$ in formula XXV, for instance, structure B in formula XXVI, include those described above with respect to formula II.

Exemplary embodiments of the fused 5- or 6-membered ring formed by a pair of adjacent substituents of $R^4$ and $R^5$, or $R^5$ and $R^6$ in formula XXV, including, for example, structure B in formulas XXVII and XXVIII, include those described above with regard to formulas VII or VIII.

In certain embodiments, the invention provides compounds of formula XXIX:

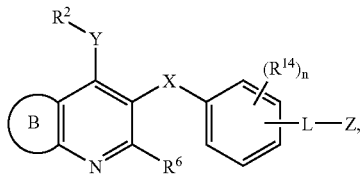

XXIX wherein symbols X, Y, Z, L, $R^2$, $R^6$, $R^{14}$ and subscript n are as described above with regard to formula VI, and wherein structure B represents a fused 5- or 6-membered ring containing 0, 1, 2 or 3 heteroatoms selected from N, O and S. Optionally, structure B is substituted with halogen, $(C_1-C_3)$alkyl, halo$(C_1-C_3)$alkyl, cyclo$(C_3-C_5)$alkyl, cyclo$(C_3-C_5)$alkenyl, amino$(C_1-C_3)$alkyl, hydroxy, oxo, —OR', —CONR'R", —N(R")C(O)R', —$CO_2R'$, —CN, aryl, or heteroaryl, wherein R' and R" are each independently hydrogen, $(C_1-C_6)$ alkyl, cyclo$(C_3-C_8)$alkyl, cyclo$(C_3-C_8)$alkenyl, aryl or aryl $(C_1-C_4)$alkyl. In some embodiments, structure B is aromatic. In other embodiments, structure B is not aromatic. Exemplary embodiments of structure B in formula XXIX, include those described above with respect to formula II.

In another aspect, the invention provides compounds of formula XXX:

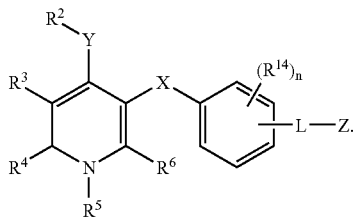

XXX

In formula XXX, the symbols X, Y, Z, L, $R^2$, $R^3$, $R^4$, $R^5$, $R^6$, $R^{14}$ and subscript n are as described above with regard to formula VI.

In certain embodiments, the fused 5- or 6-membered ring formed by a pair of adjacent substituents of $R^3$ and $R^4$, $R^4$ and $R^5$, or $R^5$ and $R^6$ in formula XXX, can be a compound having formula XXXI, XXXII or XXXIII:

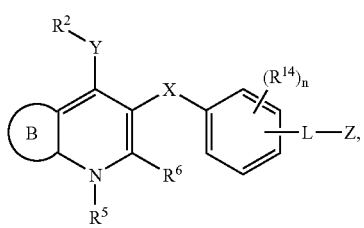

XXXI

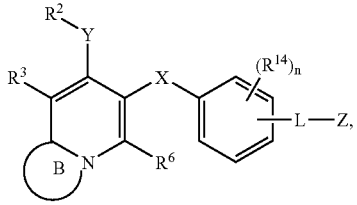

XXXII

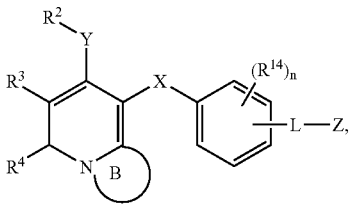

XXXIII wherein X, Y, Z, L, $R^2$, $R^3$, $R^4$, $R^5$, $R^6$, $R^{14}$ and subscript n have the meanings and groupings provided above in formula VI. In formulas XXXI, XXXII or XXXIII, structure B represents a fused 5- or 6-membered ring containing 0, 1, 2 or 3 heteroatoms selected from N, O and S. Optionally, structure B is substituted with halogen, $(C_1-C_3)$alkyl, halo$(C_1-C_3)$alkyl, cyclo$(C_3-C_5)$alkyl, cyclo$(C_3-C_5)$alkenyl, amino$(C_1-C_3)$ alkyl, hydroxy, oxo, —OR', —CONR'R", —N(R")C(O)R', —$CO_2R'$, —CN, aryl, or heteroaryl, wherein R' and R" are each independently hydrogen, $(C_1-C_6)$alkyl, cyclo$(C_3-C_8)$ alkyl, cyclo$(C_3-C_8)$alkenyl, aryl or aryl$(C_1-C_4)$alkyl.

In some embodiments of formula XXXI, XXXII or XXXIII, ring B is aromatic.

In certain embodiments, ring B is not aromatic.

Exemplary embodiments of the fused 5- or 6-membered ring formed by a pair of adjacent substituents of $R^3$ and $R^4$ in formula XXX, for instance, structure B in formula XXXI, include those described above with respect to formula II.

Exemplary embodiments of the fused 5- or 6-membered ring formed by a pair of adjacent substituents of $R^4$ and $R^5$, or $R^5$ and $R^6$ in formula XXX, including, for example, structure B in formulas XXXII and XXXII, include those described above with regard to formulas VII and VIII.

In another aspect, the invention provides compounds of formula XXXIV:

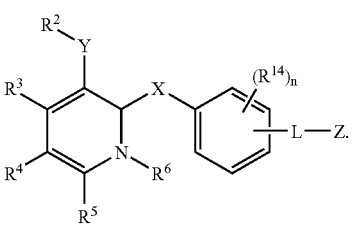

XXXIV

In formula XXXIV, the symbols X, Y, Z, L, $R^2$, $R^3$, $R^4$, $R^5$, $R^6$, $R^{14}$ and subscript n are as described above with regard to formula VI.

In certain embodiments, the fused 5- or 6-membered ring formed by a pair of adjacent substituents of $R^3$ and $R^4$, $R^4$ and $R^5$, or $R^5$ and $R^6$ in formula XXXIV, can be a compound having formula XXXV, XXXVI or XXXVII:

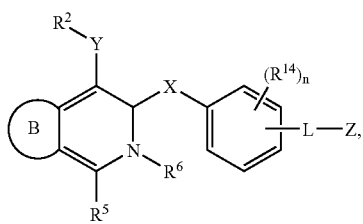

XXXV

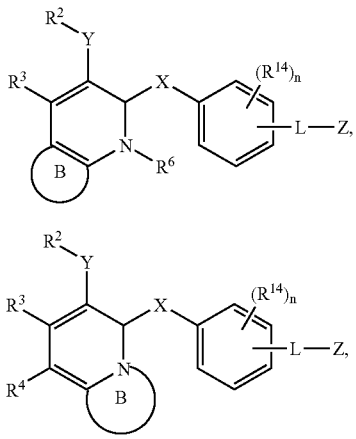

XXXVI

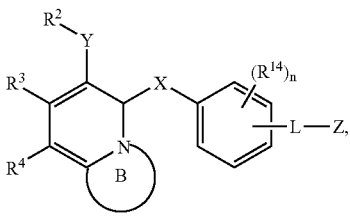

XXXVII wherein X, Y, Z, L, R², R³, R⁴, R⁵, R⁶, R¹⁴ and subscript n have the meanings and groupings provided above in formula VI. In formulas XXXV, XXXVI and XXXVII, structure B represents a fused 5- or 6-membered ring containing 0, 1, 2 or 3 heteroatoms selected from N, O and S. Optionally, structure B is substituted with halogen, ($C_1$-$C_3$) alkyl, halo($C_1$-$C_3$) alkyl, cyclo($C_3$-$C_5$)alkyl, cyclo($C_3$-$C_5$)alkenyl, amino($C_1$-$C_3$)alkyl, hydroxy, oxo, —OR', —CONR'R", —N(R")C(O) R', —CO₂R', —CN, aryl, or heteroaryl, wherein R' and R" are each independently hydrogen, ($C_1$-$C_6$)alkyl, cyclo($C_3$-$C_8$) alkyl, cyclo($C_3$-$C_8$)alkenyl, aryl or aryl($C_1$-$C_4$)alkyl.

In some embodiments of formula XXXV, XXXVI or XXXVII, ring B is aromatic.

In certain embodiments, ring B is not aromatic.

Exemplary embodiments of the fused 5- or 6-membered ring formed by a pair of adjacent substituents of R³ and R⁴ or R⁴ and R⁵ in formula XXXIV, for instance, structure B in formulas XXXV and XXXVI, include those described above with respect to formula II.

Exemplary embodiments of the fused 5- or 6-membered ring formed by a pair of adjacent substituents of R⁵ and R⁶ in formula XXXIV, including, for example, structure B in formula XXXVII, include those described above with regard to formulas VII or VIII.

In certain embodiments, the invention provides compounds of formula XXXVIII or XXXIX:

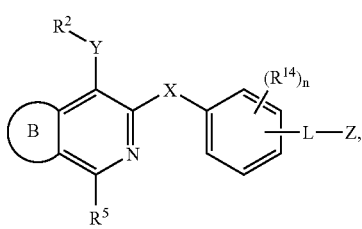

XXXVIII

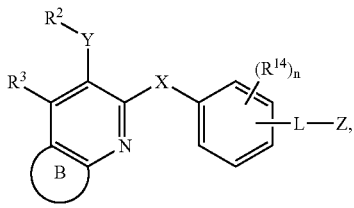

XXXIX wherein symbols X, Y, Z, L, R², R³, R⁵, R¹⁴ and subscript n are as described above with regard to formula VI, and wherein structure B represents a fused 5- or 6-membered ring containing 0, 1, 2 or 3 heteroatoms selected from N, O and S. Optionally, structure B is substituted with halogen, ($C_1$-$C_3$) alkyl, halo($C_1$-$C_3$)alkyl, cyclo($C_3$-$C_5$)alkyl, cyclo($C_3$-$C_5$) alkenyl, amino($C_1$-$C_3$)alkyl, hydroxy, oxo, —OR', —CONR'R", —N(R")C(O)R', —CO₂R', —CN, aryl, or heteroaryl, wherein R' and R" are each independently hydrogen, ($C_1$-$C_6$)alkyl, cyclo($C_3$-$C_8$)alkyl, cyclo($C_3$-$C_8$)alkenyl, aryl or aryl($C_1$-$C_4$)alkyl. In some embodiments, structure B is aromatic. In other embodiments, structure B is not aromatic. Exemplary embodiments of structure B in formulas XXXVIII and XXXIX, include those described above with respect to formula II.

In another aspect, the invention provides compounds of formula XXXX:

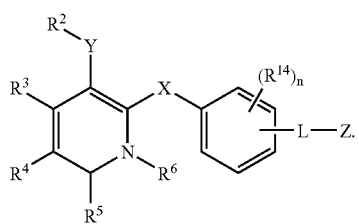

XXXX

In formula XXXX, the symbols X, Y, Z, L, R², R³, R⁴, R⁵, R⁶, R¹⁴ and subscript n are as described above with regard to formula VI.

In certain embodiments, the fused 5- or 6-membered ring formed by a pair of adjacent substituents of R³ and R⁴, R⁴ and R⁵, or R⁵ and R⁶ in formula XXXX, can be a compound having formula XXXXI, XXXXII or XXXXIII:

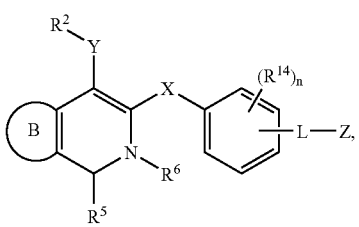

XXXXI

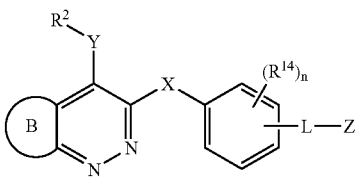

XXXXII

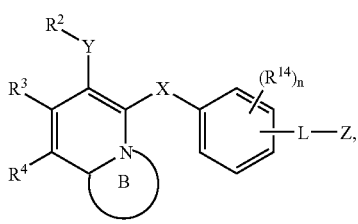

XXXXIII wherein X, Y, Z, L, $R^2$, $R^3$, $R^4$, $R^5$, $R^6$, $R^{14}$ and subscript n have the meanings and groupings provided above in formula VI. In formulas XXXXI, XXXXII and XXXXIII, structure B represents a fused 5- or 6-membered ring containing 0, 1, 2 or 3 heteroatoms selected from N, O and S. Optionally, structure B is substituted with halogen, $(C_1$-$C_3)$alkyl, halo$(C_1$-$C_3)$alkyl, cyclo$(C_3$-$C_5)$alkyl, cyclo$(C_3$-$C_5)$alkenyl, amino$(C_1$-$C_3)$alkyl, hydroxy, oxo, —OR', —CONR'R", —N(R")C(O)R', —CO$_2$R', —CN, aryl, or heteroaryl, wherein R' and R" are each independently hydrogen, $(C_1$-$C_6)$alkyl, cyclo$(C_3$-$C_8)$alkyl, cyclo$(C_3$-$C_8)$alkenyl, aryl or aryl$(C_1$-$C_4)$alkyl.

In some embodiments of formula XXXXI, XXXXII or XXXXIII, ring B is aromatic.

In certain embodiments, ring B is not aromatic.

Exemplary embodiments of the fused 5- or 6-membered ring formed by a pair of adjacent substituents of $R^3$ and $R^4$ or $R^4$ and $R^5$ in formula XXXX, for instance, structure B in formula XXXXI or XXXXII, include those described above with respect to formula II.

Exemplary embodiments of the fused 5- or 6-membered ring formed by a pair of adjacent substituents of $R^5$ and $R^6$ in formula XXXX, including, for example, structure B in formula XXXXIII, include those described above with regard to formulas VII or VIII.

In another aspect, the invention provides compounds of formula XXXXIV:

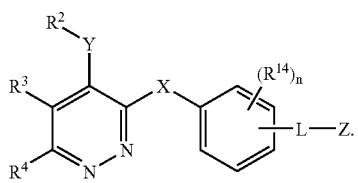

XXXXIV

In formula XXXXIV, the symbols X, Y, Z, L, $R^2$, $R^3$, $R^4$, $R^{14}$ and subscript n are as described above with regard to formula VI.

In certain embodiments, the fused 5- or 6-membered ring formed by a pair of adjacent substituents of $R^3$ and $R^4$ in formula XXXXIV, can be a compound having formula XXXXV:

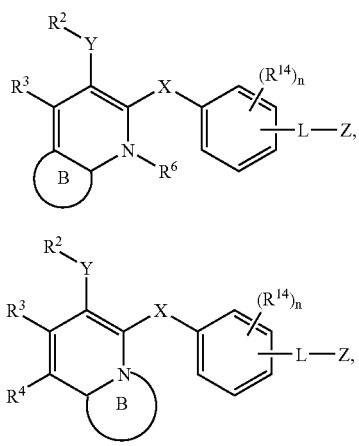

XXXXV wherein X, Y, Z, L, $R^{14}$ and subscript n have the meanings and groupings provided above in formula VI. In formula XXXXV, structure B represents a fused 5- or 6-membered ring containing 0, 1, 2 or 3 heteroatoms selected from N, O and S. Optionally, structure B is substituted with halogen, $(C_1$-$C_3)$alkyl, halo$(C_1$-$C_3)$alkyl, cyclo$(C_3$-$C_5)$alkyl, cyclo$(C_3$-$C_5)$alkenyl, amino$(C_1$-$C_3)$alkyl, hydroxy, oxo, —OR', —CONR'R", —N(R")C(O)R', —CO$_2$R', —CN, aryl, or heteroaryl, wherein R' and R" are each independently hydrogen, $(C_1$-$C_6)$alkyl, cyclo$(C_3$-$C_8)$alkyl, cyclo$(C_3$-$C_8)$alkenyl, aryl or aryl$(C_1$-$C_4)$alkyl.

In some embodiments of formula XXXXV, ring B is aromatic.

In certain embodiments, ring B is not aromatic.

Exemplary embodiments of the fused 5- or 6-membered ring formed by a pair of adjacent substituents of $R^3$ and $R^4$ in formula XXXXIV, for instance, structure B in formula XXXXV, include those described above with respect to formula II.

One of skill in the art will understand that a number of structural isomers are represented by formulas VI through XXXXV. For example, structural isomers a, b and c of formulas VI through XXXXV, where the dotted line represents the attachment to X in formulas VI through XXXXV, are:

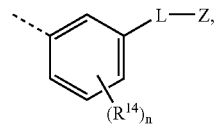

VIa, or
VIIa, or
VIIIa,
etc.

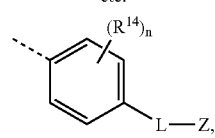

VIb, or
VIIb, or
VIIIb,
etc.

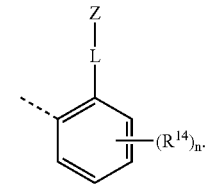

VIc, or
VIIc, or
VIIIc,
etc.

As stated above, in certain embodiments of any one of formula I through XXXXV, a $R^{14}$ group can be linked to L, or portion of L, to form a 5-, 6-, 7- or 8-membered fused ring containing from 0 to 3 heteroatoms selected from N, O and S. In some embodiments, the fused ring formed with the combination of a $R^{14}$ group linked to L can be aromatic. In other embodiments, the fused ring formed with the combination of a $R^{14}$ group linked to L is not aromatic. For example, embodiments where a $R^{14}$ group is linked to L to form a fused ring in any one of formula I through XXXXV, where the dotted line represents the attachment to X in formulas I through XXXXV, are:

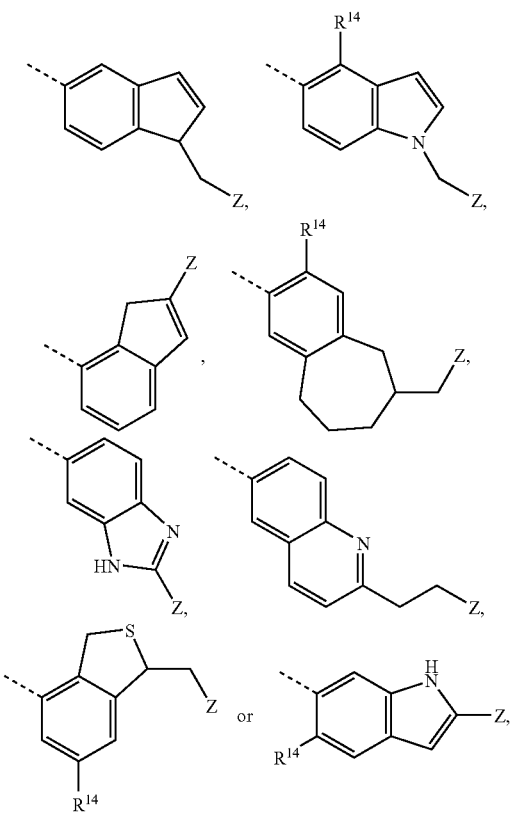

wherein Z and other $R^{14}$ groups, if present, are as defined above.

The compounds of formulas I-XXXXV include pharmaceutically acceptable salts, solvates or prodrugs thereof.

The invention encompasses novel compounds, novel pharmaceutical compositions and/or novel methods of use. While some compounds disclosed herein are available from commercial sources, the pharmaceutical compositions or methods of using these compounds are novel. Unless otherwise indicated, it is to be understood that the invention includes those compounds that are novel, as well as pharmaceutical compositions, various methods (e.g., methods of treating or preventing certain conditions and diseases mediated by CRTH2 and/or one or more other $PGD_2$ receptors), and the like which include both the novel compounds of the invention and compounds that are commercially available.

Preparation of the Compounds

The compounds of the invention can be prepared by a variety of synthetic or semisynthetic techniques. Exemplary synthesis routes to the compounds provided herein are described in FIG. 1 and in the Examples below. Synthesis of appropriate starting materials can be prepared by techniques known or apparent to those of skill in the art or the starting materials may be commercially available. For instance, such materials can be prepared according to the methods of U.S. Patent Application Publication No. 2004/0220237 A1 and International Publication No. WO 2004/058164, the contents of which are each hereby incorporated by reference in its entirety. One of skill in the art will understand that the synthetic routes can be modified to use different starting materials and/or alternate reagents to accomplish the desired transformations, and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group. Accordingly, the methods and reagents described herein are all expressed as non-limiting embodiments.

Compositions

In one aspect, the invention provides pharmaceutical compositions suitable for pharmaceutical use comprising one or more compounds of the invention and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

Formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of asthma, allergic diseases, inflammatory conditions and cancer and pathologies associated therewith (e.g., cardiovascular disease) or other adjuvant. In many instances, compositions which include a compounds of the invention and an alternative agent have additive or synergistic effects when administered.

Methods of Use

In another aspect, the invention provides methods of treating or preventing a disease or condition associated with CRTH2 and/or one or more other $PGD_2$ receptors by administering to a subject having such a condition or disease, a therapeutically effective amount of a compound or composition of the invention. In one group of embodiments, diseases and conditions, including chronic diseases of humans or other species, can be treated with modulators, or antagonists, of CRTH2 and/or one or more other $PGD_2$ receptors. These diseases and conditions include (1) inflammatory or allergic diseases such as systemic anaphylaxis and hypersensitivity disorders, atopic dermatitis, urticaria, drug allergies, insect sting allergies, food allergies (including celiac disease and the like) and mastocytosis, (2) inflammatory bowel diseases such as Crohn's disease, ulcerative colitis, ileitis and enteritis, (3) vasculitis, Behcet's syndrome, (4) psoriasis and inflammatory dermatoses such as dermatitis, eczema, atopic dermatitis, allergic contact dermatitis, urticaria, viral cutaneous pathologies such as those derived from human papillomavirus, HIV or RLV infection, bacterial, fungal and other parasital cutaneous pathologies, and cutaneous lupus erythematosus, (5) asthma and respiratory allergic diseases such as allergic asthma, allergic rhinitis, otitis media, allergic conjunctivitis, hypersensitivity lung diseases, chronic obstructive pulmonary disease and the like, (6) autoimmune diseases, such as arthritis (including rheumatoid and psoriatic), systemic lupus erythematosus, type I diabetes, myasthenia gravis, multiple sclerosis, Graves' disease, glomerulonephritis and the like, (7) graft rejection (including allograft rejection and graft-v-host disease), e.g., skin graft rejection, solid organ transplant rejection, bone marrow transplant rejection, (8) fever, (9) cardiovascular disorders such as acute heart failure, hypotension, hypertension, angina pectoris, myocardial infarction, cardiomyopathy, congestive heart failure, atherosclerosis, coronary artery disease, restenosis, thrombosis and vascular stenosis, (10) cerebrovascular disorders such as traumatic brain injury, stroke, ischemic reperfusion injury and aneurysm, (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, (12) fibrosis, connective tissue disease and sarcoidosis, (13) genital and reproductive conditions such as erectile dysfunction, (14) gastrointestinal disorders such as gastritis, ulcers, nausea, pancreatitis and vomiting; (15) neurologic disorders, such as Alzheimer's disease, (16) sleep disorders such as insomnia, narcolepsy, sleep apnea syndrome and Pickwick Syndrome, (17) pain, (18) renal disorders, (19) ocular disorders such as glaucoma, (20) infectious diseases, viral infections such as HIV, and bacterial infections such as sepsis, (21) inflammation, (22) flushing and (23) nasal congestion.

In yet another aspect, the invention provides methods of treating or preventing a disease or disorder mediated, regulated or influenced by Th2 cells, eosinophils, basophils, platelets, Langerhans cells, dendritic cells or mast cells, comprising administering to a subject having such as disease or disorder a therapeutically effective amount of one or more of the subject compounds or compositions.

In yet another aspect, the invention provides methods of treating or preventing a condition or disorder mediated, regulated or influenced by $PGD_2$ and metabolites thereof, such as 13,14-dihydro-15-keto-$PGD_2$ and 15-deoxy-$\Delta^{12,14}$-$PGD_2$, comprising administering to a subject having such as disease or disorder a therapeutically effective amount of one or more of the subject compounds or compositions.

In yet another aspect, the invention provides methods of treating or preventing a disease or disorder responsive to modulation of CRTH2 and/or one or more other $PGD_2$ receptors comprising administering to a subject having such a disease or disorder, a therapeutically effective amount of one or more of the subject compounds or compositions.

In yet another aspect, the invention provides methods of treating or preventing a disease or disorder mediated by CRTH2 and/or one or more other $PGD_2$ receptors comprising administering to a subject having such a condition or disease, a therapeutically effective amount of one or more of the subject compounds or compositions.

In yet another aspect, the invention provides methods of modulating CRTH2 and/or one or more other $PGD_2$ receptors comprising contacting a cell with one or more of the subject compounds or compositions.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention of inflammatory conditions, immune disorders, asthma, allergic rhinitis, eczema, psoriasis, atopic dermatitis, fever, sepsis, systemic lupus ertherma tosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion, urticaria or other conditions or disorders associated with CRTH2 and/or one or more other $PGD_2$ receptors, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion, urticaria and those pathologies noted above.

Such other agents, or drugs, may be administered, by a route and in an amount commonly used therefor, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of other therapeutic agents that may be combined with a compound of the invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, triamcinolone, dexamethasone, fluticasone, flunisolide and hydrocortisone, and corticosteroid analogs such as budesonide; (c) immunosuppressants such as cyclosporine (cyclosporine A, SANDIMMUNE®, NEORAL®), tacrolimus (FK-506, PROGRAF®), rapamycin (sirolimus, RAPAMUNE®) and other FK-506 type immunosuppressants, and mycophenolate, e.g., mycophenolate mofetil (CELLCEPT®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (ADVAIR®), formoterol-budesonid (SYMBICORT®)), theophylline, cromolyn, cromolyn sodium, nedocromil, atropine, ipratropium, ipratropium bromide, leukotriene antagonists (e.g., zafirlukast, montelukast, montelukast sodium (SINGULAIR®), pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (CELEBREX®) and rofecoxib (VIOXX®); (h) inhibitors of phosphodiesterase type IV (PDE-IV); (i) other $PGD_2$ receptor antagonists, especially DP antagonists; (j) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (k) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (l) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enalopril); (m) anti-diabetic agents such as insulin and insulin mimetics, sulfonylureas (e.g., glyburide, meglinatide), biguanides, e.g., metformin (GLUCOPHAGE®), α-glucosidase inhibitors (acarbose), thiazolidinone compounds, e.g., rosiglitazone (Avandia®), troglitazone (REZULIN®), ciglitazone, pioglitazone (ACTOS®) and englitazone; (n) preparations of interferon beta (interferon β-1α, interferon β-1β); (o) gold compounds such as auranofin and aurothioglucose, (p) TNF inhibitors, e.g., etanercept (ENBREL®), antibody therapies such as orthoclone (OKT3), daclizumab (ZENAPAX®), basiliximab (SIMULECT®), infliximab (REMICADE®) and D2E6 TNF antibody, (q) lubricants or emollients such as petrolatum and lanolin, keratolytic agents, vitamin $D_3$ derivatives (e.g., calcipotriene and calcipotriol (DOVONEX®)), PUVA, anthralin (DRITHROCREME®), etretinate (TEGISON®) and isotretinoin; (r) multiple sclerosis therapeutic agents such as interferon β-1β (BETASERON®), interferon β-1α (AVONEX®), azathioprine (IMUREK®, IMURAN®), glatiramer acetate (CAPOXONE®), a glucocorticoid (e.g., prednisolone) and cyclophosphamide; (s) other compounds such as 5-aminosalicylic acid and prodrugs thereof; (t) DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cytostatic agents, e.g., imatinib (STI571, GLEEVEC®) and rituximab (RITUXAN®). The weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, preferably about 200:1 to about 1:200. Combinations of a compound of the invention and other active ingredients will generally also be within the aforementioned range, but in each case, an effective dose of each active ingredient should be used.

Analysis of the Compounds

In yet another aspect, the invention includes methods to evaluate putative specific agonists or antagonists of CRTH2 and/or one or more other $PGD_2$ receptors. Accordingly, the invention is directed to the use of these compounds in the preparation and execution of screening assays for compounds which modulate the function of CRTH2 and/or one or more other $PGD_2$ receptors. For example, the compounds of this invention are useful for CRTH2 mutants and/or one or more other $PGD_2$ receptor mutants, which are excellent screening tools for potent compounds. Furthermore, the compounds of this invention are useful in establishing or determining the binding site of other compounds to CRTH2 and/or one or more other $PGD_2$ receptors, e.g., by competitive inhibition. The compounds of the instant invention are also useful for the evaluation of putative specific modulators of CRTH2 and/or one or more other $PGD_2$ receptors. One of skill in the art will appreciate that thorough evaluation of specific agonists and antagonists of $PGD_2$ receptors has been hampered by the lack of availability of non-peptidyl (metabolically resistant) compounds with high binding affinity for these receptors. The compounds provided herein are particularly useful in this context.

High Throughput Screening

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to the assays, which are typically run in parallel (e.g., in microtiter formats on microtiter plates in robotic assays). Preferred assays detect enhancement or inhibition of CRTH2 and/or one or more other $PGD_2$ receptors function.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start-up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

7. EXAMPLES

The following examples are offered by way of illustration and are not intended to limit the scope of the invention. Those of skill in the art will readily recognize a variety of noncritical parameters that could be modified to yield essentially similar results.

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

7.1. Example 1

This example illustrates the preparation of 2-(4-(4-(2,4-dichlorophenylsulfonamido)-2-methyl-1H-indol-5-yloxy)-3-methoxyphenyl)acetic acid (1).

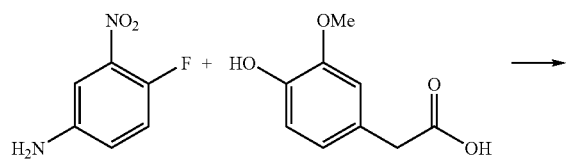

Scheme 1.1

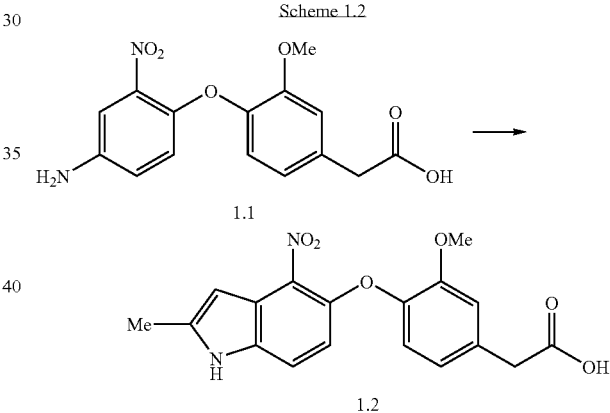

2-(4-(4-Amino-2-nitrophenoxy)-3-methoxyphenyl)acetic acid (1.1). A mixture of 4-fluoro-3-nitroaniline (3.45 g, 22.1 mmol), 4-hydroxy-3-methoxyphenylacetic acid (4.03 g, 22.1 mmol) and cesium carbonate (18.0 g, 55.3 mmol) in methylsulfoxide (40 mL) was heated to 120° C. (external temperature, oil bath) overnight. After 16 h the reaction was poured into water and the pH adjusted to <4 by addition of citric acid. The aqueous mixture was extracted twice with ethyl acetate. The combined organic extracts were washed with water then brine. The organic separation was stirred over magnesium sulfate, filtered and the filtrate concentrated in vacuo on a rotary evaporator to afford a dark brown oil. The product was isolated by chromatography on silica gel, eluting with an ethyl acetate/hexane gradient, to afford an orange foamy solid. LC-MS ESI (neg.) m/z: 317.0 (M−H). $^1$H NMR (400 MHz) (CDCl$_3$) δ 7.27 (d, J=8.4 Hz, 1H); 6.93 (s, 1H); 6.84-6.79 (m, 4H); 5.90 (br s, 2H); 3.85 (s, 31H); 3.63 (s, 2H) ppm.

Scheme 1.2

2-(3-Methoxy-4-(2-methyl-4-nitro-1H-indol-5-yloxy) phenyl)acetic acid (1.2). The reaction was carried out in a three-necked flask fitted with an overhead stirrer. To a room temperature solution of 1.1 (5.00 g, 15.7 mmol) and acetone (3.46 mL, 47.1 mmol) dissolved in methylsulfoxide (80 mL) was added solid potassium tert-butoxide (5.29 g, 47.1 mmol) all in one portion. The reaction mixture immediately turned intense purple, generated an exotherm and thickened, hindering thorough stirring. After ca. 1 h the reaction mixture thinned and the mixture was easily stirred. The reaction was stirred overnight at room temperature. After 16 h, HPLC indicated no 1.1 remained and the reaction mixture was poured into aqueous 10% hydrochloric acid solution (75 mL). The methylsulfoxide/water mixture was diluted with additional water (200 mL) and the dilution extracted with 2/1 diethyl ether/dichloromethane (v/v) (3×200 mL). The combined organic extracts were filtered through a pad of Celite then washed with water (2×250 mL) and brine (100 mL). The organic separation was stirred over magnesium sulfate, filtered and the filtrate concentrated in vacuo on a rotary evaporator to afford a dark orange oil. Upon suspension of the oil in ethyl acetate, an orange solid precipitated, which was collected by filtration. This solid was identified as the desired product 1.2 by LC-MS, HPLC and ¹H NMR (data below). Additional product was isolated from the filtrate by chromatography on silica gel, eluting with an ethyl acetate/hexane gradient, to afford an orange solid (9.1) that included the regioisomer of 1.2. LC-MS ESI (neg.) m/z: 355.1 (M−H). ¹H NMR (400 MHz) (d₆-DMSO) δ 12.35 (br s, 1H); 11.64 (s, 1H); 7.53 (dd, J=0.6 & 8.7 Hz, 1H); 7.06 (d, J=1.4 Hz, 1H); 6.84 (d, J=8.1 Hz, 1H); 6.81 (dd, J=1.6 & 8.1 Hz, 1H); 6.60 (d, J=8.7, 1H); 6.49 (s, 1H); 3.75 (s, 3H); 3.57 (s, 2H); 2.45 (s, 3H) ppm.

Scheme 1.3

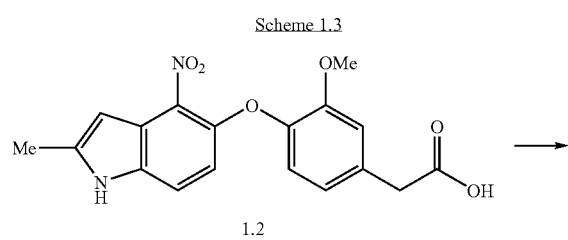

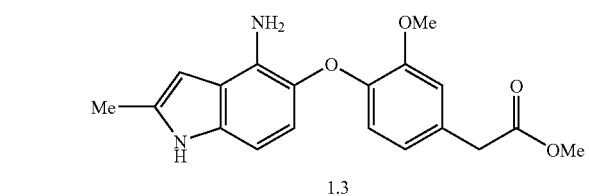

Methyl 2-(4-(4-amino-2-methyl-1H-indol-5-yloxy)-3-methoxyphenyl)acetate (1.3). A solution of 1.2 (1.00 g, 2.81 mmol) and tin chloride dihydrate (5.07 g, 22.5 mmol) dissolved in methanol (10 mL) was heated to 65° C. (external temperature, oil bath) overnight. The reaction solution was poured into aqueous 5% sodium bicarbonate solution and the resulting bi-phase passed through a pad of Celite, rinsing with water and ethyl acetate. The filtrate was separated and the organic layer washed with water and brine then stirred over magnesium sulfate, filtered and the filtrate concentrated in vacuo on a rotary evaporator to afford a yellow-green foamy solid. The product was isolated by chromatography on silica gel, eluting with ethyl acetate/hexane gradient, to afford a yellow foamy solid. LC-MS ESI (pos.) m/z: 341.2 (M+H).

Scheme 1.4

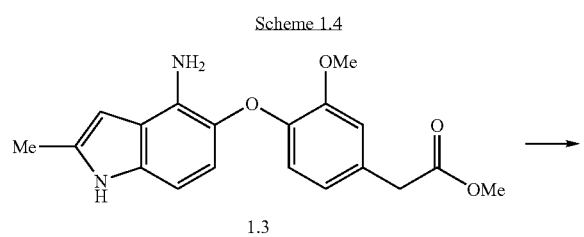

-continued

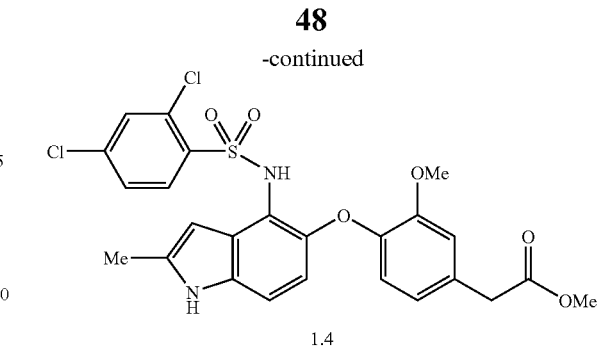

Methyl 2-(4-(4-(2,4-dichlorophenylsulfonamido)-2-methyl-1H-indol-5-yloxy)-3-methoxyphenyl)acetate (1.4). To a room temperature solution of 1.3 (2.22 g, 6.52 mmol) dissolved in pyridine (14 mL) was added 2,4-dichlorobenzenesulfonyl chloride (1.76 g, 7.17 mmol). The resulting red solution was stirred at room temperature for 30 min., after which time LC-MS indicated no 13 remained. The reaction solution was concentrated in vacuo on a rotary evaporator and the concentrate partitioned between ethyl acetate and saturated aqueous sodium bicarbonate solution. The organic separation was washed with water then brine. The organic extract was stirred over magnesium sulfate, filtered and the filtrate concentrated in vacuo on a rotary evaporator to afford an orange oil. The product was isolated by chromatography on silica gel, eluting with ethyl acetate/hexane gradient, to afford a faint yellow solid. LC-MS ESI (pos.) m/z: 549.0 (100%), 551.0 (68%), 550.0 (28%) (M+H).

Scheme 1.5

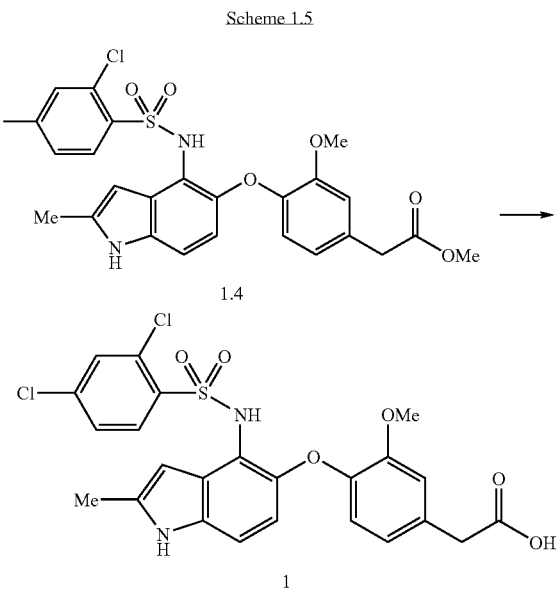

2-(4-(4-(2,4-Dichlorophenylsulfonamido)-2-methyl-1H-indol-5-yloxy)-3-methoxyphenyl)acetic acid (1). To a room temperature solution of 1.4 (1.00 g, 1.82 mmol) dissolved in a mixture of methanol (5 mL) and water (5 mL) was added lithium hydroxide (190 mg, 7.90 mmol). The reaction mixture was stirred at room temperature for 1 h then poured into aqueous 1N hydrochloric acid solution. The aqueous mixture was extracted twice with ethyl acetate. The combined organic extracts were washed twice with water then brine, stirred over magnesium sulfate, filtered and the filtrate concentrated in vacuo on a rotary evaporator to afford a yellow solid. The product was isolated by semi-preparative reversed phase HPLC to afford a colorless solid. LC-MS ESI (neg.) m/z: 533.0 (M−H). $^1$H NMR (400 MHz) (d$_6$-DMSO) δ 12.30 (br s, 1H); 10.95 (s, 1H); 9.73 (s, 1H); 7.63 (d, J=8.4 Hz, 1H); 7.52 (d, J=2 Hz, 1H); 7.30 (dd, J=2.0 & 8.5 Hz, 1H); 7.09 (d, J=8.6 Hz, 1H); 6.87 (d, J=1.4 Hz, 1H); 6.57 (d, J=8.3 Hz, 1H); 6.31 (d, J=8.6 Hz, 1H); 6.22 (d, J=8.0 Hz, 1H); 6.13 (s, 1H); 3.69 (s, 3H); 3.50 (s, 2H); 2.37 (s, 3H) ppm.

7.2. Example 2

This example illustrates the preparation of 2-(4-(3-Chloro-4-(2,4-dichlorophenylsulfonamido)-2-methyl-1H-indol-5-yloxy)-3-methoxyphenyl)acetic acid (2).

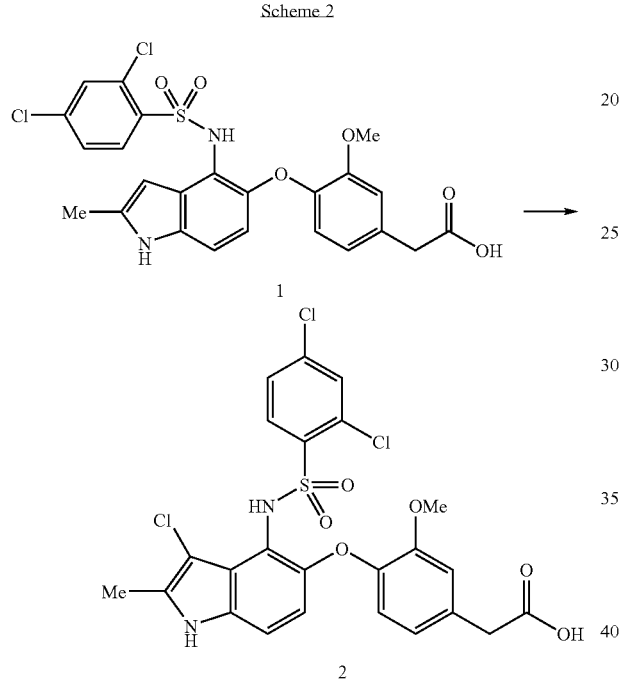

Scheme 2

2-(4-(3-Chloro-4-(2,4-dichlorophenylsulfonamido)-2-methyl-1H-indol-5-yloxy)-3-methoxyphenyl)acetic acid (2). A room temperature solution of 1 (14 mg, 0.026 mmol) and N-chlorosuccinimide (4 mg, 0.029 mmol) dissolved in N,N-dimethylformamide (1 mL) was stirred for 40 min., after which time HPLC indicated no 1 remained. The reaction was partitioned between ethyl acetate and 10% sodium thiosulfate aqueous solution. The organic separation was washed twice with water then brine. The organic layer was stirred over magnesium sulfate, filtered and the filtrate concentrated in vacuo on a rotary evaporator to afford a colorless solid. The product was isolated by semi-preparative reversed phase HPLC to afford a colorless solid. LC-MS ESI (neg.) m/z: 567.1 (M−H). $^1$H NMR (400 MHz) (d$_6$-DMSO) δ 11.41 (s, 1H); 9.66 (br s, 1H); 7.64 (d, J=8 Hz, 1H); 7.52 (s, 1H); 7.18 (d, J=8.0 Hz, 1H); 6.86 (s, 1H); 6.61 (d, J=8.0 Hz, 1H); 6.35 (d, J=8.0 Hz, 1H); 6.23 (d, J=8.0 Hz, 1H); 3.66 (s, 3H); 3.51 (s, 2H); 2.38 (s, 3H) ppm.

7.3. Example 3

This example illustrates the preparation of 2-(4-(4-(2,4-dichlorophenylsulfonamido)-1,2-dimethyl-1H-indol-5-yloxy)-3-methoxyphenyl)acetic acid (3).

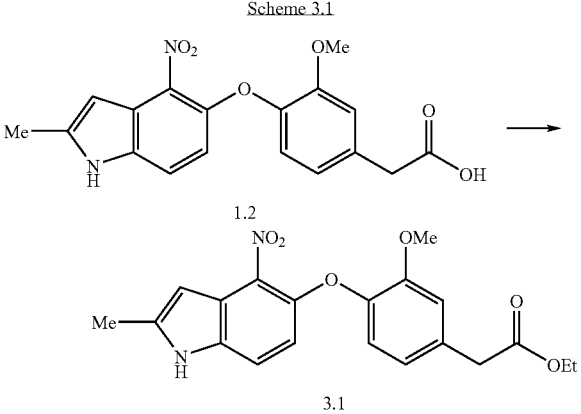

Scheme 3.1

Ethyl 2-(3-methoxy-4-(2-methyl-4-nitro-1H-indol-5-yloxy)phenyl)acetate (3.1). A solution of 1.2 (1.65 g, 4.63 mmol) in ethanol (20 mL) with several drops of concentrated sulfuric acid was heated to reflux overnight. After 16 h, HPLC indicated that no 1.2 remained and the ethanol was removed in vacuo on a rotary evaporator. The concentrate was partitioned between ethyl acetate and saturated aqueous sodium bicarbonate solution. The separated organic layer was washed with water then brine, stirred over magnesium sulfate, filtered and the filtrate concentrated in vacuo on a rotary evaporator to afford a dark oil. The desired product was isolated by trituration of the residue with ethyl acetate to yield the desired product as an orange solid. The filtrate from trituration was chromatographed on silica gel, eluting with an ethyl acetate/hexane gradient, to afford additional product. LC-MS ESI (pos.) m/z: 385.0 (M+H).

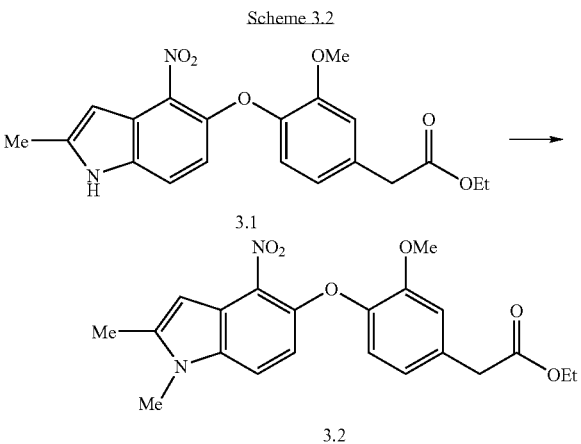

Scheme 3.2

Ethyl 2-(4-(1,2-dimethyl-4-nitro-1H-indol-5-yloxy)-3-methoxyphenyl)acetate (3.2). To a room temperature solution of 3.1 (38 mg, 0.099 mmol) and iodomethane (6.8 μL, 0.11 mmol) dissolved in N,N-dimethylformamide (1 mL) was added cesium carbonate (35 mg, 0.11 mmol). The resulting intense red solution was stirred at room temperature overnight. After 19 h, the color had dissipated to a faint pink and HPLC indicated no 3.1 remained. Several drops of aqueous 20% citric acid solution were added and the mixture partitioned between ethyl acetate and water. The separated aqueous layer was extracted again with ethyl acetate. The combined organic extracts were washed with water twice then brine. The organic separation was stirred over magnesium sulfate, filtered and the filtrate concentrated in vacuo on a rotary evaporator to afford a yellow solid. The product was used without further purification. $^1$H NMR (400 MHz) (CDCl$_3$) δ 7.35 (d, J=8.8 Hz, 1H); 6.95 (s, 1H); 6.83-6.76 (m, 3H); 6.71 (s, 1H); 4.16 (q, J=9.6 Hz, 2H); 3.88 (s, 3H); 3.70 (s, 3H); 2.48 (s, 3H); 1.27 (t, J=9.6 Hz, 3H) ppm.

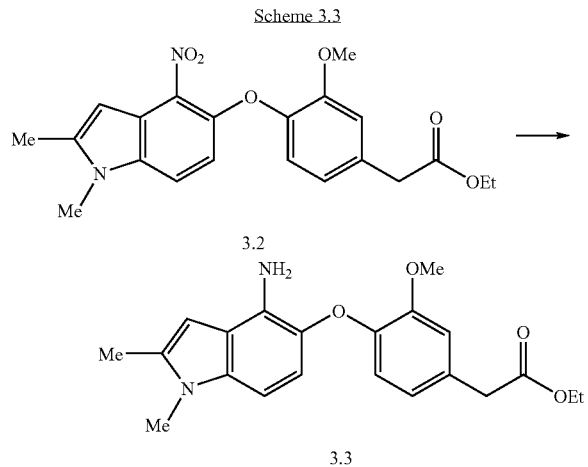

Ethyl 2-(4-(4-amino-1,2-dimethyl-1H-indol-5-yloxy)-3-methoxyphenyl)acetate (3.3). A solution of 3.2 (35 mg, 0.088 mmol) and tin chloride dihydrate (159 mg, 0.70 mmol) dissolved in ethyl acetate (5 mL) was heated to 80° C. overnight. Alter 18 h, HPLC indicated no 3.2 remained and the reaction was poured into aqueous 5% hydrochloric acid solution. The resulting emulsion was filtered through a pad of Celite to remove fine solids, rinsing the solids with ethyl acetate and water. The biphasic filtrate was separated and the organic layer washed with saturated aqueous sodium bicarbonate solution, water and brine. The organic separation was stirred over magnesium sulfate, filtered and the filtrate concentrated in vacuo on a rotary evaporator to afford a dark brown, foamy solid.

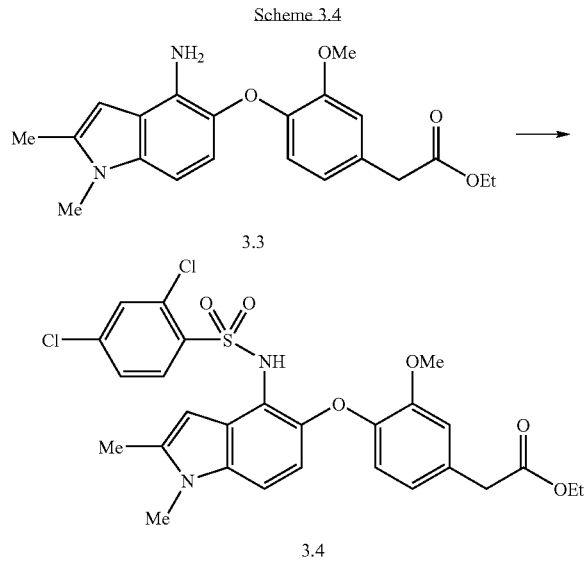

Ethyl 2-(4-(4-(2,4-dichlorophenylsulfonamido)-1,2-dimethyl-1H-indol-5-yloxy)-3-methoxyphenyl)acetate (3.4). To a room temperature solution of 3.3 (29 mg, 0.079 mmol) dissolved in pyridine (2 mL) was added 2,4-dichlorobenzenesulfonyl chloride (21 mg, 0.087 mmol). The resulting red solution was stirred at room temperature for 2 h, after which time HPLC indicated no 3.3 remained. The reaction solution was concentrated in vacuo on a rotary evaporator and the concentrate partitioned between ethyl acetate and saturated aqueous sodium bicarbonate solution. The organic separation was washed with water then brine. The organic extract was stirred over magnesium sulfate, filtered and the filtrate concentrated in vacuo on a rotary evaporator to afford an orange oil. The product was isolated by chromatography on silica gel, eluting with an ethyl acetate/hexane gradient, to afford a faint yellow oil. $^1$H NMR (500 MHz) (CDCl$_3$) δ 7.71 (d, J=8.4 Hz, 1H); 7.48 (s, 1H); 7.04 (d, J=8.8 Hz, 1H); 6.88 (d, J=1.8 Hz, 1H); 6.70 (s, 1H); 6.59 (d, J=8.7 Hz, 1H); 6.53 (d, J=6.4 Hz, 1H); 6.52 (d, J=1.8 Hz, 1H); 6.16 (d, J=8.2 Hz, 1H); 4.19 (q, J=7.1 Hz, 2H); 3.86 (s, 3H); 3.64 (s, 3H); 3.59 (s, 2H); 2.48 (s, 3H) ppm.

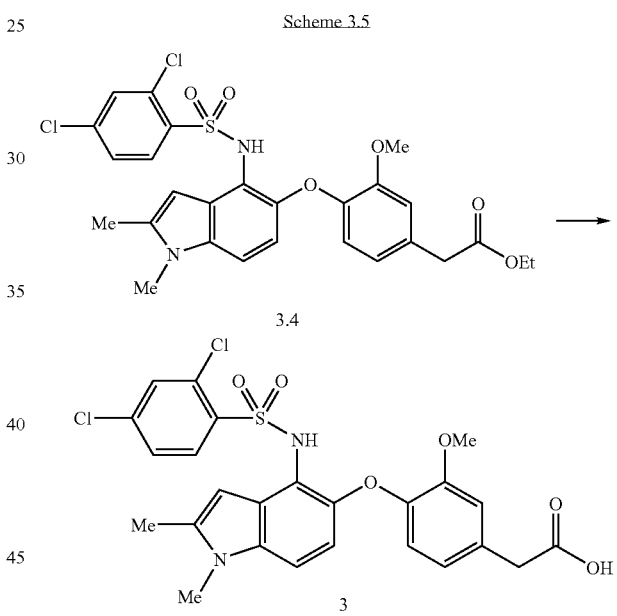

2-(4-(4-(2,4-Dichlorophenylsulfonamido)-1,2-dimethyl-1H-indol-5-yloxy)-3-methoxyphenyl)acetic acid (3). To a room temperature solution of 3.4 (25 mg, 0.043 mmol) dissolved in a mixture of tetrahydrofuran (2 mL) and methanol (1 mL) was added a solution of lithium hydroxide (50 mg, 2.1 mmol) dissolved in water (1 mL). The reaction was stirred at room temperature for 1 h then poured into aqueous 1N hydrochloric acid solution. The aqueous mixture was extracted twice with ethyl acetate. The combined organic extracts were washed twice with water then brine, stirred over magnesium sulfate, filtered and the filtrate concentrated in vacuo on a rotary evaporator to afford a colorless solid. LC-MS ESI (neg.) m/z: 547.0 (M−H). $^1$H NMR (400 MHz) (d$_6$-DMSO) δ 12.30 (br s, 1H); 9.80 (br s, 1H); 7.63 (d, J=8.8 Hz, 1H); 7.53 (d, J=2.0 Hz, 1H); 7.31 (dd, J=2.4 & 8.8 Hz, 1H); 7.22 (d, J=8.8 Hz, 1H); 6.89 (d, J=1.6 Hz, 1H); 6.59 (d, J=1.6 Hz, 1H); 6.39 (d, J=8.8 Hz, 1H); 6.23 (dd, J=3.6 & 3.6 Hz, 1H); 3.70 (s, 3H); 3.63 (s, 3H); 3.52 (s, 2H); 2.41 (s, 3H) ppm.

7.4. Example 4

This example illustrates the preparation of 2-(4-(2-tert-butyl-4-(2,4-dichlorophenylsulfonamido)-1H-indol-5-yloxy)-3-fluorophenyl)acetic acid (4).

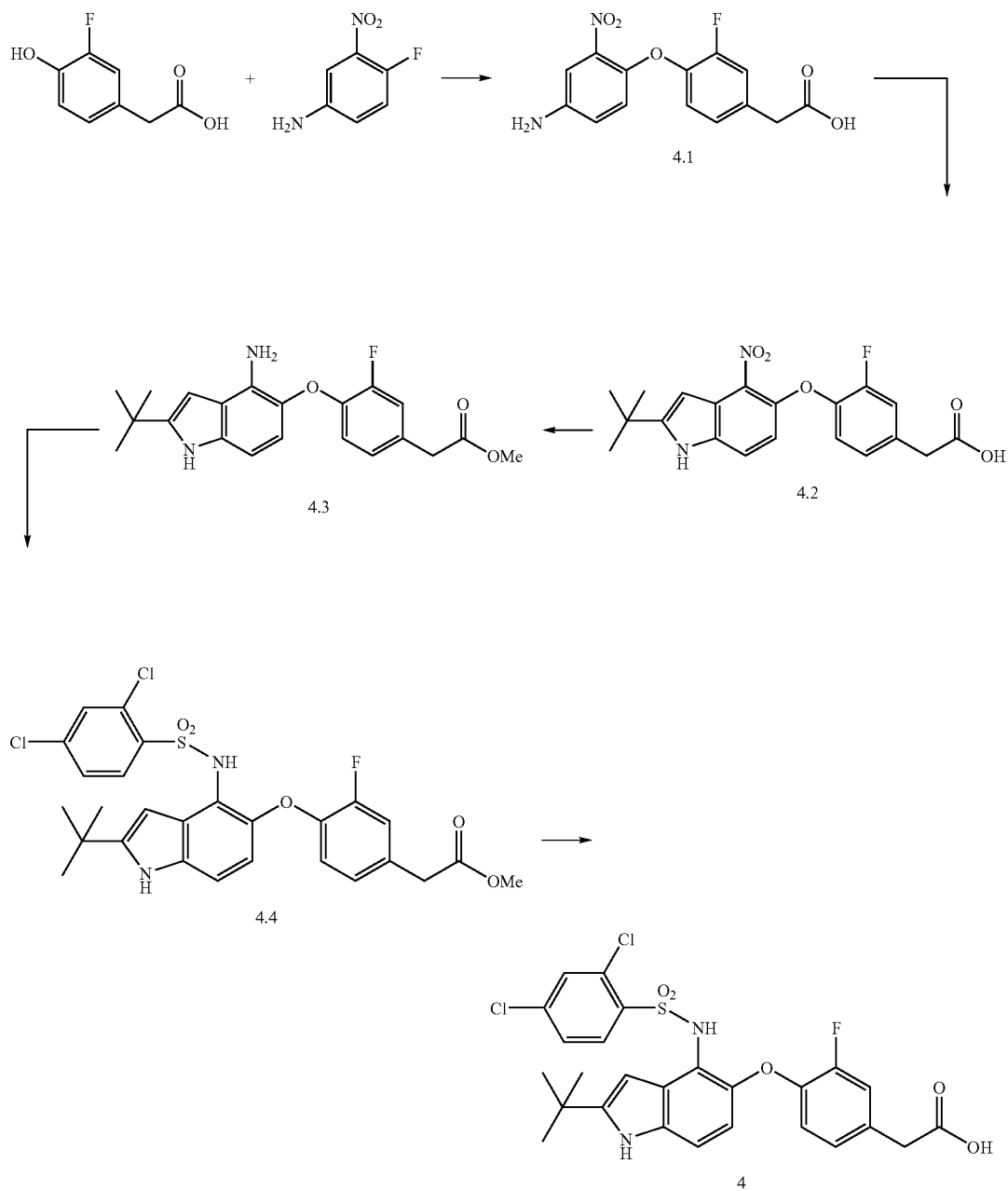

Scheme 4

2-(4-(2-tert-Butyl-4-(2,4-dichlorophenylsulfonamido)-1H-indol-5-yloxy)-3-fluorophenyl)acetic acid (4). The title compound was prepared according to the procedure of Example 1. LC-MS ESI (pos.) m/z: 565.0 (M+H). $^1$H NMR (500 MHz) (MeOD-$d_4$) δ 7.59 (d, J=8.5 Hz, 1H); 7.21 (d, J=1.9, 1H); 7.10 (dd, J=8.5, 2.0 Hz, 1H); 7.07 (d, J=8.6 Hz, 1H); 6.95 (dd, J=11.9, 1.9 Hz, 1H); 6.66 (d, J=8.3 Hz, 1H); 6.42 (d, J=8.6 Hz, 1H); 6.26 (dd, J=8.5, 8.5 Hz, 1H); 6.18 (s, 1H); 3.45 (s, 2H); 1.29 (s, 9H).

7.5. Example 5

This example illustrates the preparation of 2-(4-(2-cyclopropyl-4-(2,4-dichlorophenylsulfonamido)-1H-indol-5-yloxy)-3-methoxyphenyl)acetic acid (5).

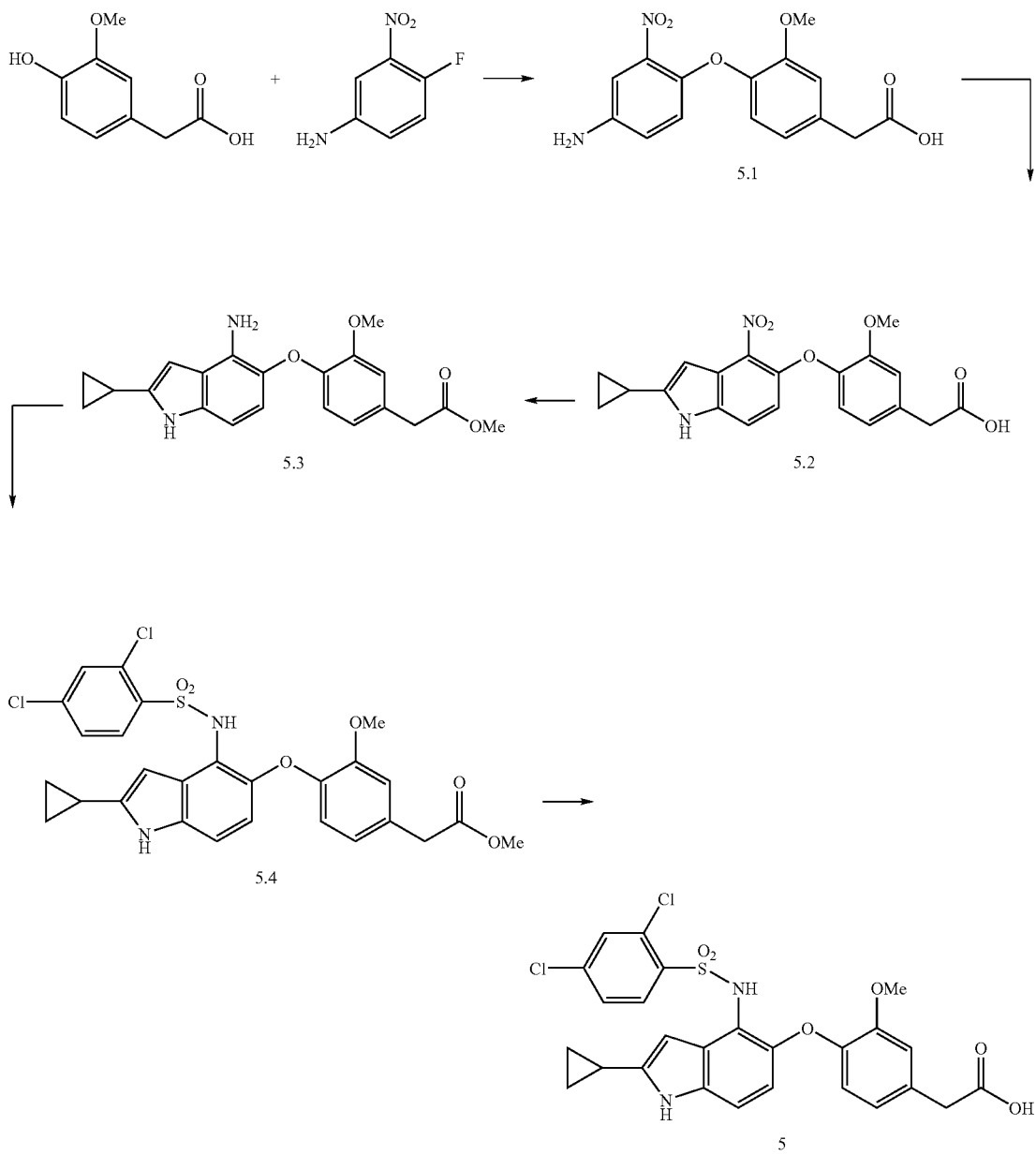

Scheme 5

2-(4-(2-Cyclopropyl-4-(2,4-dichlorophenylsulfonamido)-1H-indol-5-yloxy)-3-methoxyphenyl)acetic acid (5). The title compound was prepared according to the procedure of Example 1. LC-MS ESI (pos.) m/z: 561.0 (M+H). $^1$H NMR (500 MHz) (MeOD-$d_4$) δ 7.67 (d, J=8.5 Hz, 1H); 7.29 (d, J=2.0, 1H); 7.20 (dd, J=8.5, 2.0 Hz, 1H); 7.08 (d, J=8.6, 1H); 6.94 (d, J=1.7, 1H); 6.60 (dd, J=8.2, 1.7 Hz, 1H); 6.43 (d, J=8.7 Hz, 1H); 6.30 (s, 1H); 6.24 (d, J=8.2 Hz, 1H); 3.81 (s, 3H); 3.57 (s, 2H); 2.06-2.01 (m, 1H); 1.05-1.01 (m, 2H); 0.85-0.81 (m, 2H).

7.6. Example 6

This example illustrates the preparation of 2-(6-(4-(2,4-dichlorophenylsulfonamido)-2-methyl-1H-indol-5-yloxy)benzofuran-3-yl)acetic acid (6)

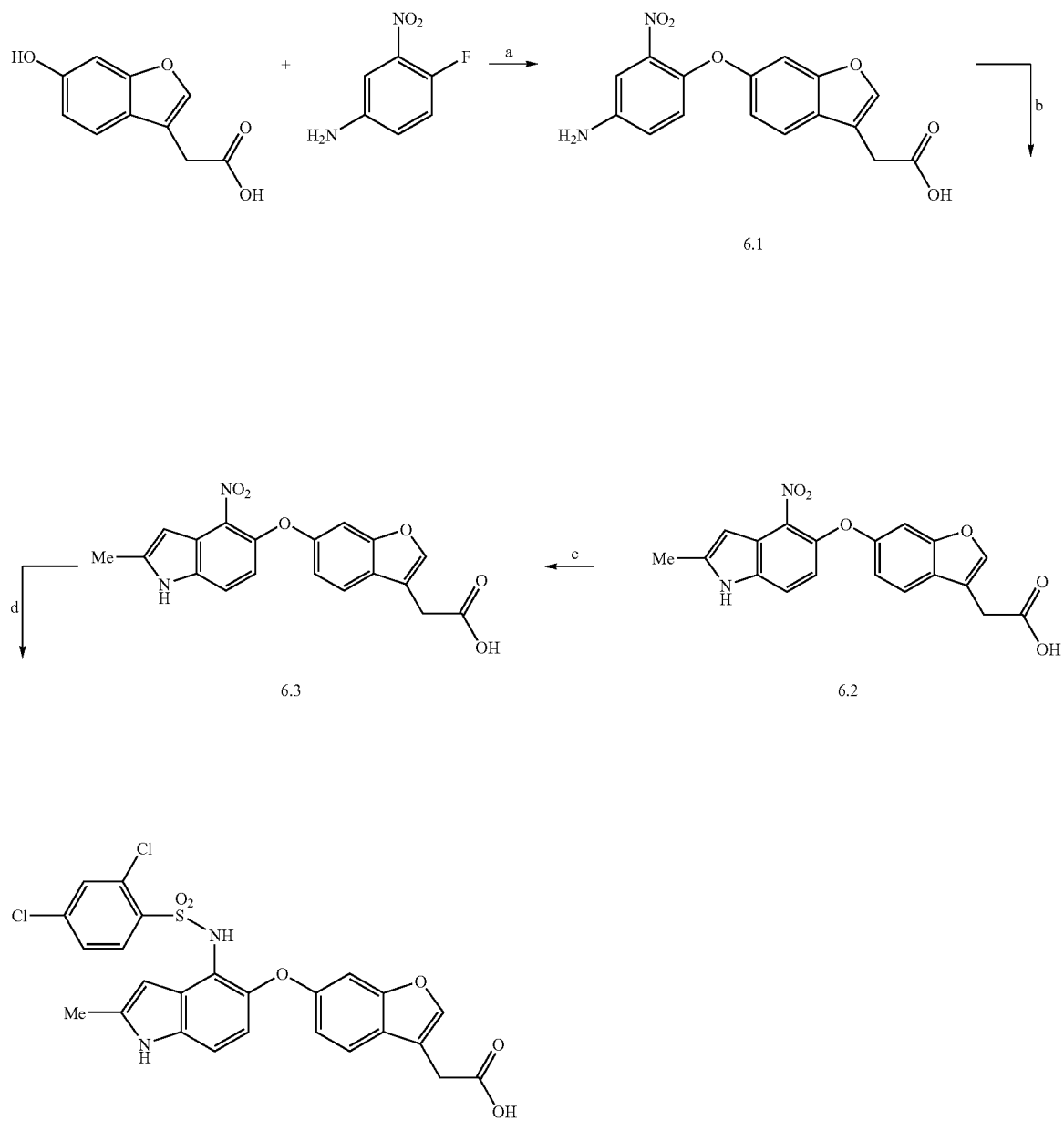

Scheme 6

2-(6-(4-(2,4-Dichlorophenylsulfonamido)-2-methyl-1H-indol-5-yloxy)benzofuran-3-yl)acetic acid (6). The title compound was prepared according to the procedure of Example 1. LC-MS ESI (pos.) m/z: 563.0 (M+H). $^1$H NMR (500 MHz) (DMSO-$d_6$) δ 12.47 (brs, 1H); 10.99 (s, 1H); 9.87 (s, 1H); 7.78 (s, 1H); 7.66 (d, J=8.8 Hz, 1H); 7.38-7.36 (m, 2H); 7.29 (dd, J=8.5, 1.4 Hz, 1H); 7.17 (d, J=8.6 Hz, 1H); 6.53-6.49 (m, 3H); 6.18 (s, 1H); 3.65 (s, 2H), 2.39 (s, 3H).

7.7. Example 7

This example illustrates the preparation of 2-(3-chloro-4-(4-(2,4-dichlorophenylsulfonamido)-2-propyl-1H-indol-5-yloxy)phenyl)acetic acid (7).

Scheme 7.1

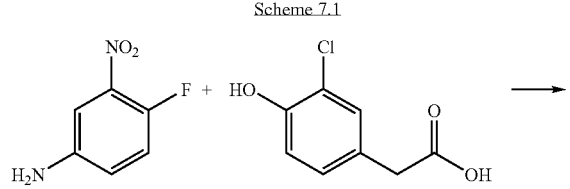

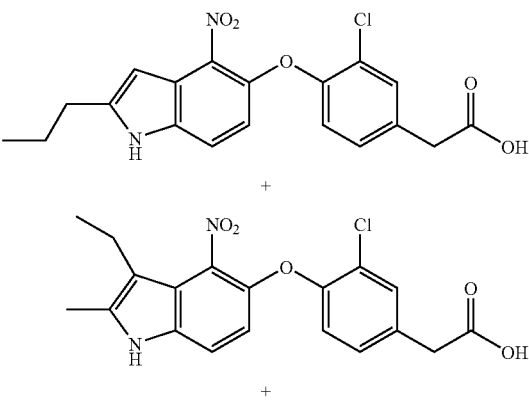

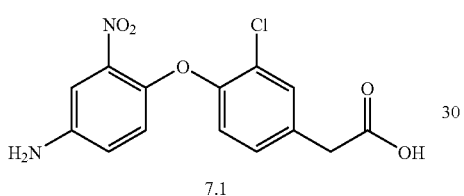

7.1

2-(4-(4-Amino-2-nitrophenoxy)-3-chlorophenyl)acetic acid (7.1). A mixture of 4-fluoro-3-nitroaniline (8.37 g, 53.6 mmol), 3-hydroxy-4-chlorophenylacetic acid (10.0 g, 53.6 mmol) and cesium carbonate (43.7 g, 134 mmol) in methylsulfoxide (100 mL) was heated to 80° C. (external temperature, oil bath) overnight. After 16 h, the reaction was poured into water and the pH adjusted to <4 by addition of 1N hydrochloric acid. The aqueous mixture was extracted twice with ethyl acetate. The combined organic extracts were washed with water then brine. The organic separation was stirred over magnesium sulfate, filtered and the filtrate concentrated in vacuo on a rotary evaporator to afford a dark brown oil. The product was isolated by chromatography on silica gel, eluting with an ethyl acetate/hexane gradient, to afford an orange foamy solid. LC-MS ESI (pos.) m/z: 323.0 (M+H).

Scheme 7.2

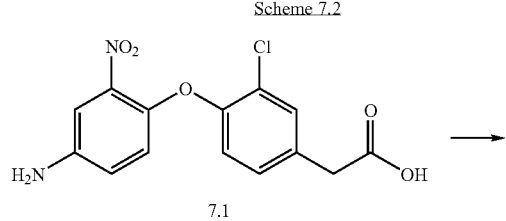

7.1

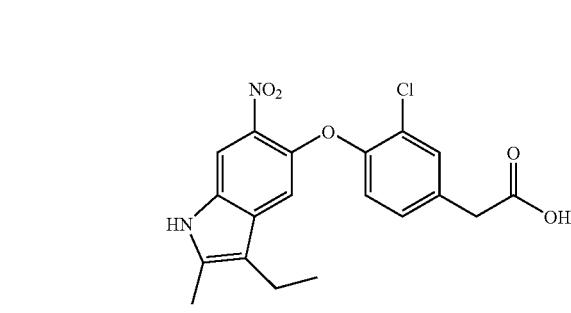

7.2

2-(3-Chloro-4-(4-nitro-2-propyl-1H-indol-5-yloxy)phenyl)acetic acid, 2-(3-chloro-4-(3-ethyl-2-methyl-4-nitro-1H-indol-5-yloxy)phenyl)acetic acid and 2-(3-chloro-4-(3-ethyl-2-methyl-6-nitro-1H-indol-5-yloxy)phenyl)acetic acid (7.2). To a room temperature solution of 7.1 (1.50 g, 4.65 mmol) and 2-pentanone (1.49 mL, 13.9 mmol) dissolved in methylsulfoxide (10 mL) was added solid potassium tert-butoxide (1.56 g, 13.9 mmol) all in one portion. The reaction mixture immediately turned intense purple and generated an exotherm. After 1 h, HPLC indicated no 7.1 remained and the reaction mixture was poured into water. The solution was acidified to pH<4 with solid citric acid and subsequently extracted three times with ethyl acetate (v/v) (3×200 mL). The combined organic extracts were washed with water (2×250 mL) and brine (100 mL). The organic separation was stirred over magnesium sulfate, filtered and the filtrate concentrated in vacuo on a rotary evaporator to afford the product mixture as a dark orange oil. Chromatography on silica gel, eluting with a methanol/dichloromethane gradient, afforded a brown solid containing all three regioisomers. LC-MS ESI (pos.) m/z: 389.0 (M+H).

Scheme 7.3

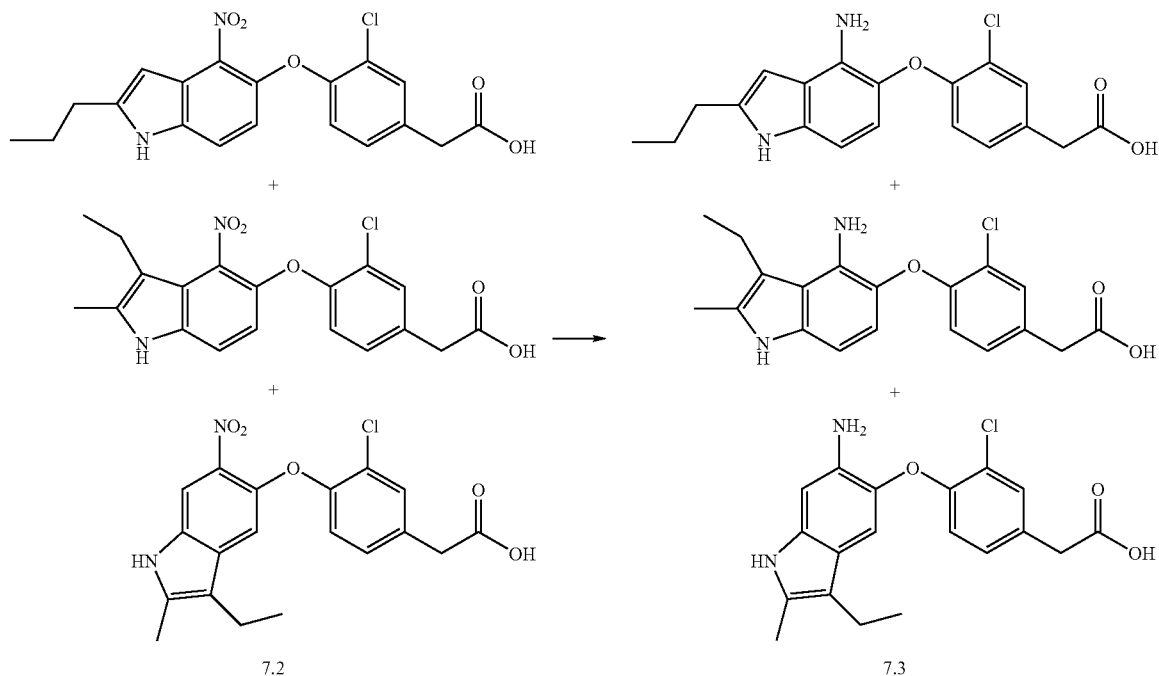

7.2            7.3

2-(4-(4-Amino-2-propyl-1H-indol-5-yloxy)-3-chlorophenyl)acetic acid, 2-(4-(4-amino-3-ethyl-2-methyl-1H-indol-5-yloxy)-3-chlorophenyl)acetic acid and 2-(4-(6-amino-3-ethyl-2-methyl-1H-indol-5-yloxy)-3-chlorophenyl)acetic acid (7.3). A solution of the mixture of regioisomers 7.2 (1.30 g, 3.34 mmol) and tin chloride dihydrate 3.02 g, 13.4 mmol) dissolved in ethyl acetate (10 mL) was heated to 90° C. (external temperature, oil bath) in a capped vial overnight. The reaction solution was poured into aqueous 1N sodium hydroxide solution and the resulting bi-phase passed through a pad of Celite, rinsing with water and ethyl acetate. The filtrate was acidified to pH<4 with 1N hydrochloric acid solution and the organic layer separated and washed with water and brine then stirred over magnesium sulfate, filtered and the filtrate concentrated in vacuo on a rotary evaporator. The regioisomers were isolated by semi-preparative reversed phase HPLC to afford regioisomer A as a brown solid and regioisomer B as a brown solid and regioisomer C as a brown solid. LC-MS ESI (pos.) m/z: 359.0 (M+H).

Scheme 7.4

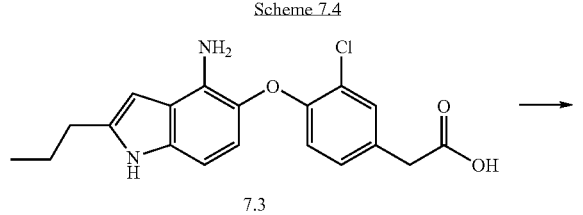

7.3

-continued

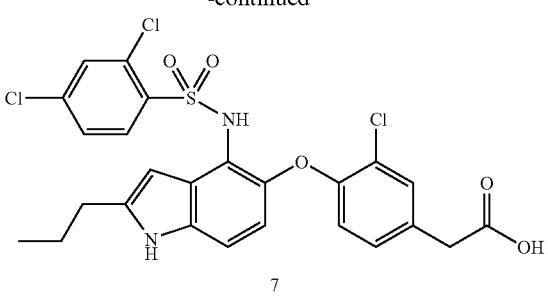

7

2-(3-Chloro-4-(4-(2,4-dichlorophenylsulfonamido)-2-propyl-1H-indol-5-yloxy)phenyl)acetic acid (7). To a room temperature solution of 7.3 regioisomer A (31 mg, 86.4 µmol) dissolved in pyridine (1 mL) was added 2,4-dichlorobenzenesulfonyl chloride (23 mg, 95.0 µmol). The resulting red solution was stirred at room temperature for 30 min., after which time LC-MS indicated no 7.3 regioisomer A remained. The reaction solution was concentrated in vacuo on a rotary evaporator and the concentrate partitioned between ethyl acetate and water. The aqueous mixture acidified with a 1N hydrochloric acid solution and subsequently extracted twice with ethyl acetate. The organic separation was washed with brine. The organic extract was stirred over magnesium sulfate, filtered and the filtrate concentrated in vacuo on a rotary evaporator to afford the product mixture as an orange oil. The product was isolated by semi-preparative reversed phase HPLC to afford G as a colorless solid. LC-MS ESI (pos.) m/z: 569.0 (M+H). $^1$H NMR (500 MHz) (MeOD-d$_4$) δ 7.67 (d, J=8.5 Hz, 1H); 7.33-7.31 (m, 2H); 7.17 (d, J=8.6 Hz, 2H); 6.91 (d, J=8.6 Hz, 1H); 6.47 (d, J=8.6 Hz, 1H); 6.39 (s, 1H); 6.29 (d, J=8.4 Hz, 1H); 3.54 (s, 2H); 2.77 (t, J=7.4 Hz, 2H); 1.82-1.76 (m, 2H); 1.05 (t, J=7.4 Hz, 3H).

7.8. Example 8

This example illustrates the preparation of 2-(3-chloro-4-(6-(2,4-dichlorophenylsulfonamido)-3-ethyl-2-methyl-1H-indol-5-yloxy)phenyl)acetic acid (8).

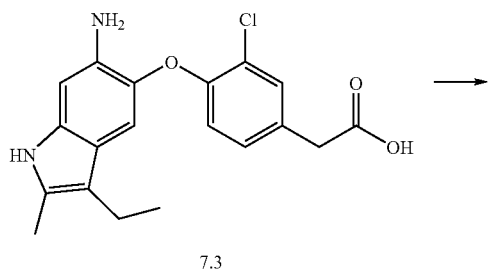

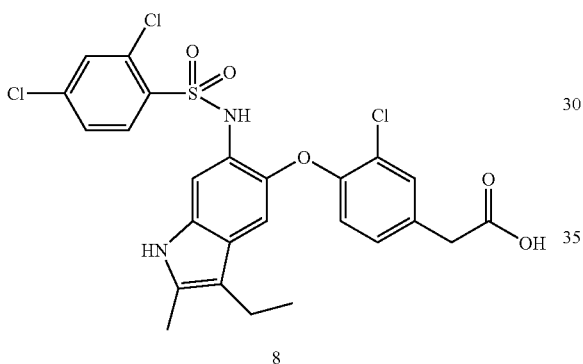

2-(3-Chloro-4-(6-(2,4-dichlorophenylsulfonamido)-3-ethyl-2-methyl-1H-indol-5-yloxy)phenyl)acetic acid (8). To a room temperature solution of 7.3 regioisomer B (50 mg, 139 μmol) prepared according to the procedure of Example 7 and dissolved in pyridine (1 mL) was added 2,4-dichlorobenzenesulfonyl chloride (38 mg, 153 μmol). The resulting red solution was stirred at room temperature for 30 min., after which time LC-MS indicated no 7.3 regioisomer B remained. The reaction solution was concentrated in vacuo on a rotary evaporator and the concentrate partitioned between ethyl acetate and water. The aqueous mixture acidified with a 1N hydrochloric acid solution and subsequently extracted twice with ethyl acetate. The organic separation was washed with brine. The organic extract was stirred over magnesium sulfate, filtered and the filtrate concentrated in vacuo on a rotary evaporator to afford an orange oil. The product was isolated by semi-preparative reversed phase HPLC to afford 8 as a colorless solid. LC-MS ESI (pos.) m/z: 569.0 (M+H).

$^1$H NMR (500 MHz) (MeOD-d$_4$) δ 7.67 (d, J=8.5 Hz, 1H); 7.33-7.31 (m, 2H); 7.17 (d, J=8.6 Hz, 2H); 6.91 (d, J=8.6 Hz, 1H); 6.47 (d, J=8.6 Hz, 1H); 6.39 (s, 1H); 6.29 (d, J=8.4 Hz, 1H); 3.54 (s, 2H); 2.77 (t, J=7.4 Hz, 2H); 1.82-1.76 (m, 2H); 1.05 (t, J=7.4 Hz, 3H).

7.9. Example 9

This example illustrates the preparation of 2-(4-(6-(2,4-dichlorophenylsulfonamido)-2-methyl-1H-indol-5-yloxy)-3-methoxyphenyl)acetic acid (9).

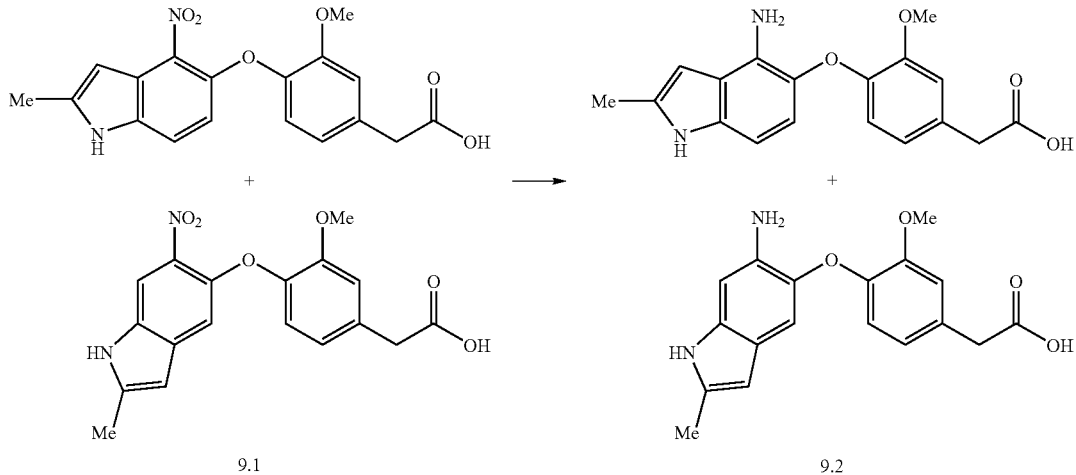

Methyl 2-(4-(4-amino-2-methyl-1H-indol-5-yloxy)-3-methoxyphenyl)acetic acid and Methyl 2-(4-(6-amino-2-methyl-1H-indol-5-yloxy)-3-methoxyphenyl)acetic acid (9.2). A solution of 9.1 (0.80 g, 2.25 mmol) and tin chloride dihydrate (4.05 g, 17.9 mmol) dissolved in ethyl acetate (20 mL) was heated to 90° C. (external temperature, oil bath) in a capped vial overnight. The reaction solution was poured into aqueous 1N sodium hydroxide solution and the resulting bi-phase passed through a pad of Celite, rinsing with water and ethyl acetate. The filtrate was acidified to pH<4 with 1N hydrochloric acid solution and the organic layer separated and washed with water and brine then stirred over magnesium sulfate, filtered and the filtrate concentrated in vacuo on a rotary evaporator. A mixture of the ethyl esterified product and the acid product was hydrolyzed for both regioisomers: To a solution of the residue dissolved in methanol (1 mL) and water (1 mL) was added lithium hydroxide (0.23 g, 5.63 mmol). The reaction mixture was stirred at room temperature for 1 h then poured into aqueous 1N hydrochloric acid solution. The aqueous mixture was extracted twice with ethyl acetate. The combined organic extracts were washed twice with water then brine, stirred over magnesium sulfate, filtered and the filtrate concentrated in vacuo on a rotary evaporator to afford a yellow solid. The product was isolated by chromatography on silica gel, eluting with methanol/dichloromethane gradient, to afford a yellow solid. Both regioisomers were obtained and carried through to the next step as a mixture. LC-MS ESI (pos.) m/z: 327.1 (M+H).

2-(4-(4-(2,4-Dichlorophenylsulfonamido)-2-methyl-1H-indol-5-yloxy)-3-methoxyphenyl)acetic acid (1) and 2-(4-(6-(2,4-dichlorophenylsulfonamido)-2-methyl-1H-indol-5-yloxy)-3-methoxyphenyl)acetic acid (9). To a room temperature solution of 9.2 (419 mg, 1.28 mmol) dissolved in pyridine (5 mL) was added 2,4-dichlorobenzenesulfonyl chloride (347 mg, 1.41 mmol). The resulting red solution was stirred at room temperature for 30 min., after which time LC-MS indicated no 9.2 remained. The reaction solution was concentrated in vacuo on a rotary evaporator and the concentrate partitioned between ethyl acetate and water. The aqueous mixture acidified with a 1N hydrochloric acid solution and subsequently extracted twice with ethyl acetate. The organic separation was washed with brine. The combined organic extracts was stirred over magnesium sulfate, filtered and the filtrate concentrated in vacuo on a rotary evaporator to afford an orange oil. The mixture of regioisomers was separated by semi-preparative reversed phase HPLC to afford regioisomer A (1) as a colorless solid and regioisomer B (9) as a colorless solid. LC-MS ESI (pos.) m/z: 535.0 (M+H). $^1$H NMR (500 MHz) (MeOD-d$_4$) δ 7.67 (d, J=8.5 Hz, 1H); 7.52 (d, J=2.1 Hz, 1H); 7.20 (dd, J=8.5, 2.1 Hz, 1H); 6.94 (s, 1H); 6.70 (s, 2H); 6.56 (d, J=8.3 Hz, 1H); 6.11 (s, 1H); 6.03 (d, J=8.3 Hz, 1H); 3.66 (s, 3H); 3.47 (s, 2H); 2.25 (s, 3H).

7.10. Example 10

This example illustrates the preparation of 2-(4-(4-(2-chloro-4-propylphenylsulfonamido)-2-methyl-1H-indol-5-yloxy)-3-methoxyphenyl)acetic acid (10).

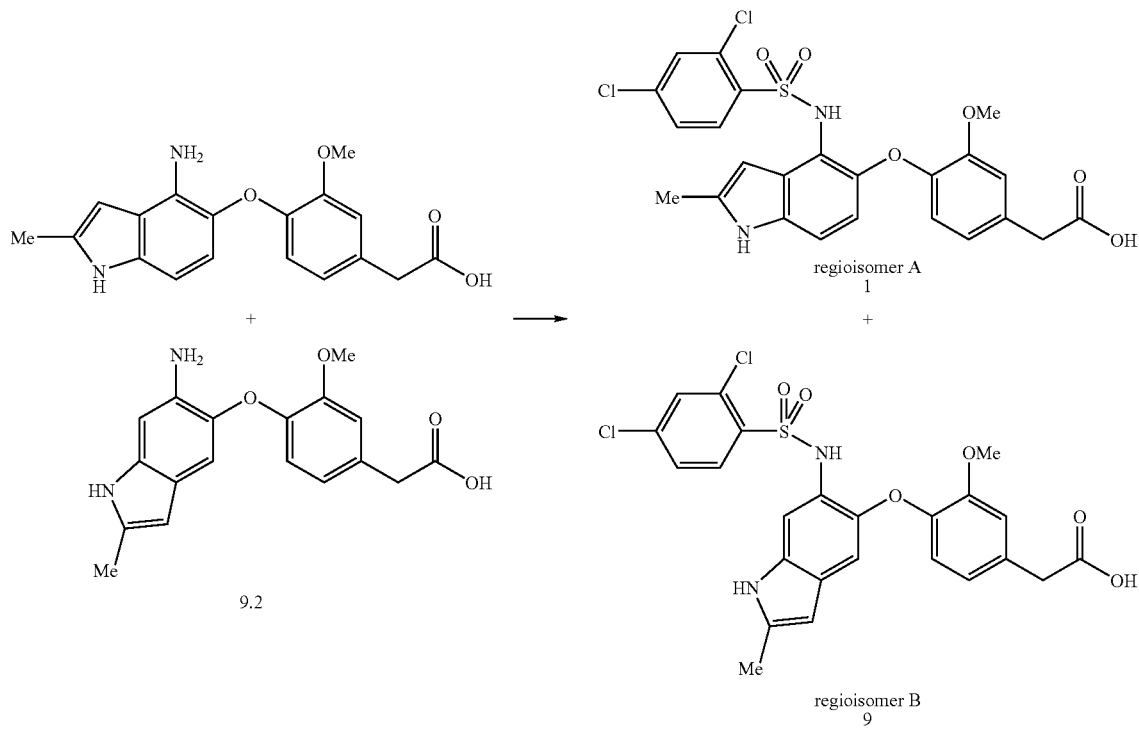

Scheme 9.2

Scheme 10.1

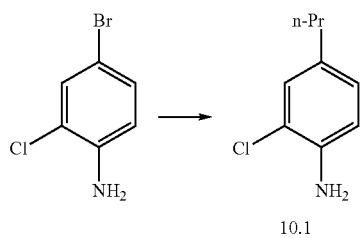

10.1. To a solution of B-MeO-9-BBN (11.0M in hexane, 22 mol) in THF (20 mL) at 0° C. was added n-propylmagnesium bromide (2.0M in ether, 10.5 mL). After 10 min, solvent was evaporated, and to the residue was added NMP (60 mL), Pd(dppf)Cl$_2$ (1.0 mmol), 4-bromo-2-chloroaniline (20 mmol) and aqueous sodium carbonate (1.0M, 30 mL). The reaction was then heated at 95° C. overnight. The reaction mixture was diluted with ethyl acetate (150 mL), washed with water (20×3 mL) and saturated brine (20 mL). The organic layer was dried with MgSO$_4$, filtered, and concentrated under reduced pressure. Flash chromatography of the residue (silica gel, slow gradient of 0-100% DCM in hexane) afforded 10.1. MS-ESI (pos.) m/z: 170 (M+H).

Scheme 10.2

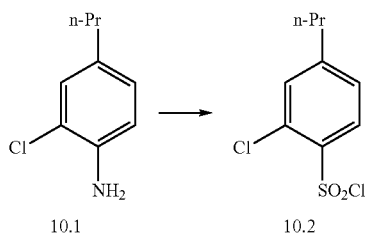

10.2. Compound 10.2 was prepared according to the procedure of Example 29 below. $^1$H NMR (400 MHz) (CDCl$_3$) δ 8.06 (d, 1 H); 7.47 (s, 1 H); 7.31 (d, 1 H); 2.70 (t, 2 H); 1.72 (h, 12 H); 1.00 (t, 3 H).

Scheme 10.3

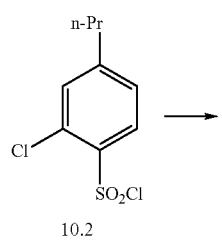

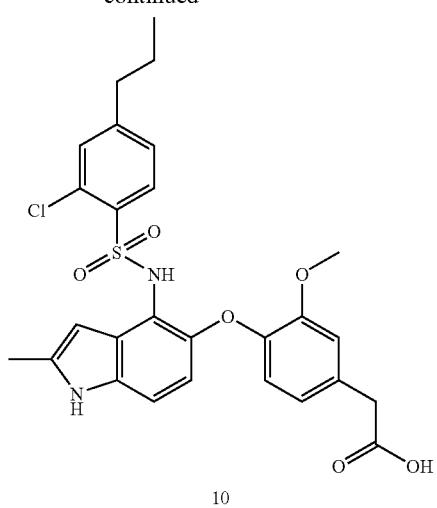

2-(4-(4-(2-Chloro-4-propylphenylsulfonamido)-2-methyl-1H-indol-5-yloxy)-3-methoxyphenyl)acetic acid (10). A solution of 1.3 (32 mg, 0.10 mmol) was dissolved in pyridine (0.5 mL) and to it was added 10.2 (50 mg), and the reaction was stirred overnight. The reaction was then blown dry, and to it was added THF (1 mL) and aqueous LiOH (3.0 M, 0.2 mL). After additional 2 h, the reaction mixture was blown by nitrogen to near dryness, and treated with DMSO (3 mL) and TFA (0.1 mL). Reverse phase HPLC of the resulting homogeneous solution afforded 10. LC-MS ESI (neg.) m/z: 543.1 (M−H). $^1$H NMR (400 MHz) (dmso-d$_6$) δ 10.88 (s, 1 H); 9.45 (s, 1 H); 7.61 (d, J=8.1 Hz, 1 H); 7.29 (s, 1 H), 7.08 (dd, J=1.6, 8.1 Hz, 1 H); 7.05 (d, J=8.9 Hz, 1 H); 6.90 (s, 1 H); 6.60 (dd, J=1.6, 8.2 Hz, 1 H); 6.28 (d, J=8.6 Hz, 1 H); 5.95 (s, 1 H); 3.70 (s, 3 H); 3.50 (s, 2 H); 2.54 (t, J=7.5 Hz, 2 H); 2.32 (s, 3 H); 1.55 (h, J=7.5 Hz, 2 H), 0.86 (t, J=7.5 Hz, 3 H).

7.11. Example 11

This example illustrates the preparation of 2-(4-((4-(2-chloro-4-(2,2,2-trifluoroethoxy)phenylsulfonamido)-2-methyl-1H-indol-5-yl)methyl)-3-methoxyphenyl)acetic acid (11).

Scheme 11.1

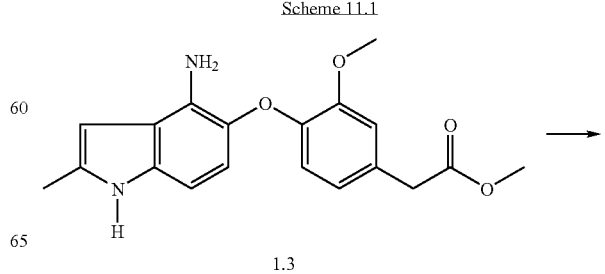

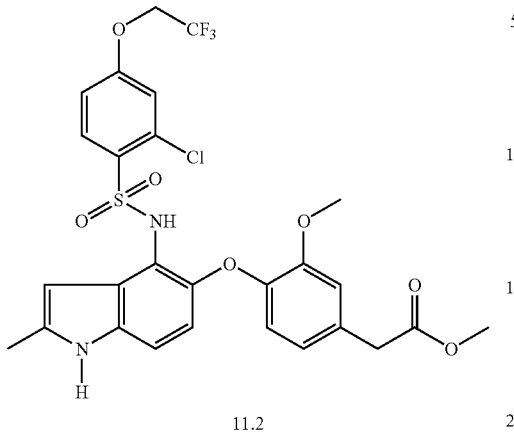

11.2

Methyl 2-(4-((4-(2-chloro-4-(2,2,2-trifluoroethoxy)phenylsulfonamido)-2-methyl-1H-indol-5-yl)methyl)-3-methoxyphenyl)acetate (11.2). Methyl 2-(4-((4-amino-2-methyl-1H-indol-5-yloxy)methyl)-3-methoxyphenyl)acetate 1.3 (30 mg, 0.088 mmol) in anhydrous pyridine (1 mol) was treated with 2-chloro-4-(2,2,2-trifluoroethoxy)benzene sulfonyl chloride (28.13 mg, 0.0968 mmol). After stirring 2 h, the reaction was diluted with ethyl acetate (5 mL) and washed with 1N HCl (2×), water (1×), saturated brine, dried over $Na_2SO_4$, and concentrated under reduced pressure. The residue was used immediately without further purification.

Scheme 11.2

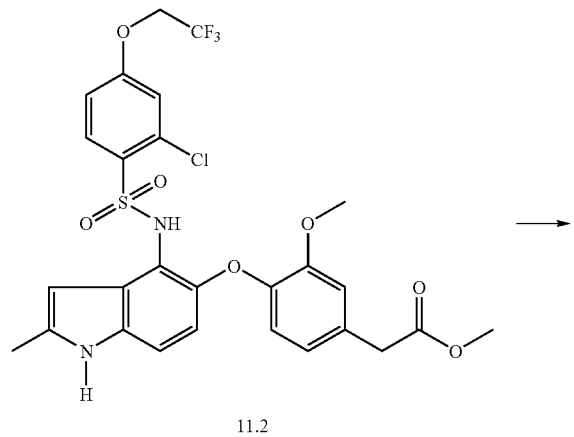

11.2

→

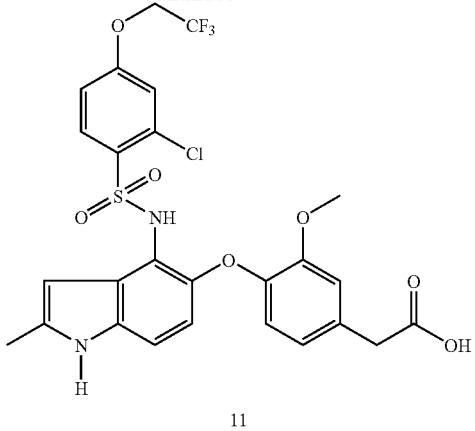

11

2-(4-((4-(2-Chloro-4-(2,2,2-trifluoroethoxy)phenylsulfonamido)-2-methyl-1H-indol-5-yl)methyl)-3-methoxyphenyl)acetic acid (11). Methyl acetate (32 mg, 52 mmol) was dissolved in a mixture of solvent 15 mL (THF:MeOH:$H_2O$=2:2:1). LiOH (11 mg, 261 mmol) was added to the solution. After stirring for 1 h, the reaction mixture was chromatographed using HPLC. Acetic acid derivative 11 was obtained as brown solid. LC-MS ESI (pos.) m/z: 599.0 (M+H). $^1H$ NMR (400 MHz) ($CD_3Cl_3$) & 7.87 (b, 1H); 7.77 (d, J=8.8 Hz, 1H); 7.54 (s, 1H); 7.03 (d, J=8.8 Hz, 1H); 6.84 (d, J=1.8 Hz, 1H); 6.75 (d, J=2.5 Hz, 1H); 6.68 (s, 1H), 6.59 (d, J=2.5 Hz, 1H); 6.44-6.55 (m, 2H); 6.19 (d, J=11.7 Hz, 1H); 4.25-4.31 (m, 2H); 3.82 (s, 3H); 3.61 (s, 2H); 2.5 (s, 3H).

7.12. Example 12

This example illustrates the preparation 2-(4-(4-(2,4-dichlorophenylsulfonamido)-2-methyl-1H-indol-5-yloxy)-2,3-dimethylphenyl)acetic acid (12).

Scheme 12.1

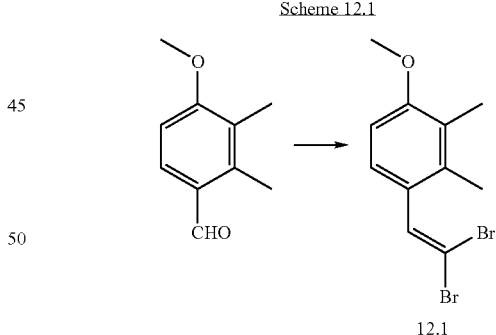

12.1

1-(2,2-Dibromovinyl)-4-methoxy-2,3-dimethylbenzene (12.1). Under an $N_2$ atmosphere, 2,3-dimethylanisaldehyde (3.0 g, 18.3 mmol) was dissolved in dichloromethane (100 mL) and cooled to 0° C. Carbon tetrabromide (9.10 g, 27.4 mmol) was added followed by a dropwise addition of triphenylphosphine (14.4 g, 54.9 mmol) in dichloromethane (100 mL). The reaction was allowed to stir at 1.5 h at 0° C. The reaction was concentrated in vacuo, and the resulting residue was suspended in a mixture of hexanes and chloroform (4:1). The solid was removed by filtration and discarded. The filtrate was concentrated in vacuo and flash column chromatographed on silica gel eluting with 0% to 40% ethyl acetate in hexanes to yield the desired product. $^1$H NMR (400 MHz) (CDCl$_3$) δ 7.44 (s, 1H); 7.19 (d, J=8.0 Hz, 1H); 6.72 (d, J=8.0 Hz, 1H), 3.82 (s, 3H); 2.17 (s, 3H); 2.16 (s, 3H).

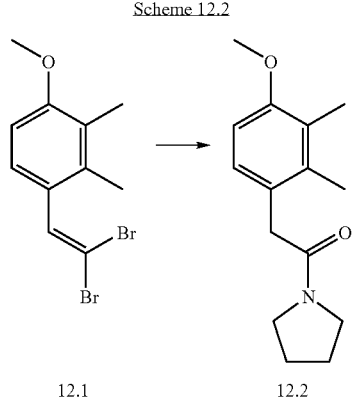

2-(4-Methoxy-2,3-dimethylphenyl)-1-(pyrrolidin-1-yl) ethanone (12.2). Under an N$_2$ atmosphere, 1-(2,2-dibromovinyl)-4-methoxy-2,3-dimethylbenzene was dissolved in a mixture of DMF (43 mL) and water (14 mL). Pyrrolidine (5.67 mL, 68 mmol) was added and the reaction was heated to 80° C. for 20 h. The reaction was diluted with Et$_2$O and water. The layers were separated and the organic layer was washed with 0.25M HCl (aq) and brine. The organic extract was dried (Na$_2$SO$_4$), filtered, and concentrated in vacuo. Flash column chromatography of the residue, eluting with 0% to 100% ethyl acetate in hexanes, afforded the title compound. LC-MS ESI (pos.) m/z: 248.2 (M+H).

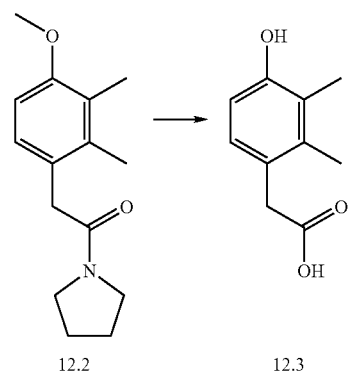

2-(4-Hydroxy-2,3-dimethylphenyl)acetic acid (12.3). 2-(4-Methoxy-2,3-dimethylphenyl)-1-(pyrrolidin-1-yl)ethanone was suspended in a mixture of 48% HBr (aq) (15 mL) and acetic acid (15 mL) and the reaction was heated to reflux for 24 h. The reaction was poured over ice and brought to pH 4 with 1 N NaOH. Ethyl acetate was added and the layers were separated. The organic layer was dried (Na$_2$SO$_4$), filtered and concentrated in vacuo. The residue was taken up in dioxane (100 mL) and 1 N HCl (15 mL) was added. The reaction was heated to reflux for 4 days. Ethyl acetate and 1N HCl were added. The layers were separated, and the aqueous layer was washed with additional ethyl acetate. The organics were combined, dried (Na$_2$SO$_4$), filtered and concentrated in vacuo. Flash column chromatography of the residue, eluting 0% to 7% methanol in dichloromethane, afforded the title compound. LC-MS ESI (neg.) m/z: 179.2 (M–H).

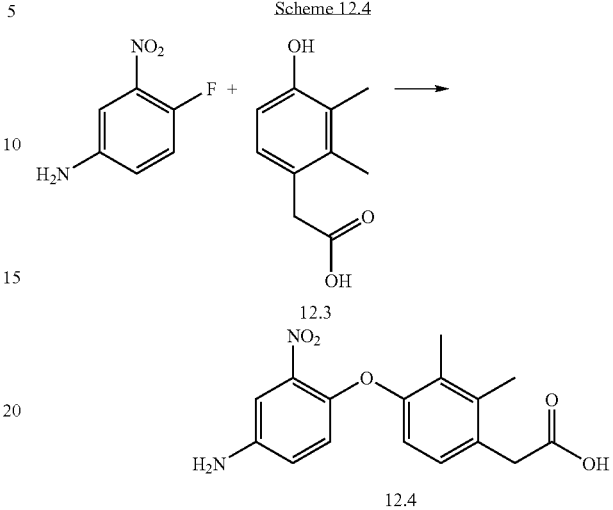

2-(4-(4-Amino-2-nitrophenoxy)-2,3-dimethylphenyl)acetic acid (12.4). Under an N$_2$ atmosphere, 2-(4-hydroxy-2,3-dimethylphenyl)acetic acid (0.780 g, 4.33 mmol) was dissolved in DMSO (29 mL). Cesium carbonate (3.53 g, 10.8 mmol) was added and the reaction was allowed to stir at room temperature for 5 min. 4-Fluoro-3-nitroaniline (0.678 g, 4.33 mmol) was added and the reaction was heated to 80° C. for 2.25 h. The reaction was allowed to cool to room temperature and diluted with water. Citric acid was added to pH 4 and the reaction was extracted with ethyl acetate. The layers were separated and the aqueous layer was washed with additional ethyl acetate. The organics were combined, dried (Na$_2$SO$_4$), filtered, and concentrated in vacuo. Flash column chromatography of the residue, eluting with 0% to 8% methanol in dichloromethane, afforded the title compound. LC-MS ESI (pos.) m/z: 317.2 (M+H).

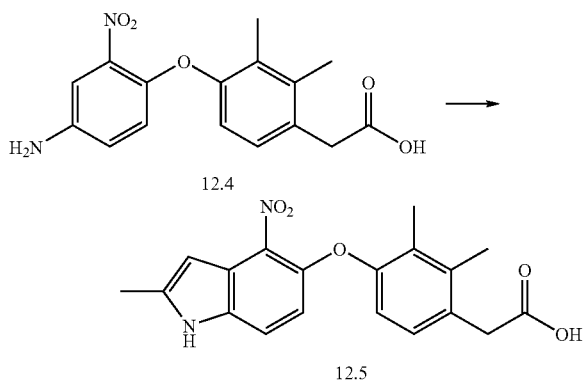

2-(2,3-Dimethyl-4-(2-methyl-4-nitro-1H-indol-5-yloxy) phenyl)acetic acid (12.5). Under an N$_2$ atmosphere, 2-(4-(4-amino-2-nitrophenoxy)-2,3-dimethylphenyl)acetic acid (0.723 g, 2.29 mmol) was dissolved in DMSO (18 mL) and acetone (0.503 mL, 6.86 mmol) was added. The reaction was treated with potassium tert-butoxide (0.770 g, 6.86 mmol) and allowed to stir at room temperature for 1.5 h. The reaction was diluted with water and citric acid was added to pH 4. The mixture was extracted with ethyl acetate. The aqueous layer was washed with additional ethyl acetate. The organics were combined, dried (Na₂SO₄), filtered and concentrated in vacuo. Flash column chromatography of the residue, eluting with 0% to 9% methanol in dichloromethane, afforded the title compound. LC-MS ESI (neg.) m/z: 353.2 (M−H).

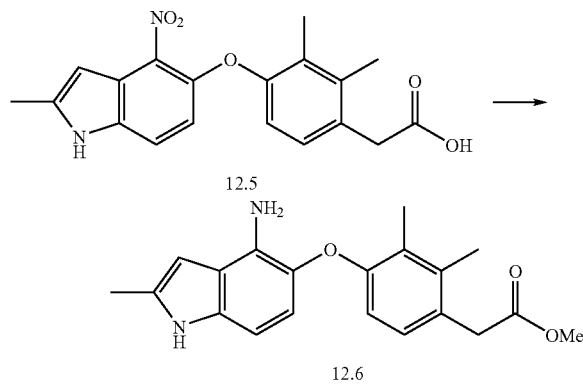

Methyl 2-(4-(4-amino-2-methyl-1H-indol-5-yloxy)-2,3-dimethylphenyl)acetate (12.6). Under an N₂ atmosphere, 2-(2,3-dimethyl-4-(2-methyl-4-nitro-1H-indol-5-yloxy)phenyl)acetic acid (0.335 g, 0.946 mmol) was suspended in methanol and tin chloride dihydrate (1.71 g, 7.57 mmol) was added. The reaction was heated to 60° C. for 16 h. The reaction was diluted with ethyl acetate and 10% NaHCO₃ (aq). The layers were separated and the organic layer was washed with water (3×), dried (Na2SO4), filtered and concentrated in vacuo. Flash column chromatography of the residue, eluting with 20% to 80% ethyl acetate in hexanes, afforded the title compound. LC-MS ESI (pos.) m/z: 339.2 (M+H).

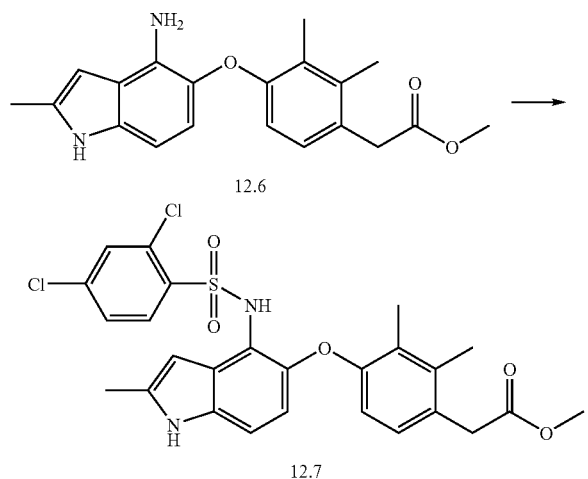

Methyl 2-(4-(4-(2,4-dichlorophenylsulfonamido)-2-methyl-1-indol-5-yloxy)-2,3-dimethylphenyl)acetate (12.7). Under an N₂ atmosphere, methyl 2-(4-(4-amino-2-methyl-1H-indol-5-yloxy)-2,3-dimethylphenyl)acetate (0.114 g, 0.337 mmol) was dissolved in dichloromethane (1.2 mL) and pyridine was added (0.027 mL, 0.337 mmol) followed by 2,4-dichlorobenzenesulfonyl chloride (0.83 g, 0.337 mmol). The reaction was allowed to stir at room temperature for 72 h. The reaction was diluted with ethyl acetate and saturated NH₄Cl (aq). The layers were separated and the organic layer was dried (Na₂SO₄), filtered, and concentrated in vacuo. Flash column chromatography of the residue, eluting with 20% to 60% ethyl acetate in hexanes, afforded title compound. LC-MS ESI (pos.) mm/z: 547.2 (M+H).

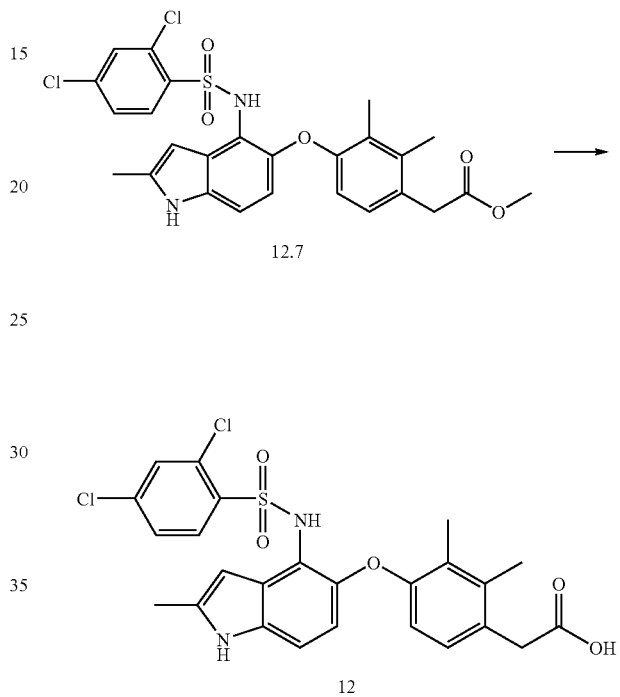

2-(4-(4-(2,4-Dichlorophenylsulfonamido)-2-methyl-1H-indol-5-yloxy)-2,3-dimethylphenyl)acetic acid (12). Under an N₂ atmosphere, methyl 2-(4-(4-(2,4-dichlorophenylsulfonamido)-2-methyl-1H-indol-5-yloxy)-2,3-dimethylphenyl)acetate (0.194 g, 0.354 mmol) was dissolved in tetrahydrofuran (2.5 mL) and 1N LiOH (aq) was added. The reaction was allowed to stir at room temperature for 2.5 h. The reaction was diluted with water and ethyl acetate. The layers were separated and the aqueous layer was made acidic with citric acid to pH 4 and extracted with ethyl acetate. The organic layer was dried (Na₂SO₄), filtered, and concentrated in vacuo. Flash column chromatography of the residue, eluting with 0% to 8% methanol in dichloromethane, afforded the title compound. LC-MS EST (neg.) m/z: 531.1 (M−H). ¹H NMR (400 MHz) (DMSO-d₆) δ 10.94 (s, 1H); 9.75 (s, 1H); 7.53 (d, J=8.5 Hz, 1H); 7.48 (d, J=2.0 Hz, 1H); 7.20 (dd, J=8.5 Hz and 2.0 Hz, 1H); 7.07 (d, J=8.6 Hz, 1H); 6.72 (d, J=8.4 Hz, 1H); 6.27 (d, J=8.4 Hz, 1H); 6.13 (s, 1H); 5.99 (d, J=8.4 Hz, 1H); 3.50 (s, 2H); 2.35 (s, 3H); 2.09 (s, 3H); 1.92 (s, 3H).

7.13. Example 13

This example illustrates the preparation of 2-(4-(2-cyano-4-(2,4-dichlorophenylsulfonamido)-1H-indol-5-yloxy)-3-methoxyphenyl)acetic acid (13).

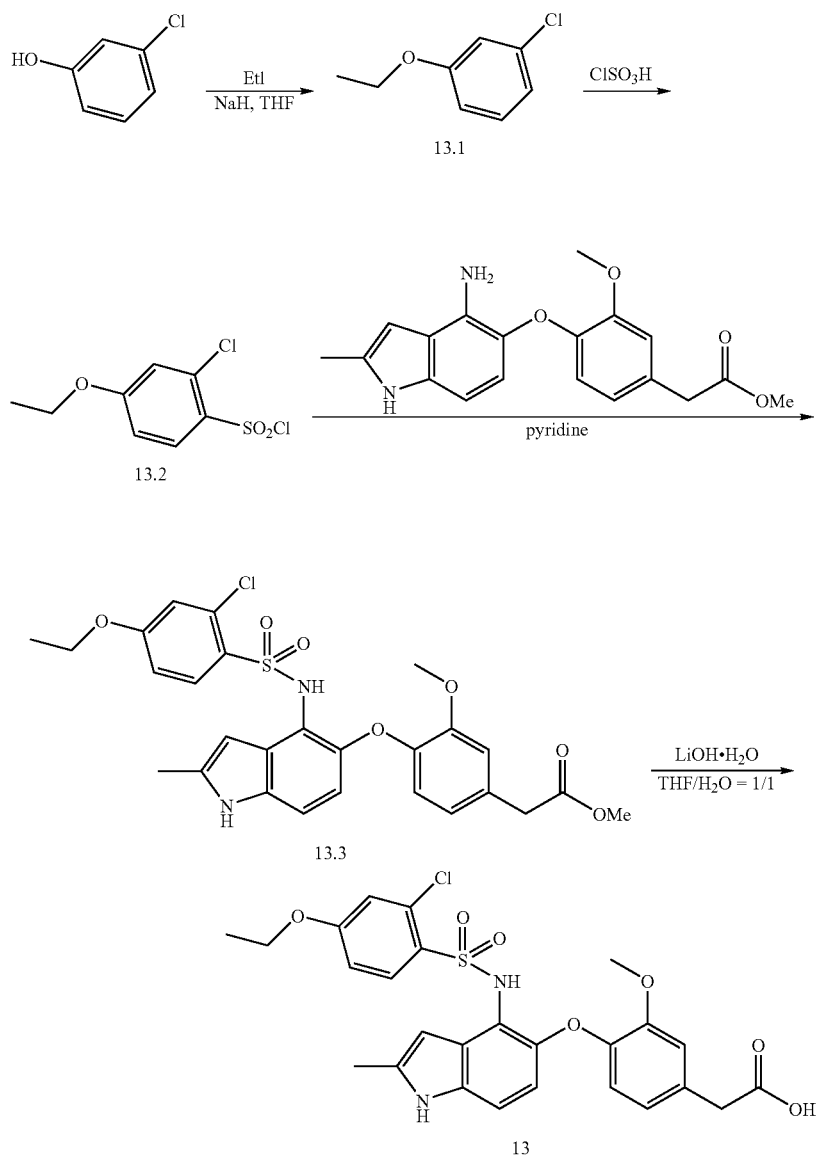

1-Chloro-3-ethoxybenzene (13.1). To a solution of 60% NaH (0.373 g, 9.34 mmol) in THF (20 mL), phenol (1 g, 7.78 mmol) was added dropwise at room temperature. The mixture was stirred at room temperature for 10 min. and then ethyl iodide (1.27 g, 8.17 mmol) was added. The solution was stirred overnight. The reaction mixture was poured into water and extracted twice with diethyl ether. The combined organic layers were washed with water, saturated brine, dried over $Na_2SO_4$, filtered, and concentrated under reduced pressure to afford 13.1 as colorless oil.

1-Chloro-3-ethoxybenzene (13.2). To a solution of 13.1 (2.32 g, 14.82 mmol) in $CHCl_3$ (30 mL) at 0° C., $ClSO_3H$ (4.32 g, 37.04 mmol) was added dropwise. The mixture was slowly returned to room temperature overnight. The solution was poured into ice water and extracted twice with DCM. The combined organic layers were washed with water, saturated brine, dried over $Na_2SO_4$, filtered, and concentrated under reduced pressure to afford 13.2 as a white solid.

2-(4-(2-Cyano-4-(2,4-dichlorophenylsulfonamido)-1H-indol-5-yloxy)-3-methoxyphenyl)acetic acid (13). The title compound was synthesized from 13.2 according to the methods described in Example 1 (see Schemes 1.4 and 1.5). MS ESI (pos.) m/z: 545.1 (M+1)$^{+1}$H NMR (400 MHz) (CDCl$_3$) δ 7.92 (s, 1H); 7.68 (d, J=8.4 Hz, 1H); 7.48 (s, 1H); 7.0 (d, J=8.4 Hz, 1H); 6.85 (s, 1H); 6.68 (s, 1H); 6.66 (m, 2H); 6.25 (d, J=8 Hz, 1H); 3.95 (q, J=7.3 Hz, 2H); 3.81 (s, 3H); 3.61 (s, 2H); 2.50 (s, 3H); 1.30 (t, J=7.3 Hz, 2H).

7.14. Example 14

This example illustrates the preparation of 2-(4-(4-(2,4-dimethylphenylsulfonamido)-2-(trifluoromethyl)-1H-indol-5-yloxy)-3-methoxyphenyl)acetic acid (14).

Scheme 14
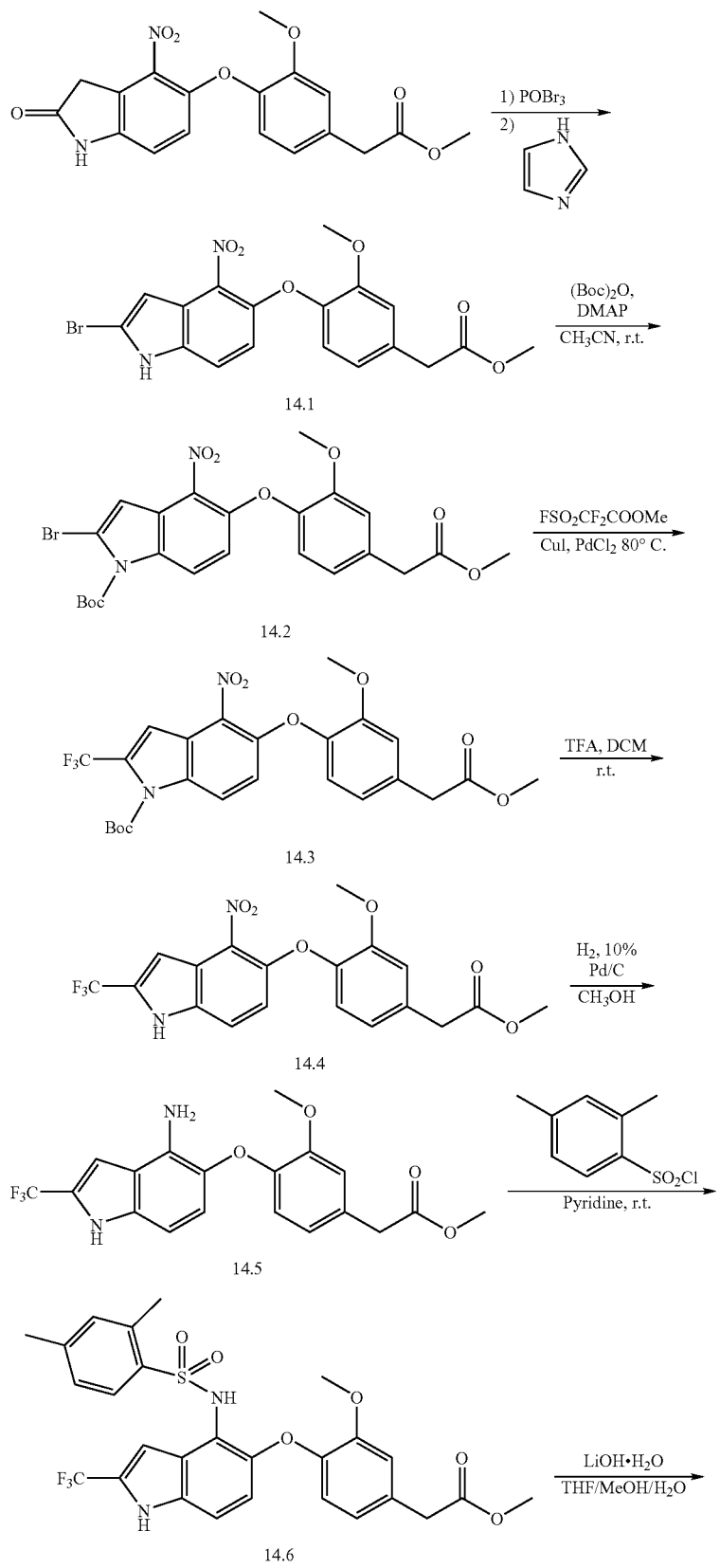

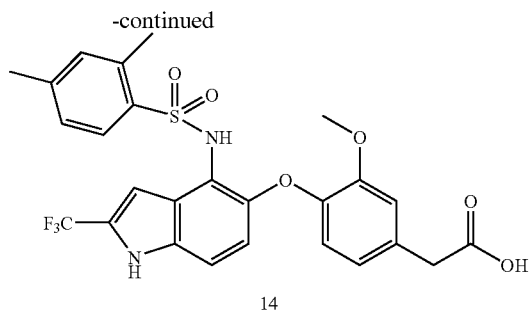

14

Methyl 2-(4-(2-bromo-4-nitro-1H-indol-5-yloxy)-3-methoxyphenyl)acetate (14.1). To a solution of methyl 2-(3-methoxy-4-(4-nitro-2-oxoindolin-5-yloxy)phenyl)acetate (0.177 g, 0.476 mmol) in DCE (10 mL), phosphoryl tribromide (0.273 g, 0.952 mmol) was added dropwise at room temperature. The mixture was heated at 90° C. for 1 h, and then imidazole (0.049 g, 0.714 mmol) was added and heated for another 2 h. The reaction was quenched with ice, adjusted PH to 8 and diluted with ethyl acetate. The organic layer was washed with saturated brine, dried over $Na_2SO_4$, filtered, and concentrated under reduced pressure. MS ESI (pos.) m/z: 435.1 $(M+H)^+$ tert-Butyl 2-bromo-5-(2-methoxy-4-(2-methoxy-2-oxoethyl)phenoxy)-4-nitro-1H-indole-1-carboxylate (14.2). A solution of 14.1 (0.155 g, 0.356 mmol) in $CH_3CN$ (10 mL) was treated with di-tert-butyl dicarbonate (0.082 g, 0.374 mmol) and DMAP (0.002 g, 0.018 mmol) at room temperature overnight. Solvent was removed and the residue was diluted with ethyl acetate. The organic layer was washed with 1N HCl, water and saturated brine, dried over $Na_2SO_4$, filtered, and concentrated under reduced pressure. MS ESI (pos.) m/z: 535.1 $(M+H)^+$.

tert-Butyl 5-(2-methoxy-4-(2-methoxy-2-oxoethyl)phenoxy)-4-nitro-2-(trifluoromethyl)-1H-indole-1-carboxylate (14.3). To a degassed DMF (8 mL), was added 14.2 (0.085 g, 0.158 mmol), methyl 2,2-difluoro-2-(fluorosulfonyl)acetate (0.303 g, 1.58 mmol), $PdCl_2$ (0.011 g, 0.063 mmol) followed by CuI (0.12 g, 0.63 mmol). The mixture was heated at 80° C. for 1 h and then diluted with ethyl acetate. The organic layer was washed with water and saturated brine, dried over $Na_2SO_4$, filtered, and concentrated under reduced pressure. The residue was flash chromatographed. Compound 14.3 was obtained as a white solid. MS ESI (pos.) m/z: 525.2 $(M+H)^+$.

tert-Butyl 5-(2-methoxy-4-(2-methoxy-2-oxoethyl)phenoxy)-4-nitro-2-(trifluoromethyl)-1H-indole-1-carboxylate (14.4). To a solution of 14.3 (0.028 g, 0.053 mmol) in DCM (2 mL), was added trifluoroacetic acid (1 mL). The mixture was stirred at room temperature for 1 h. Solvent was evaporated. MS ESI (pos.) m/z: 425.1 $(M+H)^+$.

Methyl 2-(4-(4-amino-2-(trifluoromethyl)-1H-indol-5-yloxy)-3-methoxyphenyl)acetate (14.5). To a solution of 14.4 (0.020 g, 0.047 mmol) in methanol (2 mL), was added 10% Pd/C (0.006 g, 0.005 mmol). The mixture was stirred under hydrogen at room temperature for 1 h. Solvent was removed after filtration to give a residue. MS ESI (pos.) m/z: 395.1 $(M+H)^+$.

Methyl 2-(4-(4-(2,4-dimethylphenylsulfonamido)-2-(trifluoromethyl)-1H-indol-5-yloxy)-3-methoxyphenyl)acetate (14.6). The mixture of 14.5 (0.018 g, 0.046 mmol) and aryl sulfonylchloride (0.010 g, 0.048 mmol) in pyridine (0.5 mL) was stirred at room temperature overnight. Solvent was removed to give a residue. MS ESI (pos.) m/z: 563.2 $(M+H)^+$.

2-(4-(4-(2,4-Dimethylphenylsulfonamido)-2-(trifluoromethyl)-1H-indol-5-yloxy)-3-methoxyphenyl)acetic acid (14). To a solution of 14.6 (0.020 g, 0.047 mmol) in a mixture of $THF/CH_3OH/H_2O$ (0.5 mL, ratio=2/2/1), was added $LiOH \cdot H_2O$ (0.010 g, 0.220 mmol). The mixture was stirred at room temperature for 1 h. The solution was chromatographed using HPLC to give 14 as a white solid. MS ESI (pos.) m/z: 549.2 $(M+H)^+$. $^1H$ NMR (400 MHz) $(CDCl_3)$ δ 8.32 (s, 1H); 7.57 (d, J=7.2 Hz, 1H); 7.20 (s, 1H); 7.11 (d, J=7.2 Hz, 1H); 6.86 (m, 3H); 6.71 (d, J=9.2 Hz, 1H): 6.64 (d, J=8 Hz, 1H); 6.34 (d, J=8 Hz, 1H); 3.80 (s, 3H); 3.62 (s, 2H); 2.53 (s, 3H); 2.33 (s, 3H).

7.15. Example 15

This example illustrates the preparation of 2-(4-(2-carbamoyl-4-(2,4-dichlorophenylsulfonamido)-1H-indol-5-yloxy)-3-methoxyphenyl)acetic acid (15).

Scheme 15

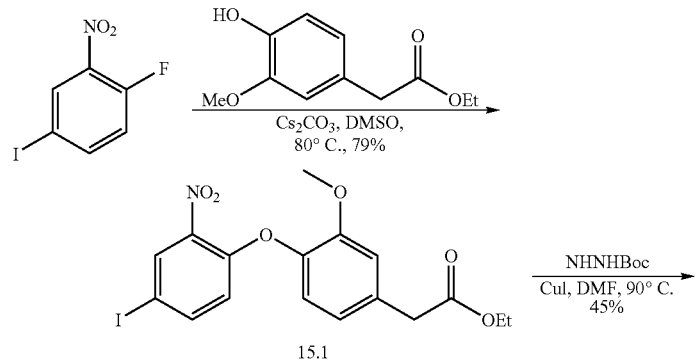

15.1

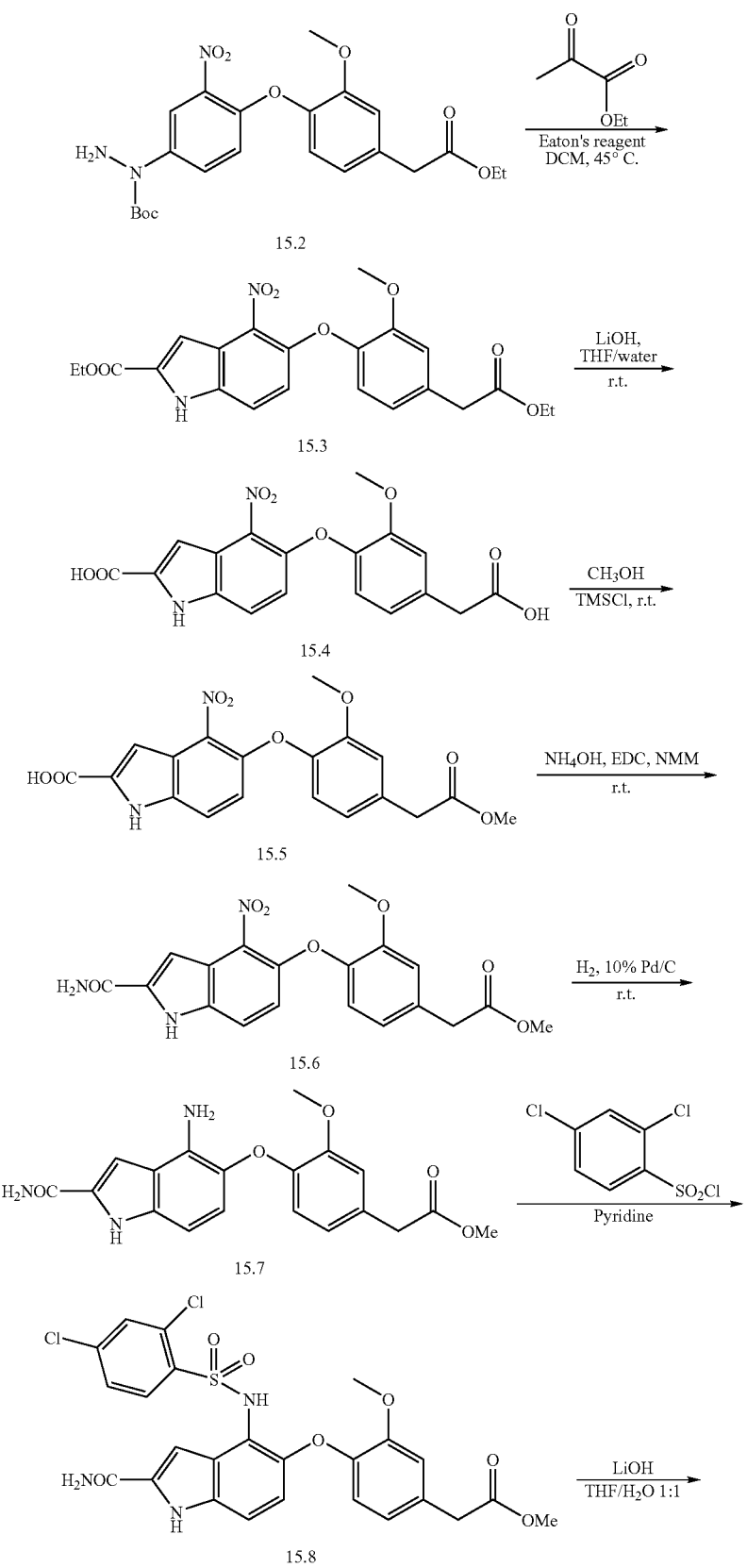

-continued

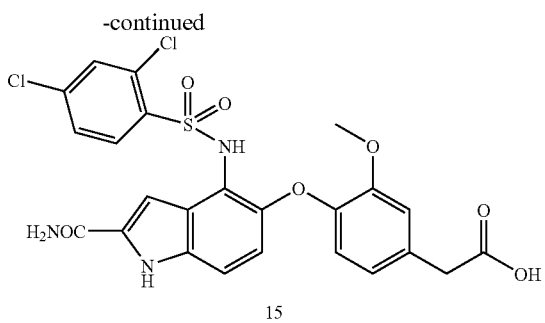

15

Ethyl 2-(4-(4-iodo-2-nitrophenoxy)-3-methoxyphenyl)acetate (15.1). To a solution of 1-fluoro-4-iodo-2-nitrobenzene (9.13 g, 34.20 mmol) and ethyl 2-(4-hydroxy-3-methoxyphenyl)acetate (7.19 g, 34.20 mmol) in DMSO (100 mL), $CsCO_3$ (12.26 g, 37.62 mmol) was added at room temperature. The mixture was heated at 100° C. for 2 h. The reaction was diluted with ethyl acetate and washed with water, saturated brine, dried over $Na_2SO_4$, filtered, and concentrated under reduced pressure to give a white solid. The residue was used without further purification. MS ESI (pos.) m/z: 458.0 (M+H)$^+$.

Ethyl 2-(4-(4-iodo-2-nitro-4-(1-tert-butylcarboxylphenoxy)-3-methoxyphenyl)acetate (15.2). An oven-dried bottle was charged with 15.1 (2 g, 4.51 mmol), tert-butyl carbazate (0.72 g, 5.42 mmol), CuI (0.064 g, 0.34 mmol), and $Cs_2CO_3$ (2.06 g, 6.31 mmol). The bottle was evacuated and backfilled with nitrogen. Anhydrous DMF (20 mL) was added and the mixture was stirred at room temperature for 10 min and then heated at 65° C. for 1 h. The reaction was diluted with ethyl acetate and washed with water, saturated brine, dried over $Na_2SO_4$, filtered, and concentrated under reduced pressure. The residue was used without further purification. MS ESI (pos.) m/z: 479.2 (M+18)$^+$.

Ethyl 5-(4-(2-ethoxy-2-oxoethyl)-2-methoxyphenoxy)-4-nitro-1H-indole-2-carboxylate (15.3). To a solution of 15.2 (1.71 g, 3.71 mmol) and ethyl 2-oxopropanoate (0.45 g, 3.89 mmol) in DCM (20 mL), Eaton's reagent (5.5 mL) was added dropwise at room temperature. The mixture was stirred at room temperature for 10 min and then heated at 45° C. for 5 h. The reaction was diluted with ethyl acetate and washed with water, saturated brine, dried over $Na_2SO_4$, filtered, and concentrated under reduced pressure. Flash chromatography of the residue afforded 15.3 as a yellow solid. MS EST (pos.) m/z: 443.2 (M+1)$^+$.

5-(4-(Carboxymethyl)-2-methoxyphenoxy)-4-nitro-1H-indole-2-carboxylic acid (15.4). To a solution of 15.3 (0.62 g, 1.40 mmol) in a mixture of $THF/CH_3OH/H_2O$ (10 mL, ratio=2/2/1), was added $LiOH.H_2O$ (1.17 g, 28 mmol). The mixture was stirred at room temperature overnight. The reaction was neutralized with 1N HCl to PH=2, extracted with ethyl acetate twice, the combined organic layer was washed with saturated brine, dried over $Na_2SO_4$, filtered, and concentrated under reduced pressure. The residue was used without further purification. MS EST (pos.) m/z: 387.1 (M+H)$^+$.

5-(2-Methoxy-4-(2-methoxy-2-oxoethyl)phenoxy)-4-nitro-1H-indole-2-carboxylic acid (15.5). To a solution of 15.4 (0.37 g, 0.96 mmol) in $CH_3OH$ (10 mL), was added TMSCl (0.1 g, 0.92 mmol). The mixture was stirred at room temperature for 3 h. Solvent was removed to give a residue, which was used without further purification. MS ESI (pos.) m/z: 401.0 (M+H)$^+$.

Methyl 2-(4-(2-carbamoyl-4-nitro-1H-indol-5-yloxy)-3-methoxyphenyl)acetate (15.6). The mixture of 15.5 (0.383 g, 0.959 mmol), EDC (0.552 g, 2.877 mmol) and HOBt (0.324 g, 2.40 mmol) was stirred at room temperature for 10 min., then 28% ammonium hydroxide (0.60 g, 4.795 mmol) was added to the solution and stirred for another 2 h. The reaction was diluted with ethyl acetate and washed with water, saturated brine, dried over $Na_2SO_4$, filtered, and concentrated under reduced pressure to give 0.6 as a yellow solid. MS ESI (pos.) m/z: 400.1 (M+1)$^+$.

2-(4-(2-Carbamoyl-4-(2,4-dichlorophenylsulfonamido)-1H-indol-5-yloxy)-3-methoxyphenyl)acetic acid (15). The title compound was synthesized from 15.6 according to the methods described in Example 14 (from 14.4 to 14). MS ESI (pos.) m/z: 564.1 (M+1)$^+$. $^1$H NMR (400 MHz) (CDCl$_3$) δ 9.4 (s, 1H); 7.69 (d, J=8 Hz, 1H); 7.40 (s, 1H); 7.22 (d, J=8 Hz, 1H); 7.12 (m, 2H); 6.91 (s, 1H); 6.73 (d, J=8.8 Hz, 1H); 6.58 (d, J=8 Hz, 1H); 6.20 (d, J=8 Hz, 1H); 3.82 (s, 3H); 3.64 (s, 2H).

7.16. Examples 16 and 17

Compounds 16 and 17 were prepared from compound 15.5 using methylamine and dimethylamine, respectively, instead of $NH_4OH$ according to the methods described in Example 15.

| Compound | R$^1$ | R$^2$ |
|---|---|---|
| 16 | H | Me |
| 17 | Me | Me |

Compound 16. MS ESI (pos.) m/z: 578.0 (M+1)$^+$. $^1$H NMR (400 MHz) (MeOD) δ 7.68 (d, J=8 Hz, 1H); 7.37 (s, 1H); 7.28 (m, 2H); 7.20 (d, J=8 Hz, 1H); 6.95 (s, 1H); 6.63 (m, 2H); 6.21 (d, J=8.2 Hz, 1H); 3.78 (s, 3H); 3.59 (s, 2H); 2.97 (s, 3H).

Compound 17. MS ESI (pos.) m/z: 592.0 (M+1)$^+$. $^1$H NMR (400 MHz) (CD$_3$CN) δ 9.84 (s, 1H); 7.68 (d, J=8 Hz, 1H); 7.40 (s, 1H); 7.22 (d, J=8 Hz, 1H); 7.26 (d, J=8 Hz, 1H); 7.00

(s, 1H); 6.95 (s, 1H); 6.65 (m, 2H); 6.41 (d, J=8 Hz, 1H); 3.74 (s, 3H); 3.60 (s, 2H); 3.18 (s, 6H).

7.17. Example 18

This example illustrates the preparation of 2-(4-(2-cyano-4-(2,4-dichlorophenylsulfonamido)-1H-indol-5-yloxy)-3-methoxyphenyl)acetic acid (18)

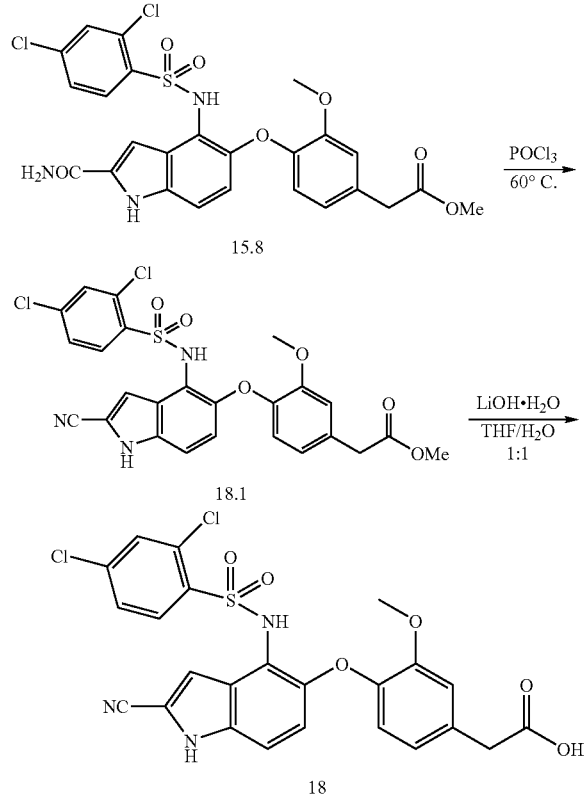

Methyl 2-(4-(2-cyano-4-(2,4-dichlorophenylsulfonamido)-1H-indol-5-yloxy)-3-methoxyphenyl)acetate (18.1). The mixture of 15.8 (0.031 g, 0.054 mmol) and POCl$_3$ (0.5 mL) was heated at 60° C. for 1 h. Solvent was evaporated, the residue was diluted with ethyl acetate and washed with sat. NaHCO$_3$, water, saturated brine, dried over Na$_2$SO$_4$, filtered, and concentrated under reduced pressure to give 18.1 as a pale yellow solid. MS ESI (pos.) m/z: 560.1 (M+1)$^+$.

2-(4-(2-Cyano-4-(2,4-dichlorophenylsulfonamido)-1H-indol-5-yloxy)-3-methoxyphenyl)acetic acid (18). The title compound was synthesized from 18.1 according to the methods described in Example 14 (from 14.6 to 14). MS ESI (pos.) m/z: 546.0 (M+1)$^+$. $^1$H NMR (400 MHz) (CDCl$_3$) δ 8.86 (s, 1H); 7.67 (m, 3H); 7.16 (m, 2H); 6.89 (s, 1H); 6.78 (d, J=8.4 Hz, 1H); 6.63 (d, J=8 Hz, 1H); 6.25 (d, J=8 Hz, 1H); 3.81 (s, 3H); 3.61 (s, 2H).

7.18. Example 19

This example illustrates the preparation 2-(2-chloro-4-(7-(2,4-dimethylphenylsulfonamido)-2-(methylamino)benzo[d]thiazol-6-yloxy)-5-methoxyphenyl)acetic acid (19).

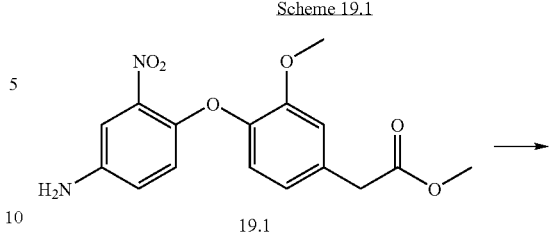

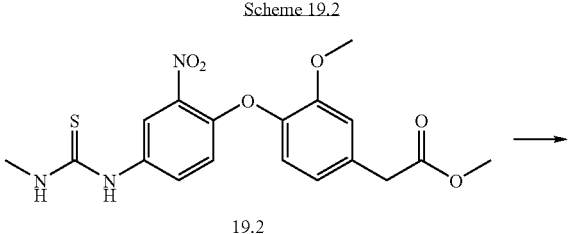

Methyl 2-(4-(2-amino-4-(3-methylthioureido) phenoxy)-3-methoxyphenyl)acetate (19.2). Compound 19.1 (1.5 g, 4.7 mol) was dissolved in ethanol (20 mL), isothiocyanato-methane (1.35 g, 18.5 mmol) was added. The reaction mixture was stirring at 100° C. for 2 h. The reaction mixture was concentrated under reduced pressure. Flash chromatography of the residue (silica gel, 60% ethyl acetate in hexane eluant) afforded 19.2. LC-MS ESI (pos.) m/z: 406.1 (M+H).

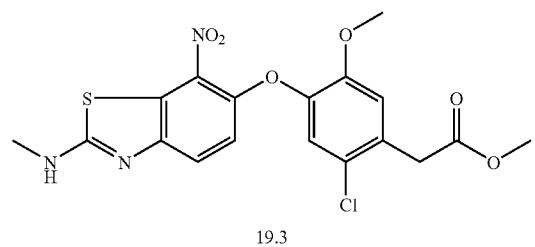

Methyl 2-(2-chloro-5-methoxy-4-(2-(methylamino)-7-nitrobenzo[d]thiazol-6-yloxy)phenyl)acetate (19.3). Compound 19.2 (400 mg, 0.988 mmol) was dissolved in 10 mL CH$_2$Cl$_2$ sulfuryl dichloride (373 mg, 2.5 mmol) was added dropwise. After 1 h, the reaction mixture was concentrated under reduced pressure. HPLC of the residue afforded 19.3.

Scheme 19.3

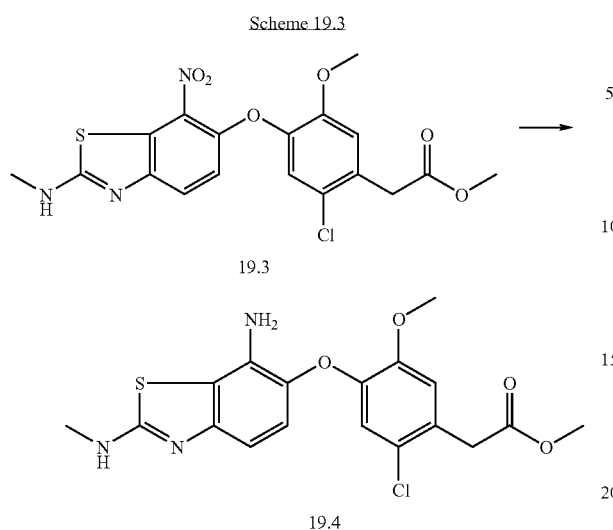

Methyl 2-(4-(7-amino-2-(methylamino)benzo[d]thiazol-6-yloxy)-2-chloro-5-methoxyphenyl)acetate (19.4). Compound 19.3 (230 mg, 0.53 mmol) was dissolved in mixture of ethyl acetate (3 mL) and methanol (1 mL). 10% Pd/C (56 mg, 0.053 mmol) was added and the reaction mixture was stirred for 1.5 h under $H_2$ at room temperature. The reaction mixture was filtered, the residue concentrated under reduced pressure to afford 19.4.

Scheme 19.4

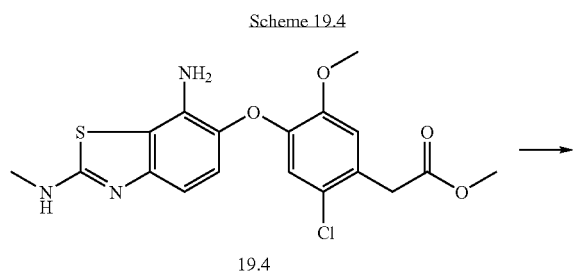

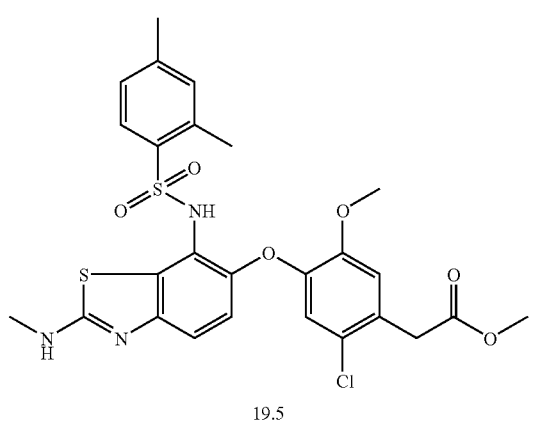

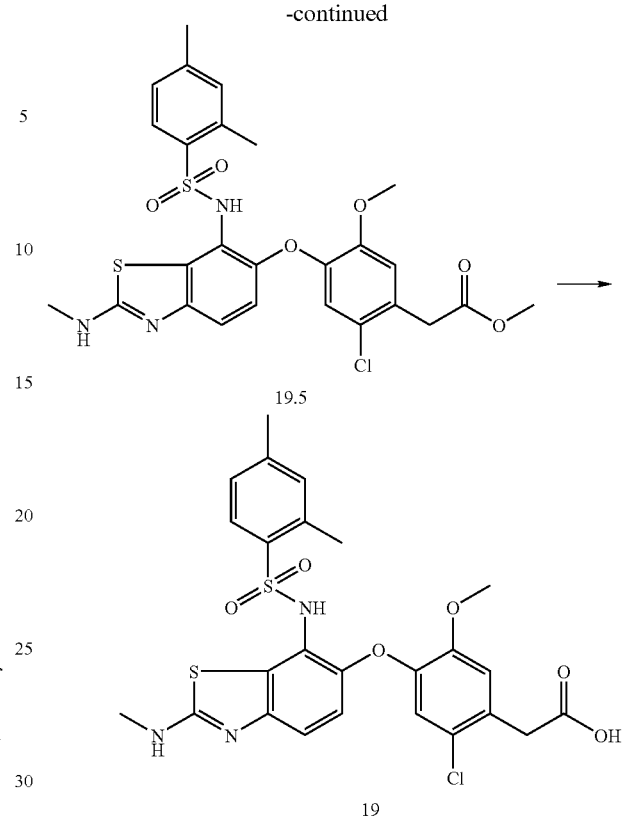

2-(2-Chloro-4-(7-(2,4-dimethyphenylsulfonamido)-2-(methylamino)benzo[d]thiazol-6-yloxy)-5-methoxyphenyl)acetic acid (19). The title compound was prepared from 19.4 according to the methods described in Example 11. MS ESI (pos.) m/z: 562.1 (M+H). $^1$H NMR (400 MHz) (CD$_3$OD) δ 7.57 (d, J=7.9 Hz, 1H); 7.25 (s, J=8.8 Hz, 1H); 7.07 (s, 1H); 6.99-7.03 (m, 2H); 6.63 (d, J=8.8 Hz, 1H); 6.05 (s, 1H); 6.44-6.55 (m, 2H); 3.75 (s, 2H); 3.75 (s, 3H); 3.17 (s, 3H); 2.57 (s, 3H); 2.32 (s, 3H).

7.19. Example 20

This example illustrates the preparation 2-(3-chloro-4-(4-(2,4-dichlorophenylsulfonamido)-2-methyl-1H-benzo[d]imidazol-5-yloxy)phenyl)acetic acid (20).

Scheme 20.1

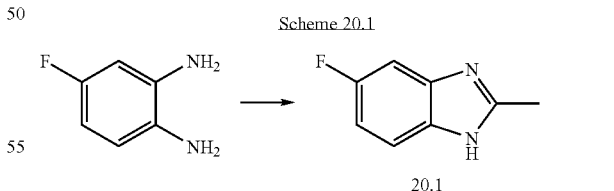

5-Fluoro-2-methyl-1H-benzo[d]imidazole (20.1). Under an N$_2$ atmosphere, 4-fluorobenzene-1,2-diamine (5.00 g, 39.6 mmol) was suspended in EtOH (220 mL) and 5M HCl (160 mL) was added. The reaction was warmed to 50° C. and 2,4-pentandione (8.14 mL, 7.93 mmol) was added and the reaction was heated to reflux for 30 min. Upon cooling to room temperature, the reaction was neutralized with a saturated solution of NaHCO$_3$(aq) and extracted with dichloromethane. The layers were separated and the aqueous layer was washed with additional dichloromethane (2×). The organics were then combined, dried (Na$_2$SO$_4$), filtered and concentrated in vacuo. The resulting solid was triturated with dichloromethane to afford the title compound. $^1$H NMR (400 MHz) (DMSO-d$_6$) δ 7.43-7.19 (bm, 2H); 6.92 (bs, 1H); 2.44 (s, 3H).

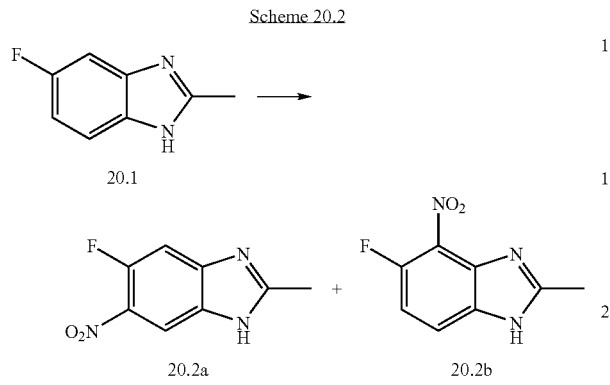

5-Fluoro-2-methyl-6-nitro-1H-benzo[d]imidazole (20.2a) and 5-Fluoro-2-methyl-4-nitro-1H-benzo[d]imidazole (20.2b). Under an N$_2$ atmosphere, 5-fluoro-2-methyl-1H-benzo[d]imidazole (5.21 g, 34.7 mmol) was dissolved in concentrated sulfuric acid (25 mL) and cooled to 0° C. Nitric acid (25 mL) was added and the reaction was stirred at 0° C. for 1 h. The reaction was poured over ice and neutralized with 1N NaOH. The mixture was extracted with ethyl acetate (3×). The organics were combined, dried (Na$_2$SO$_4$), filtered and concentrated in vacuo. The residue was triturated with 10% MeOH in dichloromethane to afford 1.00 g of 5-fluoro-2-methyl-6-nitro-1H-benzo[d]imidazole after filtration. The filtrate was flash column chromatographed, eluting with 2% to 7% MeOH in dichloromethane, to afford 5-fluoro-2-methyl-4-nitro-1H-benzo[d]imidazole. LC-MS ESI (pos.) m/z: 196.0 (M+H).

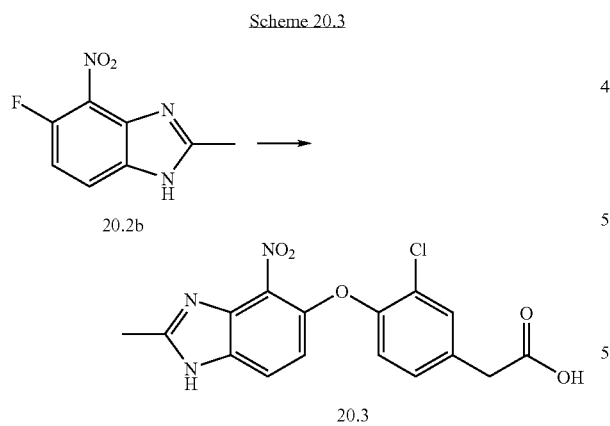

2-(3-Chloro-4-(2-methyl-4-nitro-1H-benzo[d]imidazol-5-yloxy)phenyl)acetic acid (20.3). Under an N$_2$ atmosphere, 5-fluoro-2-methyl-4-nitro-1H-benzo[d]imidazole (0.233 g, 1.19 mmol) was treated with Al$_2$O$_3$ supported potassium fluoride (0.583 g, 40 wt. %), 3-chloro-4-hydroxyphenylacetic acid (0.223 g, 1.19 mmol) and 18-crown-6 (0.031 g, 0.119 mmol) in DMSO (1 mL). The reaction was heated 80° C. for 20 h. Upon cooling to room temperature, the reaction was diluted with water and 1N HCl was added to pH 5. The reaction was extracted with ethyl acetate (3×). The organics were combined, dried (Na$_2$SO$_4$), filtered and concentrated in vacuo. Flash column chromatography of the residue, eluting with 0% to 10% methanol in dichloromethane, afforded the title compound. LC-MS ESI (pos.) m/z: 362.0 (M+H).

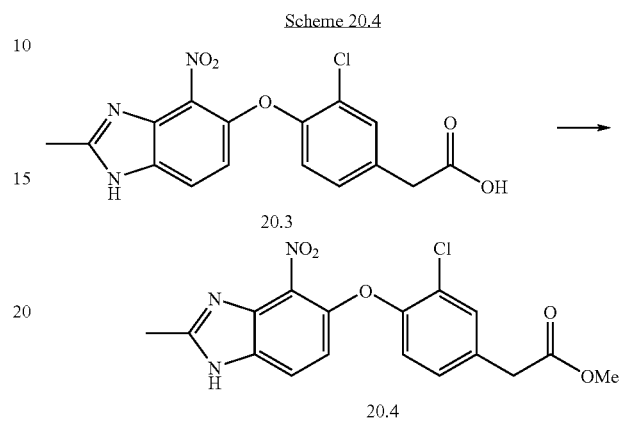

Methyl 2-(3-chloro-4-(2-methyl-4-nitro-1H-benzo[d]imidazol-5-yloxy)phenyl)acetate (20.4). Under an N$_2$ atmosphere, 2-(3-chloro-4-(2-methyl-4-nitro-1H-benzo[d]imidazol-5-yloxy)phenyl)acetic acid (0.331 0.915 mmol) was dissolved in methanol and concentrated sulfuric acid (3 drops) was added. The reaction was heated to reflux for 2.5 h, cooled to room temperature and concentrated in vacuo. The residue was partitioned between saturated NaHCO$_3$ (aq) and ethyl acetate. The layers were separated and the aqueous layer washed with additional ethyl acetate (2×). The organics were combined, dried (Na$_2$SO$_4$), and concentrated in vacuo. Flash column chromatography of the residue, eluting 0% to 3% methanol in dichloromethane, afforded title compound. LC-MS ESI (pos.) m/z: 376.0 (M+H).

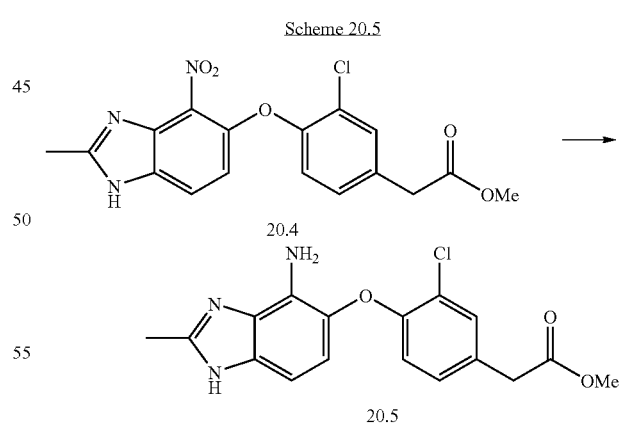

Methyl 2-(4-(4-amino-2-methyl-1H-benzo[d]imidazol-5-yloxy)-3-chlorophenyl)acetate (20.5). Under an N$_2$ atmosphere, methyl 2-(3-chloro-4-(2-methyl-4-nitro-1H-benzo[d]imidazol-5-yloxy)phenyl)acetate (0.226 g, 0.601 mmol) was dissolved in ethyl acetate and tin chloride dihydrate (0.543 g, 2.41 mmol) was added. The reaction was allowed to stir at room temperature for 16 h. The reaction was diluted with ethyl acetate and washed with a 10% NaHCO$_3$ (aq)

solution. The aqueous layer was washed with additional ethyl acetate. The organics were combined, dried (Na$_2$SO$_4$), filtered, and concentrated in vacuo, and the title compound isolated. LC-MS ESI (pos.) m/z: 346.0 (M+H).

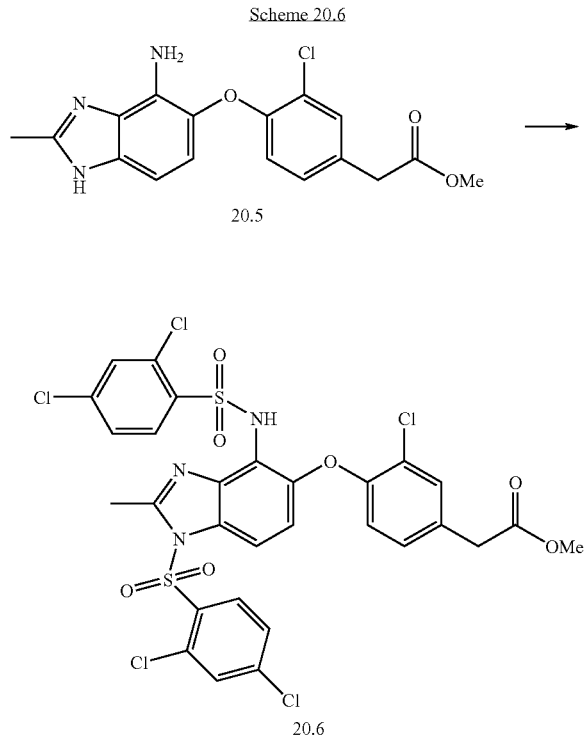

Methyl 2-(3-chloro-4-(4-(2,4-dichlorophenylsulfonamido)-1-(2,4-dichlorophenylsulfonyl)-2-methyl-1H-benzo[d]imidazol-5-yloxy)phenyl)acetate (20.6). Under an N$_2$ atmosphere, methyl 2-(4-(4-amino-2-methyl-1H-benzo[d]imidazol-5-yloxy)-3-chlorophenyl)acetate (0.171 g, 0.495 mmol) was dissolved in pyridine (1.5 mL) and 2,4-dichlorobenzenesulfonyl chloride (0.267 g, 1.09 mmol) was added. The reaction was allowed to stir at room temperature for 3 h and then concentrated in vacuo. Flash column chromatography of the residue, eluting 0% to 50% ethyl acetate in hexanes, afforded the title compound. LC-MS ESI (pos.) m/z: 763.7 (M+H).

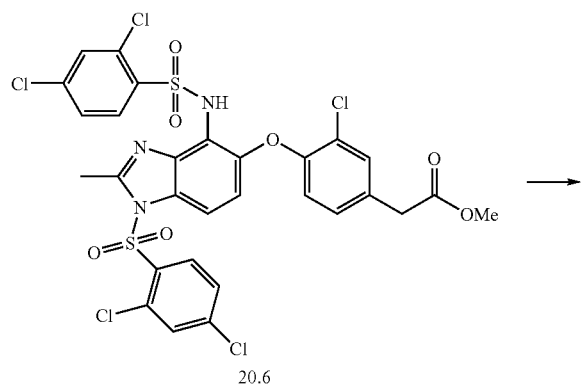

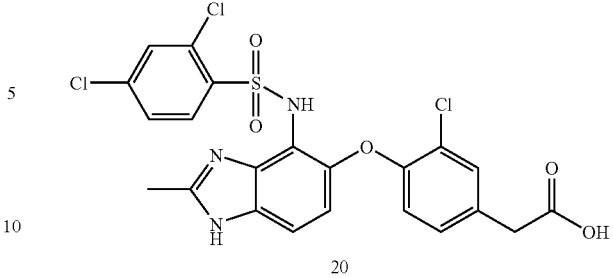

2-(3-Chloro-4-(4-(2,4-dichlorophenylsulfonamido)-2-methyl-1H-benzo[d]imidazol-5-yloxy)phenyl)acetic acid (20). Under an N$_2$ atmosphere, methyl 2-(3-chloro-4-(4-(2,4-dichlorophenylsulfonamido)-1-(2,4-dichlorophenylsulfonyl)-2-methyl-1H-benzo[d]imidazol-5-yloxy)phenyl)acetate (0.097 g, 0.127 mmol) was dissolved in tetrahydrofuran (1.5 mL) and 1 N LiOH (1.5 mL) was added. The reaction was stirred at 50° C. for 3 h. The reaction was diluted with water, made acidic with 1N HCl to pH 4, and extracted with ethyl acetate. The organic layer was dried (Na$_2$SO$_4$), filtered, and concentrated in vacuo to afford the title compound. LC-MS ESI (pos.) m/z: 541.9 (M+H). $^1$H NMR (400 MHz) (DMSOd-$_6$) δ 7.63 (d, J=8.5 Hz, 1H); 7.46 (bs, 1H); 7.31-7.22 (m, 3H); 6.94 (d, J=7.6 Hz, 1H); 6.46 (bs, 1H); 6.29 (bs, 1H) 3.51 (s, 2H); 2.48 (s, 3H).

7.20. Example 21

This example illustrates the preparation 2-(3-chloro-4-(6-(2,4-dichlorophenylsulfonamido)-2-methyl-3H-benzo[d]imidazol-5-yloxy)phenyl)acetic acid (21).

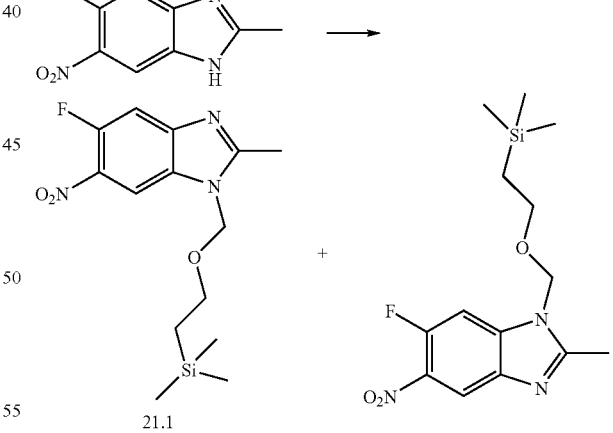

5-Fluoro-2-methyl-6-nitro-1-((2-(trimethylsilyl)ethoxy)methyl)-1H-benzo[d]imidazole and 6-fluoro-2-methyl-5-nitro-1-((2-(trimethylsilyl)ethoxy)methyl)-1H-benzo[d]imidazole (21.1). Under an N$_2$ atmosphere, 5-fluoro-2-methyl-6-nitro-1H-benzo[d]imidazole (0.491 g, 2.52 mmol) was suspended in tetrahydrofuran (8 mL) and cooled to 0° C. Sodium hydride (65% dispersion in mineral oil, 0.063 g, 2.64 mmol) was added and the reaction was allowed to stir for 15 min. at 0° C. The reaction was treated with (0.578 mL, 3.28 mmol) and stirred overnight at room temperature. The reaction was diluted with ethyl acetate and saturated NH₄Cl (aq). The layers were separated and the aqueous layer was washed with additional ethyl acetate. The organics were combined, dried (Na₂SO₄), and concentrated in vacuo. Flash column chromatography of the residue, eluting with 20% to 80% ethyl acetate in hexanes, afforded the title compound. ¹H NMR (500 MHz) (CDCl₃) δ 8.43 (d, J=6.7 Hz, 1H); 8.23 (d, J=6.3 Hz, 1H); 7.53 (d, J=11.3 Hz, 1H); 7.29 (m, 1H); 5.53 (s, 2H); 5.49 (s, 2H); 3.61-3.55 (m, 4H); 2.72 (s, 3H); 2.71 (s, 3H); 0.98-0.93 (m, 4H); 0.00 (s, 18H). Isomers were not separated and carried through the sequence as a mixture until deprotection which then generated a single compound.

Scheme 21.2

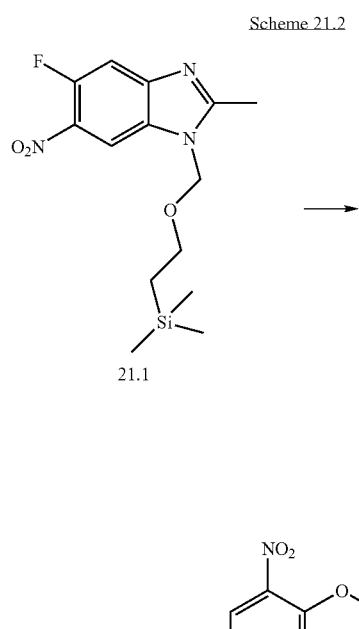

21.1

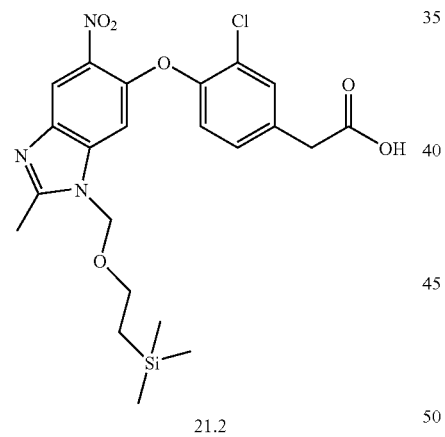

21.2

2-(3-Chloro-4-(2-methyl-6-nitro-3-((2-(trimethylsilyl) ethoxy)methyl)-3H-benzo[d]imidazol-5-yloxy)phenyl)acetic acid. (21.2). Under an N₂ atmosphere, 3-chloro-4-hydroxyphenylacetic acid (0.191 g, 1.02 mmol) was suspended in DMSO (4 mL) and cesium carbonate (0.303 g, 2.55 mmol) was added. 5-Fluoro-2-methyl-6-nitro-1-((2-(trimethylsilyl) ethoxy)methyl)-1H-benzo[d]imidazole (0.303 g, 0.931 mmol) was added and the reaction was heated to 80° C. overnight. The reaction was diluted with diethyl ether and 20% citric acid (aq). The layers were separated and the aqueous layer was washed with additional diethyl ether. The organics were combined, dried (Na₂SO₄), filtered, and concentrated in vacuo, afforded the title compound. LC-MS ESI (pos.) m/z: 492.1 (M+H).

Scheme 21.3

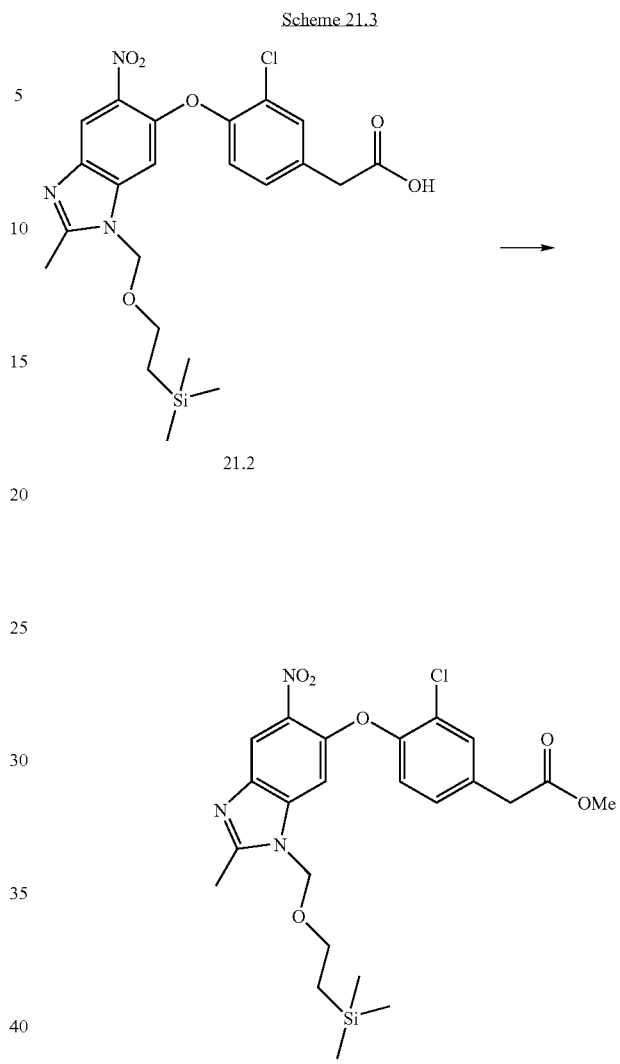

Methyl 2-(3-chloro-4-(2-methyl-6-nitro-3-((2-(trimethylsilyl)ethoxy)methyl)-3H-benzo[d]imidazol-5-yloxy)phenyl) acetate (21.3). Under an N₂ atmosphere, 2-(3-Chloro-4-(2-methyl-6-nitro-3-((2-(trimethylsilyl)ethoxy)methyl)-3H-benzo[d]imidazol-5-yloxy)phenyl)acetic acid (0.376 g, 0.764 mmol) was dissolved in DMF (3 mL). Cesium carbonate (0.274 g, 0.841 mmol) was added and the reaction was stirred at room temperature for 5 min. Iodomethane (0.052 mL, 0.841 mmol) was added and the reaction was allowed to stir at room temperature for 16 h. The reaction was diluted with diethyl ether and washed with water. The layers were separated and the aqueous layer was washed with additional diethyl ether. The organics were combined, dried (Na₂SO₄), filtered and concentrated in vacuo. Flash column chromatography of the residue, eluting with 10% to 30% isopropanol in hexanes, afforded the title compound. LC-MS ESI (pos.) m/z: 506.0 (M+H).

Scheme 21.4

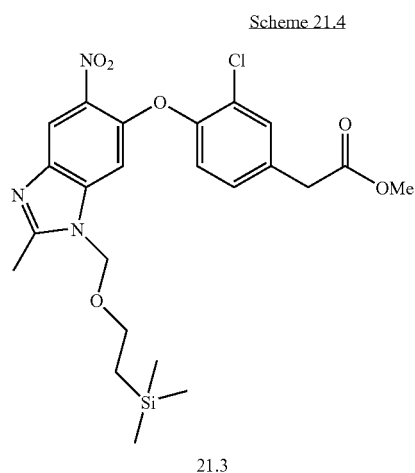

21.3

Scheme 21.5

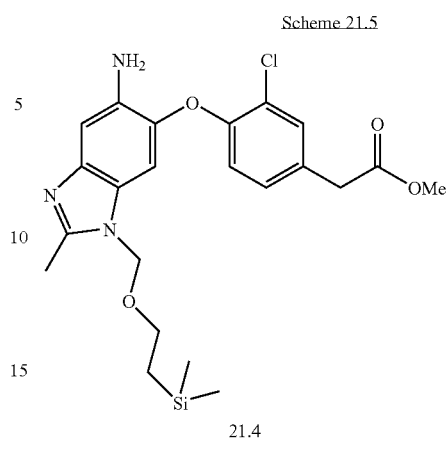

21.4

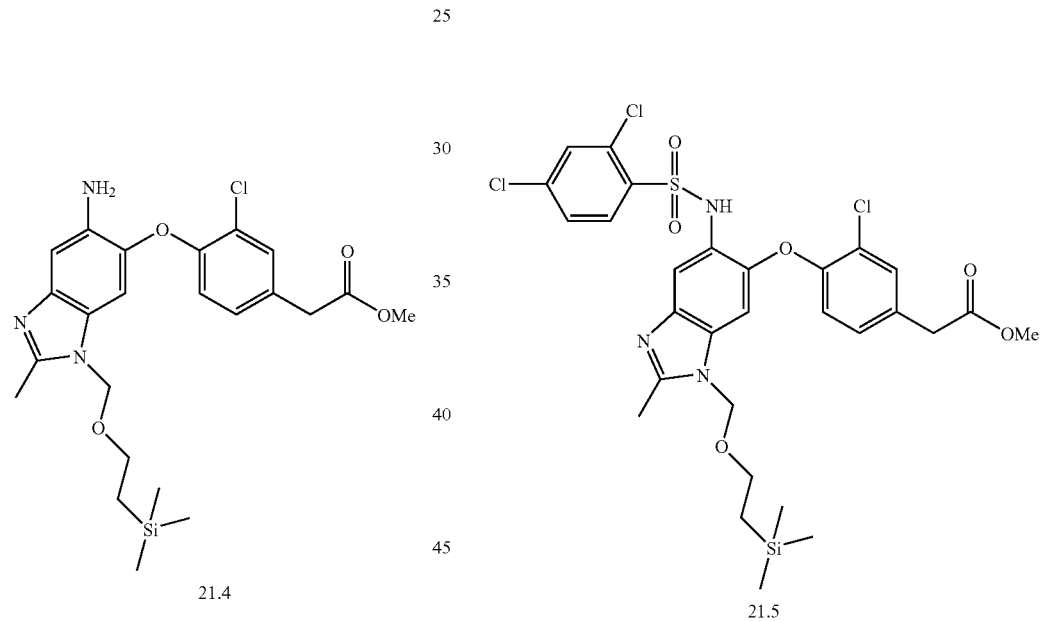

Methyl 2-(4-(6-amino-2-methyl-3-((2-(trimethylsilyl)ethoxy)methyl)-3H-benzo[d]imidazol-5-yloxy)-3-chlorophenyl)acetate (21.4). Under an N₂ atmosphere, methyl 2-(3-chloro-4-(2-methyl-6-nitro-3-((2-(trimethylsilyl)ethoxy)methyl)-3H-benzo[d]imidazol-5-yloxy)phenyl)acetate (0.220 g, 0.435 mmol) was dissolved in ethyl acetate (10 mL) and tin chloride dihydrate (0.392 g, 0.174 mmol) was added. The reaction was allowed to stir at room temperature for 2.5 h. The reaction was diluted with 10% NaHCO₃ (aq) and ethyl acetate. The layers were separated and the organic layer was washed with brine, dried (Na₂SO₄), and concentrated in vacuo, afforded the title compound. LC-MS ESI (pos.) m/z: 476.0 (M+H).

Methyl 2-(3-chloro-4-(6-(2,4-dichlorophenylsulfonamido)-2-methyl-3-((2-trimethylsilyl)ethoxy)methyl)-3H-benzo[d]imidazol-5-yloxy)phenyl)acetate (21.5). Under an N₂ atmosphere, methyl 2-(4-(6-amino-2-methyl-3-((2-(trimethylsilyl)ethoxy)methyl)-3H-benzo[d]imidazol-5-yloxy)-3-chlorophenyl)acetate (0.191 g, 0.401 mmol) was dissolved in pyridine (4 mL) and 2,4-dichlorobenzenesulfonyl chloride (0.108 g, 0.441 mmol) was added. The reaction was allowed to stir at room temperature for 16 h. The reaction was concentrated in vacuo, and the resulting oil was partitioned between ethyl acetate and saturated NH₄Cl (aq). The layers were separated and the aqueous layer was washed with additional ethyl acetate. The organics were combined, dried (Na₂SO₄), filtered, and concentrated in vacuo. Flash column chromatography of the residue, eluting with 0% to 2% methanol in dichloromethane, afforded the title compound. LC-MS ESI (pos.) m/z: 685.9 (M+H).

Scheme 21.6

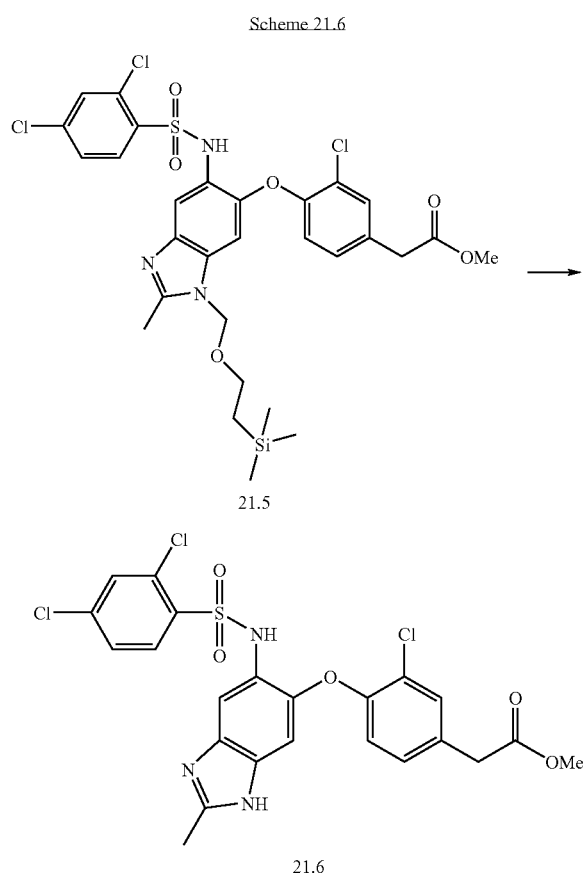

Methyl 2-(3-chloro-4-(6-(2,4-dichlorophenylsulfonamido)-2-methyl-3H-benzo[d]imidazol-5-yloxy)phenyl)acetate (21.6). Under an $N_2$ atmosphere, methyl 2-(3-chloro-4-(6-(2,4-dichlorophenylsulfonamido)-2-methyl-3-((2-(trimethylsilyl)ethoxy)methyl)-3H-benzo[d]imidazol-5-yloxy)phenyl)acetate (0.245 g, 0.358 mmol) was dissolved in dichloromethane (4.0 mL). Trifluoroacetic acid (2.5 mL) was added and the reaction was allowed to stir overnight at room temperature. The reaction was diluted with ethyl acetate and saturated $NaHCO_3$ (aq). The layers were separated and the organic layer was dried ($Na_2SO_4$), filtered and concentrated in vacuo. Flash column chromatography of the residue, eluting 0% to 7% methanol in dichloromethane, afforded the title compound. LC-MS ESI (pos.) m/z: 555.8 (M+H).

Scheme 21.7

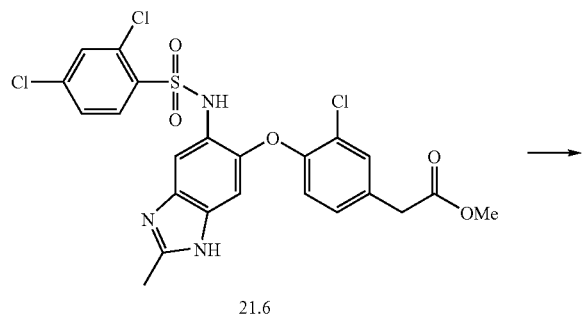

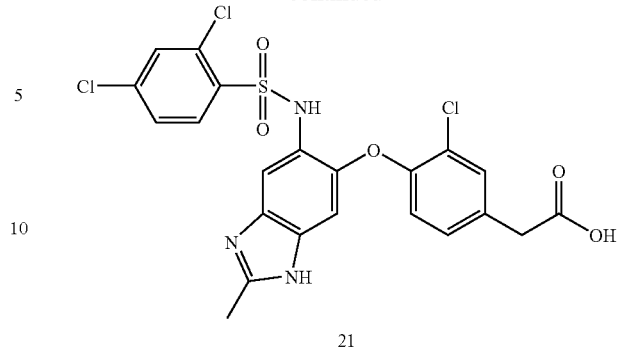

2-(3-Chloro-4-(6-(2,4-dichlorophenylsulfonamido)-2-methyl-3H-benzo[d]imidazol-5-yloxy)phenyl)acetic acid (21). Under an $N_2$ atmosphere, methyl 2-(3-chloro-4-(6-(2,4-dichlorophenylsulfonamido)-2-methyl-3H-benzo[d]imidazol-5-yloxy)phenyl)acetate (0.138 g, 0.248 mmol) was dissolved in THF (2.5 mL), and 1N LiOH (2.5 mL) was added. The reaction was allowed to stir at room temperature for 2.5 h. The reaction was brought to pH 5 with 1N HCl and extracted with ethyl acetate. The organic layer was dried ($Na_2SO_4$), filtered and concentrated in vacuo. The residue was triturated with an ethyl acetate/hexanes mixture and the product was collected by filtration. LC-MS ESI (pos.) m/z: 541.9 (M+H). $^1$H NMR (400 MHz) (DMSOd-$_6$) δ 7.76 (d, J=8.5 Hz, 1H); 7.64 (d, J=1.8 Hz, 1H); 7.62 (s, 1H), 7.43-7.40 (m, 2H); 7.10 (d, J=8.2 Hz, 1H); 6.77 (s, 1H); 6.57 (d, J=8.3 Hz, 1H); 3.59 (s, 2H); 2.61 (s, 3H).

7.21. Example 22

This example illustrates the preparation 2-(4-(4-(2,4-dichlorophenylsulfonamido)-1H-indazol-5-yloxy)-3-methoxyphenyl)acetic acid (22).

Scheme 22.1

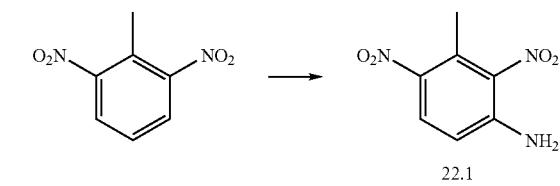

2,4-Dinitro-3-methylaniline (22.1). A mixture of 2,6-dinitrotoluene (28 g, 0.15 mol) and hydroxylamine hydrochloride (28 g, 0.15 mol) was stirred in ethanol (700 mL) until completely dissolved. 2N potassium hydroxide solution in methanol (275 mL) was added all at once and the resulting mixture allowed to stir overnight at room temperature. After this time a solution of ammonium chloride (36 g) in water (175 mL) was added and the mixture stirred for an additional hour. The reaction mixture was evaporated under reduced pressure and the residue partitioned between ethyl acetate (300 mL) and saturated brine (250 mL). The ethyl acetate layer was separated, dried over magnesium sulfate and concentrated under reduced pressure. Flash chromatography of the residue (ethyl acetate/hexane (2:1)) afforded the desired product. $^1$H NMR (400 MHz) (CDCl$_3$) δ 7.98 (d, J=9.4 Hz, 1H); 6.73 (d, J=9.4 Hz, 1H); 5.50 (bs, 2H); 2.59 (s, 3H).

Scheme 22.2

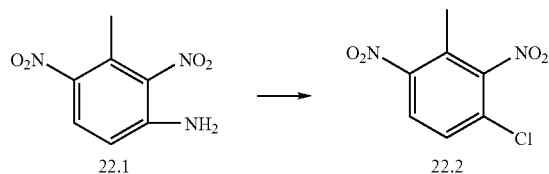

3-Chloro-2,6-dinitrotoluene (22.2). To a stirred mixture of copper (II) chloride (1.56 g, 11.5 mmol) and dry acetonitrile at 60-65° C. was added t-butyl nitrite (1.72 mL, 14.4 mmol) in one portion. 2,4-dinitro-3-methylaniline (1.89 g, 9.5 mmol) was then added gradually to this mixture. The mixture was stirred at 65° C. for a further 15 min, then cooled to room temperature and concentrated under reduced pressure. The residue was partitioned between diethyl ether (100 mL) and 6N aqueous HCl solution (100 mL). The organic layer was separated, washed with brine (100 mL), dried over MgSO4 and concentrated under reduced pressure. Flash chromatography of the residue (diethyl ether) afforded the product as a yellow solid. $^1$H NMR (400 MHz) (CDCl$_3$) δ 8.9 (d, J=8.9 Hz, 1H); 7.61 (d, J=8.9 Hz, 1H); 2.51 (s, 3H).

Scheme 22.3

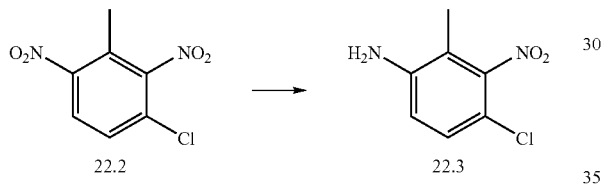

4-Chloro-2-methyl-3-nitroaniline (22.3). A mixture of 3-chloro-2,6-dinitrotoluene (2.46 g, 9.5 mmol), cyclohexene (10 mL) and 10% palladium on charcoal (0.6 g) in ethanol (50 mL) was heated at reflux under an atmosphere of nitrogen for 2 h. After this time the reaction mixture was cooled to room temperature, filtered through celite and then evaporated under reduced pressure. The residue was dissolved in diethyl ether and filtered through a short silica column. Evaporation of the ether afforded the product as an orange solid. $^1$H NMR (400 MHz) (CDCl$_3$) δ 7.15 (d, J=8.7 Hz, 1H); 6.72 (d, J=8.7 Hz, 1H); 3.80 (bs, 2H); 2.11 (s, 3H).

Scheme 22.4

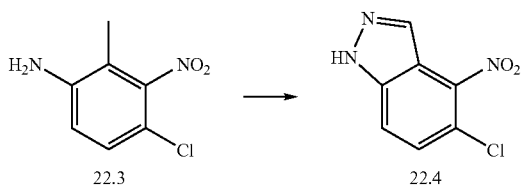

4-Nitro-5-chloroindazole (22.4). To 4-chloro-2-methyl-3-nitroaniline (1.63 g, 8.8 mmol) dissolved in acetic acid (75 mL) at room temperature was added a 2M aqueous solution of sodium nitrite (4.4 mL). The suspension was then diluted with acetic acid (100 mL) and then heated at reflux for 4 h. The mixture was then cooled to room temperature and concentrated under reduced pressure. The residue was then partitioned between ethyl acetate (100 mL) and saturated aqueous sodium hydrogen carbonate solution (100 mL). The separated organic layer was then washed with brine, dried over magnesium sulfate and concentrated under reduced pressure. Column chromatography of the reside (hexane/ethyl acetate (2:1) afforded the desired product. $^1$H NMR (500 MHz) (DMSO-d$_6$) δ 8.32 (s, 1H); 7.95 (d, J=8.7 Hz, 1H); 7.68 (d, J=8.7 Hz, 1H).

Scheme 22.5

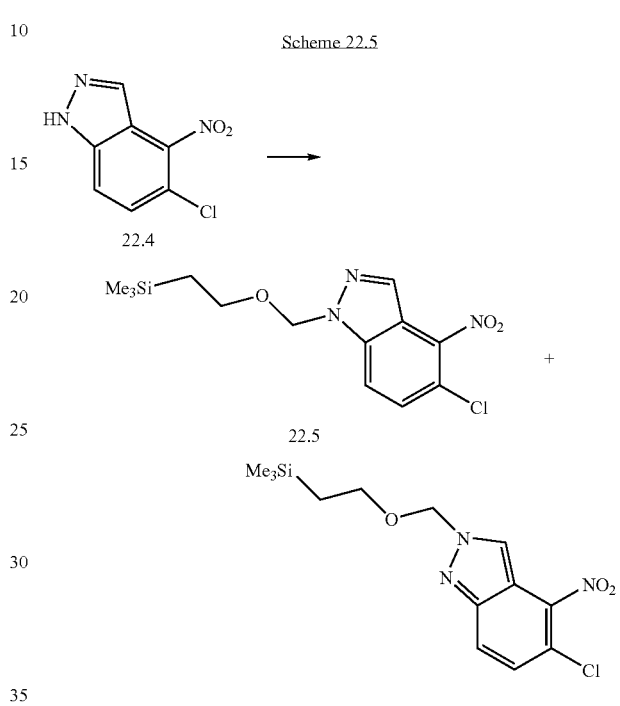

5-Chloro-4-nitro-1-(2-(trimethylsilyl)ethoxy)methyl)-1H-indazole (22.5). 4-nitro-5-chloroindazole (0.185 g, 0.94 mmol) was dissolved in DMF and cooled to 0° C. Sodium hydride (60% suspension in mineral oil) (38 mg, 0.95 mmol) and 2-(trimethylsilyl)ethoxymethyl chloride (165 mL, 0.94 mmol) were added. After 10 min. the mixture was quenched with water and then extracted with ethyl acetate (3×25 mL). The combined organic extracts were washed with brine, dried over magnesium sulfate and concentrated under reduced pressure. The two isomers of the product were separated by column chromatography to give the title compound and its 2-SEM-isomer. $^1$H NMR (400 MHz) (CDCl$_3$) δ 8.32 (s, 1H); 7.80 (d, J=8.85 Hz, 1H); 7.58 (d, J=8.85 Hz, 1H); 5.81 (s, 2H); 3.58 (t, J=8.3 Hz, 2H); 0.93 (t, J=8.3 Hz, 2H); 0.0 (s, 9H).

5-Chloro-4-nitro-2-((2-(trimethylsilyl)ethoxy)methyl)-1H-indazole. $^1$H NMR (400 MHz) (CDCl$_3$) δ 8.51 (s, 1H); 7.95 (d, J=9.0 Hz, 1H); 7.44 (d, J=9.0, 1H); 5.77 (s, 2H); 3.69 (t, J=8.2, 2H); 1.0 (t, J=8.2, 2H); 0.0 (s, 9H).

Scheme 22.6

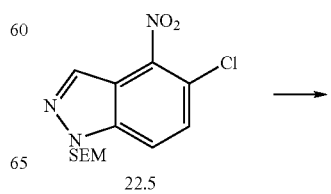

-continued

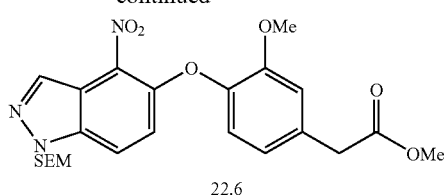

22.6

Methyl 2-(3-methoxy-4-(4-nitro-1-((2-(trimethylsilyl) ethoxy)methyl)-1H-indazol-5-yloxy)phenyl)acetate (22.6). To methyl-3-methoxy-4-hydroxyphenylacetate (0.062 g, 0.32 mmol) in dry THF (5 mL) under nitrogen was added sodium hexamethyldisylazide (1M solution in THF) (312 μl, 0.31 mmol). After 10 min. stirring at room temperature 5-chloro-4-nitro-1-((2-(trimethylsilyl)ethoxy)methyl)-1H-indazole (93 mg, 0.28 mmol) in 5 mL of THF was added. The resulting mixture was stirred at reflux for 5 days. After that time the mixture was quenched with water and extracted with ethyl acetate (3×25 mL). The combined organic extracts were washed with brine, dried over magnesium sulfate and concentrated under reduced pressure. The desired product was isolated by chromatography (10% ethyl acetate/hexane). $^1$H NMR (400 MHz) (CDCl$_3$) δ 8.40 (s, 1H); 7.70 (d, J=9.1 Hz, 1H); 7.05 (d, J=9.1 Hz, 1H); 6.95 (m, 2H), 6.84 (dd, J=1.5, 8.0 Hz, 1H); 5.75 (s, 2H); 3.82 (s, 3H), 3.62, s, 3H); 3.62 (s, 2H); 3.57 (t, J=8.0 Hz, 2H); 0.89 (t, J=8.0 Hz, 2H); 0.0 (s, 9H).

Scheme 22.7

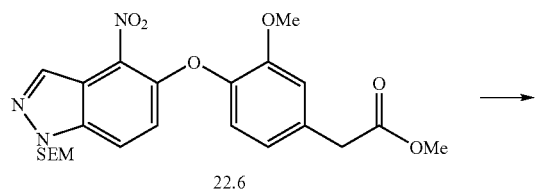

Methyl 2-(4-(4-amino-1-((2-(trimethylsilyl)ethoxy)methyl)-1H-indazol-5-yloxy)-3-methoxyphenyl)acetate (22.7). To a solution of methyl 2-(3-methoxy-4-(4-nitro-1-((2-(trimethylsilyl)ethoxy)methyl)-1H-indazol-5-yloxy)phenyl)acetate (46 mg, 0.09 mmol) was added a catalytic amount of 10% palladium on carbon. The resulting mixed was stirred under an atmosphere of hydrogen for 45 min. After that time the reaction mixture was filtered through celite and concentrated under reduced pressure to give the product as a pale solid. $^1$H NMR (400 MHz) (CDCl$_3$) δ 7.97 (s, 1H); 7.08 (d, J=8.8, 1H); 6.93 (d, J=1.8, 1H); 6.91 (d, J=8.8, 1H); 6.76 (dd, J=1.8, 8.2, 1H); 6.65 (d, J=8.2, 1H); 5.70 (s, 2H); 4.28 (bs, 2H); 3.95 (s, 3H); 3.71 (s, 3H), 4.58 (m, 4H); 0.92 (t, J=8.2, 2H), 0.0 (s, 9H).

Scheme 22.8

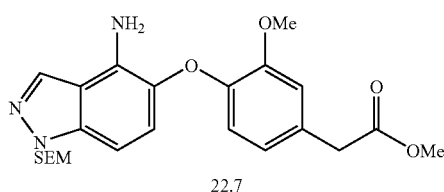

22.7

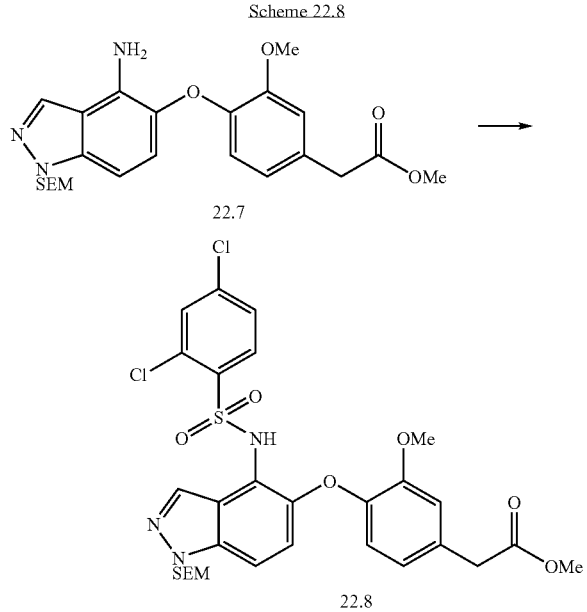

22.8

Methyl 2-(4-(4-(2,4-dichlorophenylsulfonamido)-1-((2-(trimethylsilyl)ethoxy)methyl)-1H-indazol-5-yloxy)-3-methoxyphenyl)acetate (22.8). To a solution of methyl 2-(4-(4-amino-1-((2-(trimethylsilyl)ethoxy)methyl)-1H-indazol-5-yloxy)-3-methoxyphenyl)acetate (42 mg, 0.092 mmol) in dichloromethane (1 mL) was added 2,4-dichlorobenzene sulfonyl chloride (25 mg, 0.1 mmol) and pyridine (10 μl, 0.12 mmol). The resulting mixture was stirred overnight at room temperature. The mixture was then diluted with dichloromethane (20 mL) and washed with dilute aqueous hydrochloric acid (20 mL) and water (20 mL), then dried over magnesium sulfate and concentrated under reduced pressure. The desired sulfonamide was isolated by column chromatography (10% ethyl acetate/hexane). $^1$H NMR (400 MHz) (CDCl$_3$) δ 8.40 (s, 1H); 7.81 (s, 1H); 7.72 (d, J=8.5 Hz, 1H); 7.32 (d, J=9 Hz, 1H); 7.19 (d, J=1.9 Hz, 1H); 7.15 (dd, J=1.9, 8.5 Hz, 1H); 6.90 (d, J=1.8 Hz, 1H); 6.88 (d, J=9 Hz, 1H); 6.60 (dd, J=1.8, 8.2 Hz, 1H); 6.35 (d, J=8.2 Hz, 1H); 5.68 (s, 2H); 3.84 (s, 3H); 3.75 (s, 3H), 3.62 (s, 2H); 3.57 (t, J=8.2 Hz, 2H); 0.89 (t, J=8.2 Hz, 2H), 0.0 (s, 9H).

Scheme 22.9

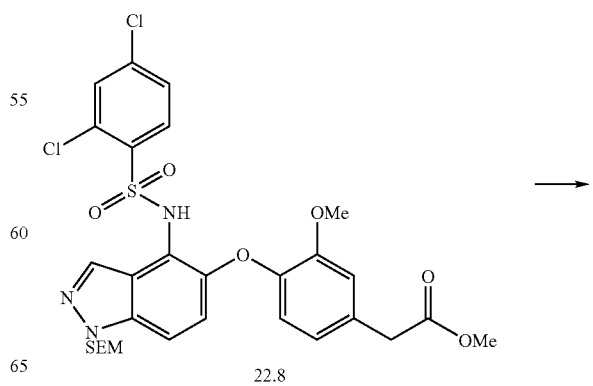

22.8

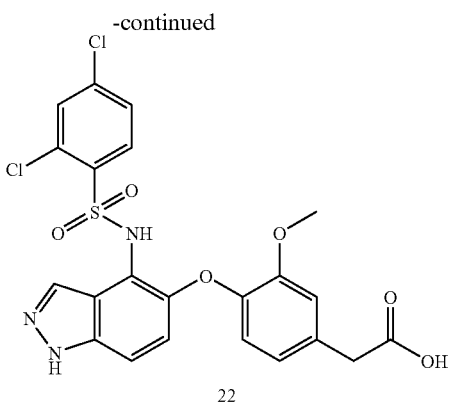

2-(4-(4-(2,4-Dichlorophenylsulfonamido)-1H-indazol-5-yloxy)-3-methoxyphenyl)acetic acid (22). To a solution of methyl 2-(4-(4-(2,4-dichlorophenylsulfonamido)-1-((2-(trimethylsilyl)ethoxy)methyl)-1H-indazol-5-yloxy)-3-methoxyphenyl)acetate (45 mg, 0.06 mmol) in ethanol (2 mL) was added 6N aqueous hydrochloric acid (1 mL). The resulting solution was heated at reflux for 3 h. After that time the mixture was cooled to room temperature and concentrated under reduced pressure and the residue taken up in THF (3 mL) and an excess of 2N aqueous lithium hydroxide added. The mixture was stirred at reflux for 1 h, then cooled to room temperature. The mixture was concentrated under reduced pressure. Column chromatography of the residue (1-5% MeOH/DCM with 0.1% AcOH) afforded the product as a cream solid. LC-MS ESI (pos.) m/e: 523 (M+H). $^1$H NMR (500 MHz) (d$^6$DMSO) δ 11.20 (s, 1H); 10.25 (s, 1H); 7.96 (s, 1H); 7.68 (d, J=8 Hz, 1H); 7.56 (s, 1H), 7.35 (m, 2H); 6.93 (s, 1H), 6.70 (d, J=9 Hz, 1H); 6.61 (d, J=8 Hz, 1H); 6.24 (d, J=9 Hz, 1H); 3.70 (s, 3H); 3.55 (s, 2H).

7.22. Example 23

This example illustrates the preparation 2-(3-chloro-4-(4-(2,4-dichlorophenylsulfonamido)-2-oxoindolin-5-yloxy)phenyl)acetic acid (23).

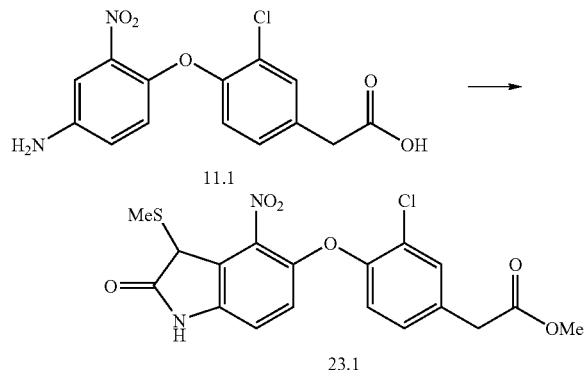

Methyl 2-(3-chloro-4-(3-(methylthio)-4-nitro-2-oxoindolin-5-yloxy)phenyl)acetate (23.1). To a solution of 2-(4-(4-amino-2-nitrophenoxy)-3-chlorophenyl)acetic acid (11.1) (3.22 g, 10 mmol) in anhydrous benzene (40 mL) and MeOH (10 mL) was slowly added 2N solution of TMSCHN$_2$ in ether (10 mL, 20 mmol), stirred at 25° C. for 1 h, concentrate to give the methyl ester. The methyl ester was redissolved in DCM (30 mL) and was cooled to −65° C. t-Butylhypochlorite (1.14 mL, 10 mmol) in 5 mL of DCM was added dropwise at −65° C. and stirred at the same temperature for 5 min. Ethyl methylthioacetate (1.28 mL, 10 mmol) in 5 mL of DCM was then added dropwise at −65° C. and stirred at the same temperature for 1 h. Triethylamine (1.4 mL, 10 mmol) in was added slowly at −65° C. and the reaction mixture was allowed to warm to 25° C. by removing the cooling bath. A 10-mL portion of water was added, and the organic layer was separated and evaporated. The residue was redissolved in 30 mL of ethyl ether, treated with 5 mL of 2N aqueous HCl, and stirred overnight at 25° C. The resulting suspension was filtered, and the filtrate was rinsed with water to give the desired product (23.1). Flash chromatography (silica gel, 20% EtOAc in hexanes as eluant) afforded 23.1 as a yellow solid. MS ESI (pos.) m/e calcd for (M+H)$^+$ 423.0. found 423.1. $^1$H NMR (500 MHz) (CDCl$_3$) δ 10.98 (s, 1H); 7.53 (s, 1H); 7.27 (d, J=8.4 Hz, 1H); 7.11 (d, J=8.6 Hz, 1H); 7.06 (d, J=8.7, 1H); 7.04 (d, J=8.4 Hz, 1H); 4.88 (s, 1H); 3.74 (s, 2H); 3.64 (s, 3H); 1.92 (s, 3H).

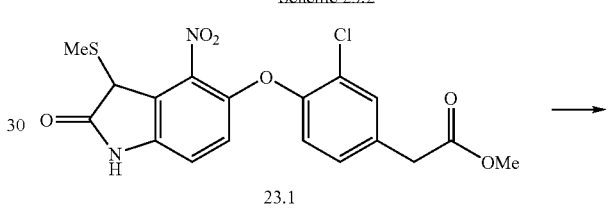

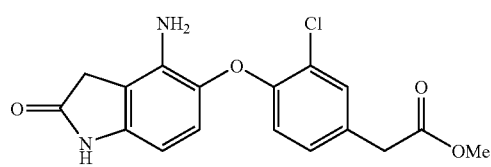

Methyl 2-(4-(4-amino-2-oxoindolin-5-yloxy)-3-chlorophenyl)acetate (23.2). To a solution of W.1 (422 mg, 1 mmol) in absolute EtOH (10 mL) was added Raney-Nickel (9 g, Raney 2800 nickel, slurry in water), stirred at 25° C. for 16 h. The suspension was filtered, rinsed with EtOH, concentrated to give 23.2 as brown solid. MS ESI (pos.) m/e calcd for (M+H)$^+$ 347.1. found 347.1.

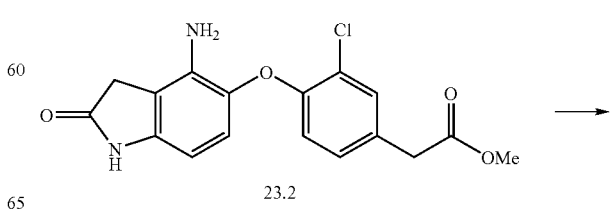

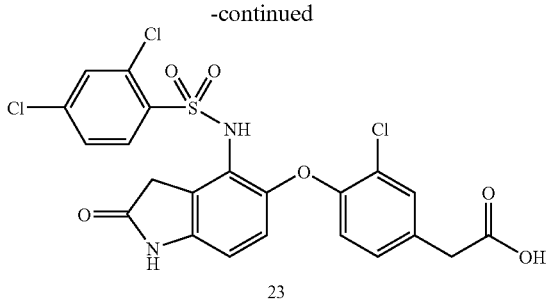

2-(3-Chloro-4-(4-(2,4-dichlorophenylsulfonamido)-2-oxoindolin-5-yloxy)phenyl)acetic acid (23). 23.2 (35 mg, 0.1 mmol) and 2,4-dichlorobenzenesulfonyl chloride (52 mg, 0.21 mmol) were stirred in pyridine (0.5 mL) at 25° C. for 4 h. The reaction mixture was loaded directly to a prepacked Redisep Column and flash chromatographed (gradient, 0-100% EtOAc in Hexanes) to give the sulfonamide, which was then hydrolyzed in MeOH/THF/water (0.3 mL each) with LiOH (7 mg, 0.3 mmol) at 25° C. for 2 h. Reverse phase HPLC (C18, 10-90% ACN in water with 0.1% TFA as eluant) of the reaction mixture afforded 23 as a yellow solid. MS ESI (pos.) m/e calcd for (M+H)$^+$ 543.0.1. found 543.0. $^1$H NMR (500 MHz) (CDCl$_3$) δ 12.45 (br. s, 1H); 10.47 (s, 1H); 10.08 (s, 1H); 7.73 (d, J=8.5 Hz, 1H); 7.58 (s, 1H); 7.34 (d, J=8.5 Hz, 1H); 7.33 (s, 1H); 7.04 (d, J=7.8, 1H); 6.71 (d, J=8.3 Hz, 1H); 6.54 (d, J=8.1 Hz, 1H); 6.43 (d, J=8.3 Hz, 1H); 3.57 (s, 2H); 3.56 (s, 2H).

7.23. Example 24

This example illustrates the preparation of 2-(4-(5-(4-chlorophenylsulfonamido)quinolin-6-yloxy)-3-methoxyphenyl)acetic acid (24).

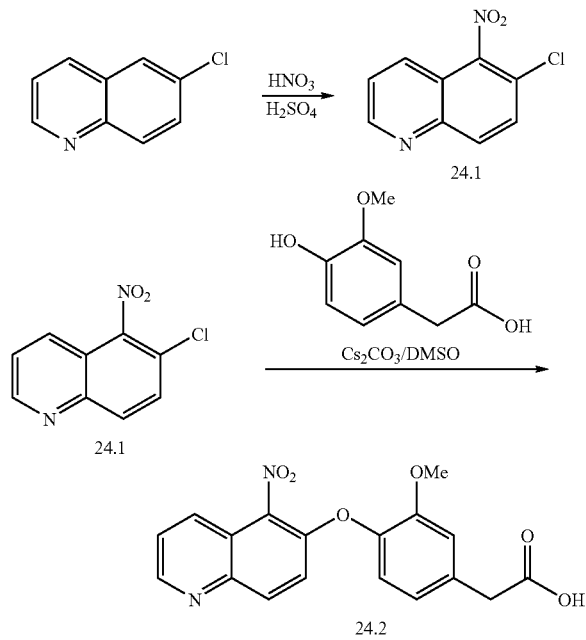

6-Chloro-5-nitroquinoline (24.1). HNO$_3$ (90%, 7 mL) was added to 6-chloro-quinoline (4.45 g) in concentrated sulfuric acid (21 mL) at 0° C. The mixture was stirred at 0° C. for 1 h and at room temperature overnight. The reaction mixture was poured into ice, and the solid product (24.1) was collected by filtration, washed with water and dried. MS ESI (pos.) m/z: 209.0 (M+H).

2-(3-Methoxy-4-(5-nitroquinolin-6-yloxy)phenyl)acetic acid (24.2). Cs$_2$CO$_3$ (15.5 g, 47.5 mmol) was added to (24.1) (3 g, 14.4 mmol) and 3-methoxy-4-hydroxyphenylacetic acid (2.63 g, 14.4 mmol) in DMSO (30 mL) at room temperature. The mixture was then stirred at 80° C. for 4 h. After cooling, the reaction mixture was treated with water (50 mL), 3N HCl (35 mL) and EtOAc (100 mL). The product was insoluble in EtOAc, but stayed in the organic layer. So the organic layer was washed with water 4 times to get rid of all the salts, and the organic layer was separated, concentrated and dried under vacuum to afford 24.2. MS ESI (pos.) m/z: 355.1 (M+H). $^1$H NMR (DMSO-d$_6$) δ 8.99 (dd, 1H); 8.24 (m, 2H); 7.77 (dd, 1H); 7.29 (d, 1H); 7.21 (d, 1H); 7.18 (d, 1H); 6.96 (dd, 1H); 3.73 (s, 3H); 3.65 (s, 2H).

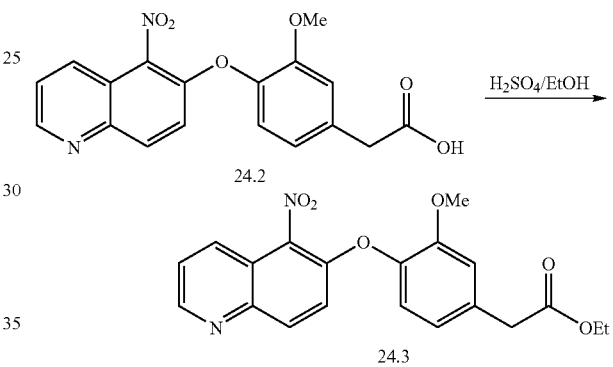

Ethyl 2-(3-methoxy-4-(5-nitroquinolin-6-yloxy)phenyl)acetate (24.3). Concentrated sulfuric acid (0.32 mL, 11.3 mmol) was added to 24.2 (4 g, 11.3 mmol) in EtOH. The mixture was heated to reflux for 15 h. After cooling, EtOH was evaporated under vacuum, and the residue was treated with EtOAc (100 mL). Saturated NaHCO$_3$ was added to neutralize the acid. The organic layer was separated, dried with MgSO$_4$ and concentrated to give 24.3. MS ESI (pos.) m/z: 383.1 (M+H). $^1$H NMR (DMSO-d$_6$) δ 8.99 (dd, 1H); 8.24 (m, 2H); 7.77 (dd, 1H); 7.29 (d, 1H); 7.21 (d, 1H); 7.18 (d, 1H); 6.96 (dd, 1H); 4.13 (q, 2H); 3.73 (s, 5H); 1.23 (t, 3H).

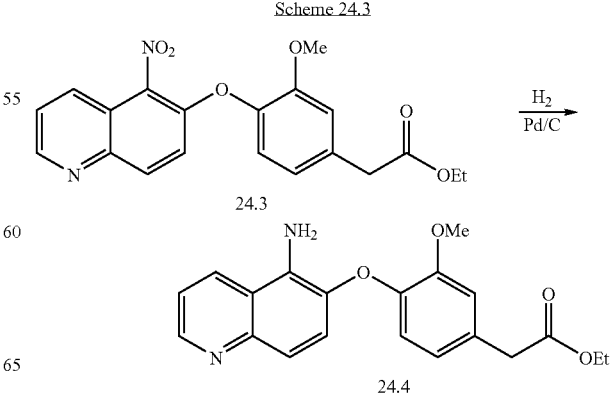

-continued

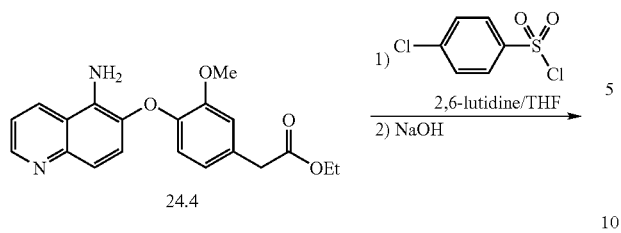 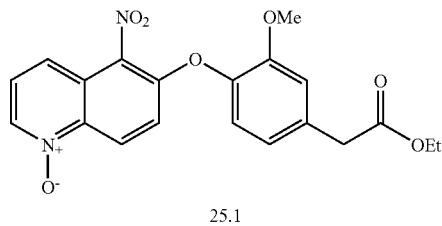

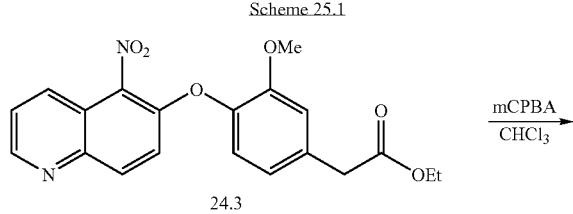

Ethyl 2-(4-(5-aminoquinolin-6-yloxy)-3-methoxyphenyl)acetate (24.4). Pd/C (30 mg) was added to 24.3 (310 mg) in EtOH (10 mL). The mixture was stirred under hydrogen at room temperature for 6 h. The catalyst was removed by filtration through celite. The filtrate was concentrated under vacuum to give 24.4. MS ESI (pos.) m/z: 353.1 (M+H).

2-(4-(5-(4-Chlorophenylsulfonamido)quinolin-6-yloxy)-3-methoxyphenyl)acetic acid (24). To 24.4 (36 mg, 0.1 mmol) and 2,6-lutidine (0.024 mL, 0.2 mmol) in THF (0.5 mL) was added 4-chlorobenzenesulfonyl chloride (26 mg, 0.12 mmol). The mixture was stirred at 70° C. overnight. After cooling, water (1 mL) and 10N NaOH (0.5 mL) were added. The mixture was stirred at room temperature for 5 h. 3N HCl (1.7 mL) and EtOAc were added to the mixture, and the organic layer was separated, dried with MgSO$_4$ and concentrated. Flash column chromatography of the residue afforded 24. MS ESI (pos.) m/z: 499.1 (M+H). $^1$H NMR (DMSO-d$_6$) δ 10.2 (bs, 1H), 8.82 (d, 1H); 8.50 (d, 1H); 7.92 (d, 1H); 7.71 (d, 2H); 7.61 (dd, 1H); 7.55 (d, 2H); 7.03 (d, 1H); 6.95 (d, 1H); 6.79 (dd, 1H); 6.38 (d, 1H); 3.73 (s, 3H); 3.58 (s, 2H).

7.24. Example 25

This example illustrates the preparation of 2-(4-(5-(4-chlorophenylsulfonamido)-2-oxo-1,2-dihydroquinolin-6-yloxy)-3-methoxyphenyl)acetic acid (25).

Ethyl 2-(3-methoxy-4-(5-nitro-1N-oxide-quinolin-6-yloxy)phenyl)acetate (25.1). mCPBA (70-75%, 1.5 g, ~5.9 mmol) was added to 24.3 (1.5 g, 3.9 mmol) in chloroform (12 mL). The mixture was stirred at room temperature overnight. DCM (50 mL) was added and it was washed with saturated NaHCO$_3$ three times. The organic layer was separated, dried with MgSO$_4$ and concentrated to give 25.1. MS ESI (pos.) m/z: 399.1 (M+H). $^1$H NMR (DMSO-d$_6$) δ 8.68 (d, 1H); 8.64 (d, 1H); 7.69 (d, 1H); 7.63 (m, 1H); 7.28 (d, 1H); 7.25 (d, 1H); 7.20 (s, 1H); 6.97 (d, 1H); 4.13 (q, 2H); 3.74 (s, 2H); 3.73 (s, 3H); 1.23 (t, 3H).

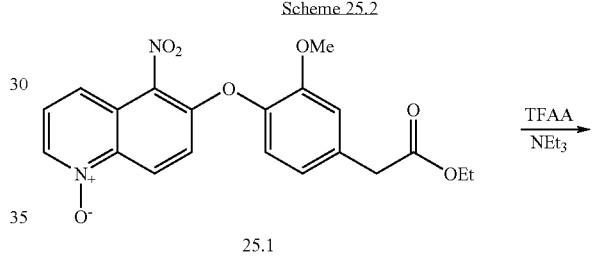

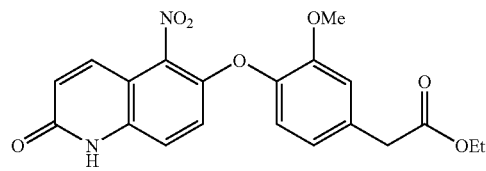

Ethyl 2-(3-methoxy-4-(5-nitro-2-oxo-1,2-dihydroquinolin-6-yloxy)phenyl)acetate (25.2). Trifluoroacetic anhydride (2.41 mL, 17.1 mmol) was added to (25.1) (680 mg, 1.71 mmol) and triethylamine (0.72 mL, 5.13 mmol) in THF at 0° C. The mixture was stirred at 0° C. for 2 h and at room temperature for 6 h. The mixture was treated with water and EtOAc. The organic layer was separated, dried with MgSO$_4$ and concentrated. Flash column chromatography of the residue afforded 25.2. MS ESI (pos.) m/z: 399.1 (M+H). $^1$H NMR (DMSO-d$_6$) δ 12.2 (s, 1H); 7.74 (d, 1H); 7.47 (d, 1H); 7.14 (d, 1H); 7.12 (d, 1H); 7.06 (d, 1H); 6.89 (dd, 1H); 6.74 (d, 1H); 4.12 (q, 2H); 3.74 (s, 3H); 3.70 (s, 2H); 1.22 (s, 3H).

Scheme 25.2

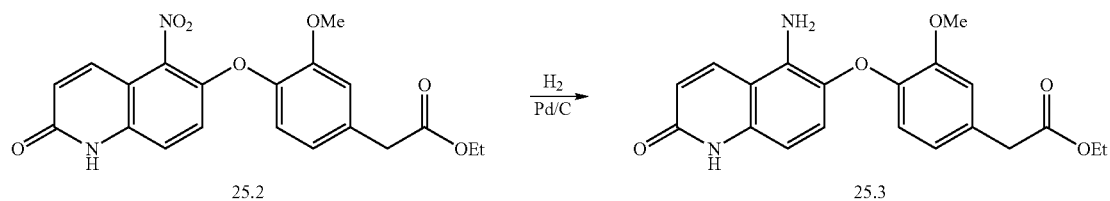

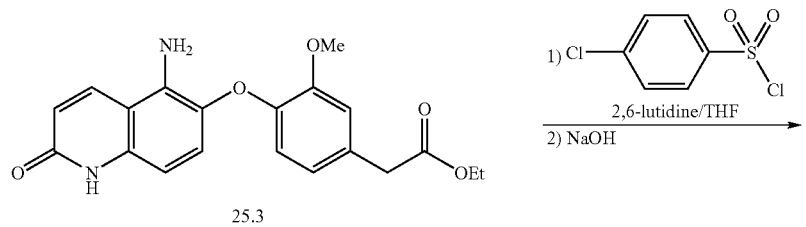

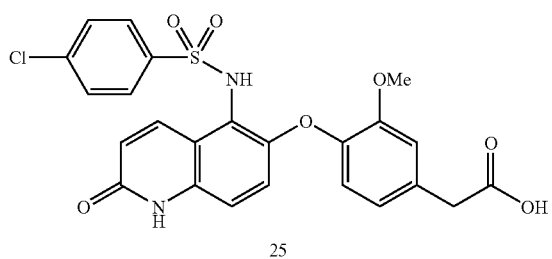

Ethyl 2-(4-(5-amino-2-oxo-1,2-dihydroquinolin-6-yloxy)-3-methoxyphenyl)acetate (25.3). Pd/C (30 mg) was added to 25.2 (250 mg) in EtOH (15 mL). The mixture was stirred under hydrogen at room temperature for 6 h. The catalyst was removed by filtration through celite. The filtrate was concentrated under vacuum to give 25.3. MS ESI (pos.) m/z: 369.1 (M+H).

2-(4-(5-(4-Chlorophenylsulfonamido)-2-oxo-1,2-dihydroquinolin-6-yloxy)-3-methoxyphenyl)acetic acid (25). To 25.3 (25 mg, 0.068 mmol) and 2,6-lutidine (0.033 mL, 0.28 mmol) in THF (0.1 mL) was added 4-chlorobenzenesulfonyl chloride (30 mg, 0.14 mmol). The mixture was stirred at 70° C. overnight. After cooling, water (0.1 mL) and 10N NaOH (0.1 mL) were added. The mixture was stirred at room temperature for 5 h. 3N HCl (0.35 mL) and EtOAc were added to the mixture, and the organic layer was separated, dried with $MgSO_4$ and concentrated. Flash column chromatography of the residue afforded 25. MS ESI (pos.) m/z: 544.1 (M+H). $^1$H NMR (DMSO-$d_6$) δ 12.32 (bs, 1H); 11.74 (s, 1H); 10.14 (s, 1H); 8.06 (d, 1H); 7.68 (d, 2H); 7.50 (d, 2H); 7.16 (d, 1H); 6.96 (s, 1H); 6.72 (m, 2H); 6.56 (d, 1H); 6.27 (d, 1H); 3.66 (s, 3H); 3.54 (s, 2H).

7.25. Example 26

This example illustrates the preparation of 2-(4-(4-(2,4-dichlorophenylsulfonamido)-7-fluoro-2-methyl-1H-indol-5-yloxy)-3-methoxyphenyl)acetic acid (26).

Scheme 26.1

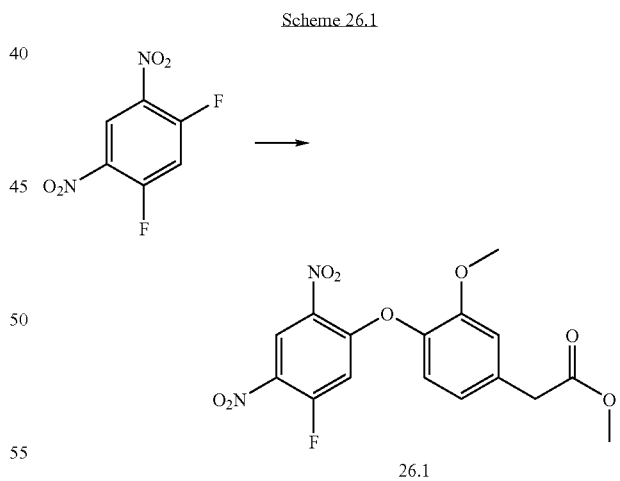

26.1. To a solution of 1,5-difluoro-2,4-dinitrobenzene (2.04 g, 10 mmol) and methyl homovanillate (1.96 g, 10 mmol) in acetonitrile (anhydrous, 30 mL) was added potassium carbonate (2.07 g, 15 mmol). After reaction was stirred for 12 h at ambient temperature, the reaction was filtered through silica gel (about 15 g), rinsed with ether and concentrated. The residue was flash chromatographed (silica gel) with 0-20% ethyl acetate in hexane to give 26.1 as pale yellow solid. MS-ESI (pos.) m/z: 381 (M+H)$^+$ Scheme 26.2

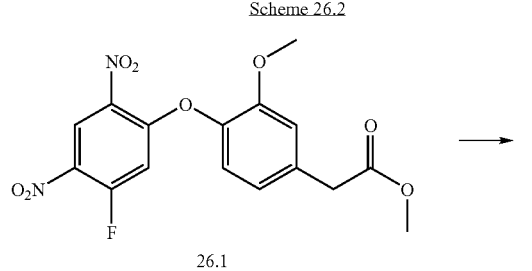

26.1

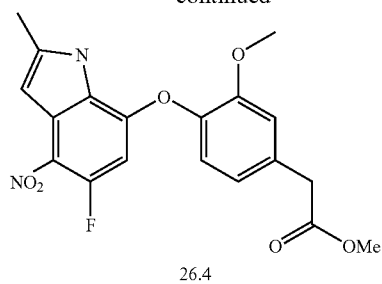

26.4

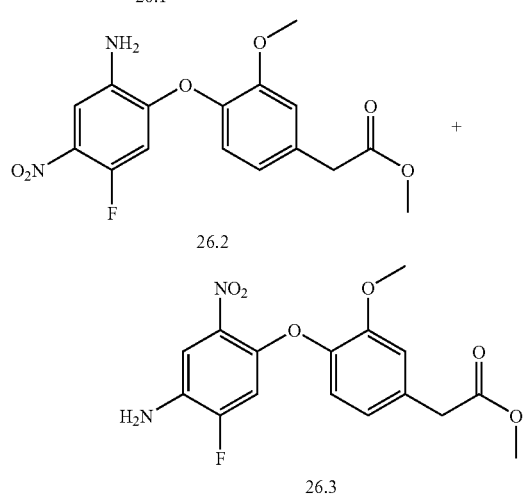

26.2

26.3

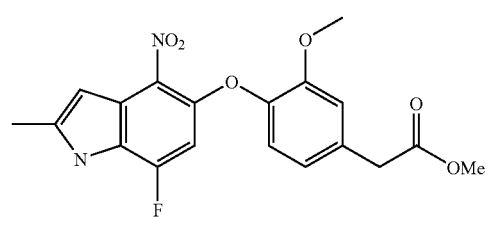

26.5

26.2/26.3. To a solution of 26.1 (3.5 g, 9.2 mmol) in THF (30 mL) was added sodium hydrosulfite (Na$_2$S$_2$O$_4$, g, 28.1 mmol) pre-dissolved in water (10 mL). The reaction was stirred for 14 h, and the mixture was poured into a mixture of ethyl acetate (100 mL) and saturated brine (20 mL). The organic layer was dried with MgSO$_4$, filtered, and concentrated under reduced pressure. The residue was flash chromatographed (silica gel, slow gradient of 0-100% DCM in hexane) to give 26.2 as the first fraction (about 1:1 mixture with 26.3), and 26.3 as the second fraction mixed with the first fraction (ratio of 26.2/26.3: 1:5). Both compounds gave MS-ESI (pos.) m/z: 351 (M+H)$^+$.

26.4/26.5. To a solution of 26.2 and 26.3 (1:1 ratio) in THF (20 mL) was added aqueous LiOH (3 mL, 11.0M). After 12 h, the reaction was neutralized with citric acid (10%, 3 mL), diluted with ethyl acetate (80 mL) and extracted with saturated brine (10 mL). The organic layer was dried with MgSO$_4$, filtered, and concentrated under vacuum thoroughly. The acid obtained this way was dissolved in DMSO (mL) cooled with an ice bath, and to it was quickly added acetone, (0.37 g, 6.3 mmol) and potassium tert-butoxide (0.71 g, 6.3 mmol) in one portion. The reaction turned dark purple immediately, and good stirring continued at 25° C. for 1 h while the reaction was open to air. The reaction was neutralized with aqueous 10% HCl (6 mL), diluted with ethyl acetate (80 mL) and extracted with water (20 mL, 3 times) and saturated brine (10 mL). The organic layer was dried with MgSO$_4$, filtered, and concentrated. The residue was loaded on a short column of silica gel, and eluted with 30-100% hexane/ethyl acetate. The fractions containing the desired acid was concentrated, and dissolved in methanol (10 mL) containing chlorotrimethylsilane (2 mL). After the acidic solution stand overnight at room temperature, it was concentrated and flash chromatographed (silica gel, 10-70% ethyl acetate in hexane) to give 26.4 and 26.5. Both compounds gave MS-ESI (pos.) m/z: 389 (M+H)$^+$.

Scheme 26.3

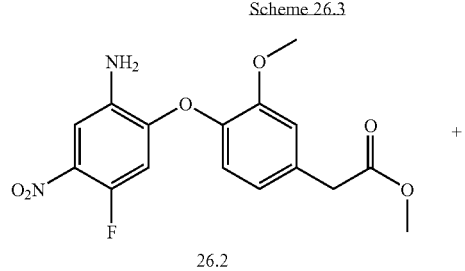

26.2

26.3

Scheme 26.4

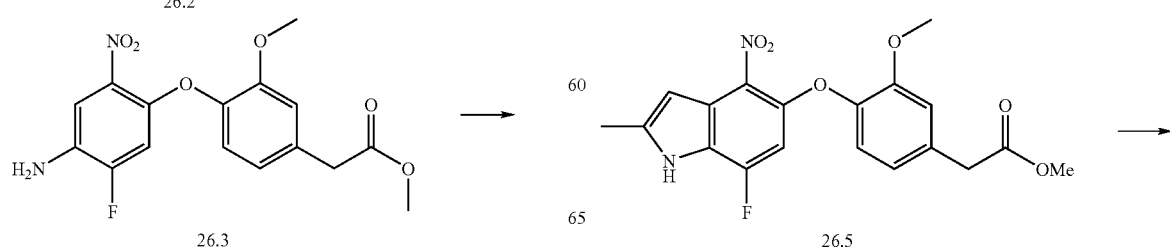

26.5

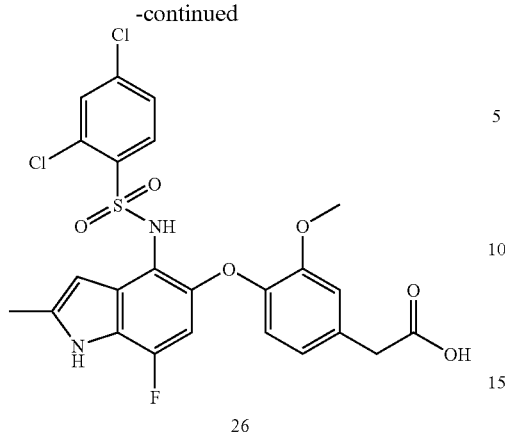

26

2-(4-(4-(2,4-Dichlorophenylsulfonamido)-7-fluoro-2-methyl-1H-indol-5-yloxy)-3-methoxyphenyl)acetic acid (26). To a suspension of 26.5 and palladium on carbon and methanol was hydrogenated under a hydrogen balloon for 2 h. The reaction mixture was then filtered through celite, rinsed with methanol, and concentrated. The residue was dissolved in pyridine and to it was added 2,4-dichlorobenzenesulfonyl chloride, and the reaction was stirred overnight. The reaction was then blown dry, and to it was added THF and aqueous LiOH. After additional 2 h, the reaction was blown by nitrogen to near dryness, and to the residue was added DMSO and TFA. Reverse phase HPLC of the resulting homogeneous solution afforded 27. LC-MS ESI (neg.) m/z: 553.0 (M−H). $^1$H NMR (500 MHz) (CDCl$_3$-CD$_3$OD) δ 7.69 (d, 1 H); 7.10 (m, 2 H); 6.86 (d, 1 H); 6.63 (s, 1 H); 6.58 (dd, 1 H); 6.23 (d, 1 H); 6.18 (d, 1 H); 3.78 (s, 3 H); 3.57 (s, 3 H); 2.48 (s, 3 H).

7.26. Example 27

This example illustrates the preparation of 2-(4-(6-(2,4-dichlorophenylsulfonamido)-2-methylH-pyrazolo[1,5-a]pyridin-5-yloxy)-3-methoxyphenyl)acetic acid (27).

Scheme 27.1

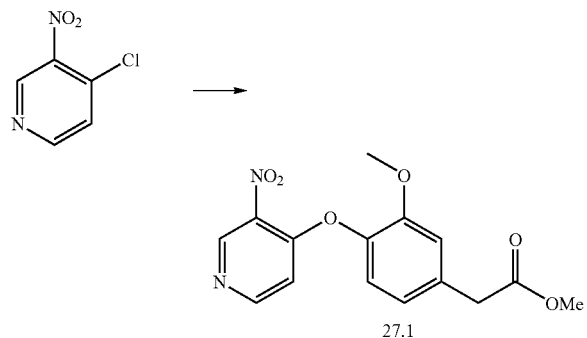

27.1. To a solution of 4-chloro-3-nitropyridine (1.59 g, 10 mmol) and methyl homovanillate (1.96 g, 10 mmol) in DMF (anhydrous, 50 mL) was added cesium carbonate (20 mmol). After reaction was stirred for 12 h at room temperature, the reaction was diluted with DCM (100 mL) filtered through silica gel (about 25 g), rinsed with ethyl acetate and concentrated to afford 27.1. MS-ESI (pos) m/z: 319 (M+H)$^+$.

Scheme 27.2

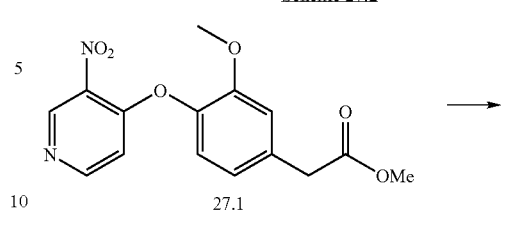

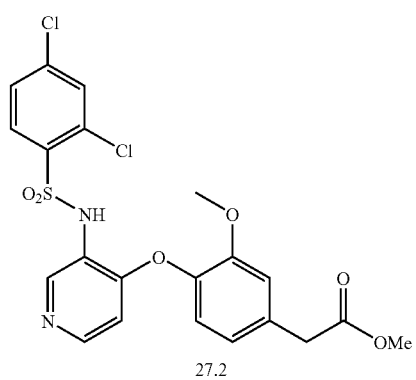

27.2. To a suspension of 27.1 (10 mmol) and palladium on carbon (10%, 200 mg) methanol (25 mL) was hydrogenated under a hydrogen balloon for 2 h. The reaction mixture was then filtered through celite, rinsed with methanol, and concentrated. The residue was dissolved in pyridine (10 mL) and to it was added 2,4-dichlorobenzenesulfonyl chloride (1.5 equiv), and the reaction was stirred overnight at 60° C. Solvent was evaporated, and the residue was loaded to a silica gel column and eluted with (50-100% ethyl acetate in hexane) to give 27.2. MS-ESI (pos.) m/z: 497 (M+H).

Scheme 27.3

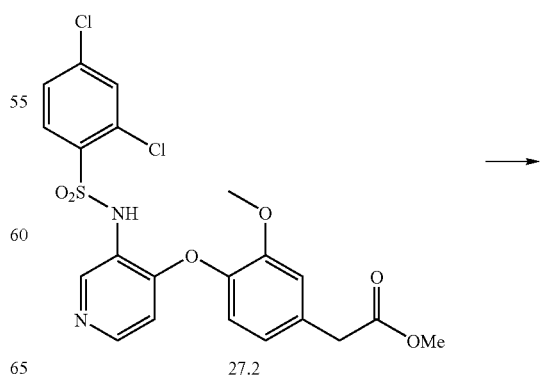

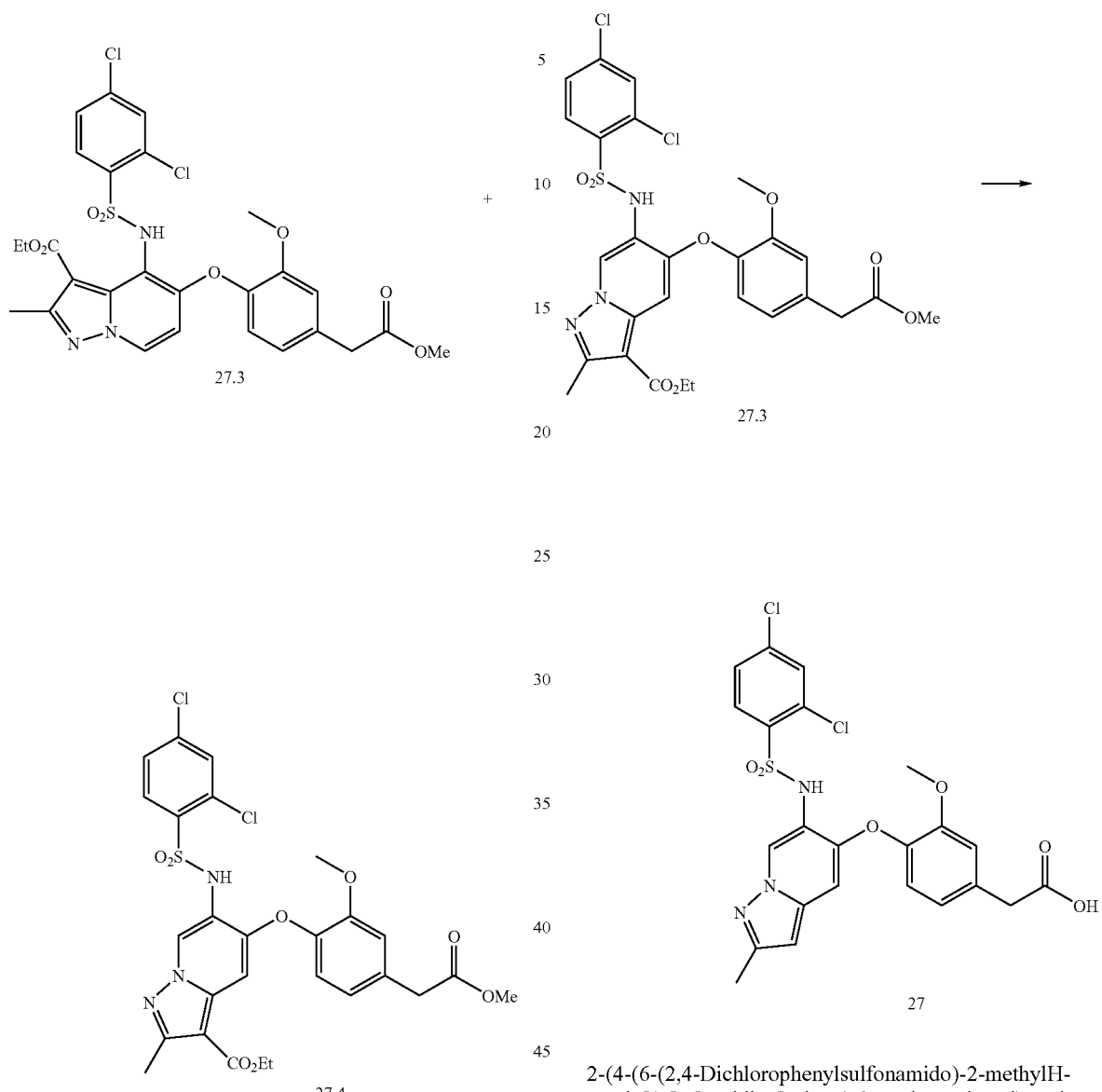

Scheme 27.5

27.3/27.4. To a 0° C. solution of 27.2 (165 mg, 0.30 mmol) in DCM (5 mL) was added O-aminomesitylenesulfate (0.45 mmol) in DCM (2 mL) over 5 min. (slow drops). Reaction was then warmed to room temperature over 3 h. The reaction was concentrated, and to the residue was added ethyl; propiolate (1.0 mmol), potassium carbonate (powdery, anhydrous (2 mmol) and DMF (anhydrous, 2 mmol). The reaction was opened to air and stirred over 20 h. The mixture was then diluted with DCM (5 mL), filtered through silica gel, rinsed with ethyl acetate, and concentrated. The residue was loaded to a silica gel column and eluted with (0-50% ethyl acetate in hexane) to give 27.3 as first fraction and 27.4 as the second fraction. Both products gave the identical MS-ESI (pos.) m/z: 622 (M+H).

2-(4-(6-(2,4-Dichlorophenylsulfonamido)-2-methylH-pyrazolo[1,5-a]pyridin-5-yloxy)-3-methoxyphenyl)acetic acid (27). 27.3 (29 mg) was suspended in 50% sulfuric acid (2 mL). The mixture was heated at 100° C. for 12 h. The reaction was then carefully neutralized to pH 4-5, first with sodium carbonate, then with potassium phosphate. The mixture was extracted with ethyl acetate (30 mL each, 3 times), and the combined extracts were washed with brine, dried over $MgSO_4$, filtered and concentrated. Reverse phase HPLC of the residue afforded 27. LC-MS ESI (neg.) m/z: 536.0 (M−H). $^1$H NMR (400 MHz) ($CDCl_3$-$CD_3OD$) δ 8.79 (s, 1 H); 8.08 (d, 1 H); 7.58 (s, 1 H); 7.48 (d, 1 H); 7.38 (dd, 1 H); 6.98 (d, 1 H); 6.91 (d, 1 H); 6.36 (s, 1 H); 6.01 (s, 1 H); 3.73 (s, 3 H); 3.71 (s, 2 H); 2.43 (s, 3 H).

7.27. Example 28

This example illustrates the preparation of 2-(4-(4-(2,4-dichloro-N-methylphenylsulfonamido)-2-methylH-pyrazolo[1,5-a]pyridin-5-yloxy)-3-methoxyphenyl)acetic acid (28).

Scheme 28.1

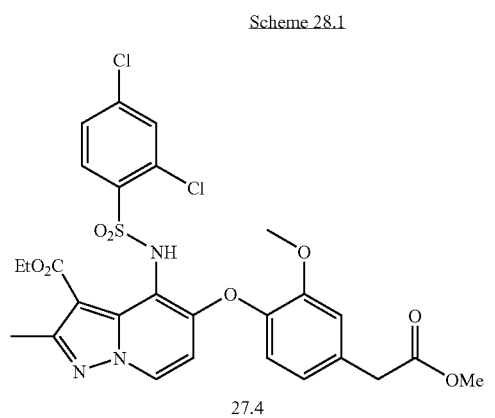

28.1. 27.4 (110 mg) was suspended in 50% sulfuric acid (2 mL). The mixture was heated at 100° C. for 20 h. The reaction was then carefully neutralized to pH 4-5, first with sodium carbonate, then with potassium phosphate. The mixture was extracted with ethyl acetate (30 mL each, 3 times), and the combined extracts were washed with brine, dried over MgSO$_4$, filtered and concentrated. The residue was redissolved in methanol (1 mL) and DCM (3 mL), and treated with TMSCHN$_2$ (2.0M) until yellow color stayed (about 1 mL). The reaction mixture was evaporated and the residue was loaded to a silica gel column and eluted with (50-100% ethyl acetate in hexane) to give 28.1, along with side products. MS-ESI (pos.) m/z: 566 (M+H)$^+$.

Scheme 28.2

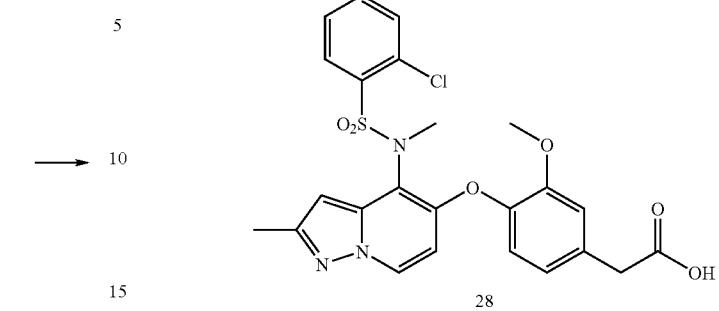

2-(4-(4-(2,4-Dichloro-N-methylphenylsulfonamido)-2-methylH-pyrazolo[1,5-a]pyridin-5-yloxy)-3-methoxyphenyl)acetic acid (28). A solution of 28.1 (8 mg) in THF (1 mL) was treated with aqueous LiOH (1.0M, 0.2 mL). After 5 h at 25° C., most solvent was blown away with nitrogen and to the residue was added DMSO (3 mL) and TFA (0.1 mL). Reverse phase HPLC of the resulting homogeneous solution afforded the 29. LC-MS ESI (neg.) m/z: 550.0 (M–H). $^1$H NMR (400 MHz) (CDCl$_3$-CD$_3$OD) δ 8.06 (d, 1 H); 7.83 (d, 1 H); 7.34 (d, 1 H); 7.18 (dd, 1 H); 6.84 (d, 1 H), 6.76 (dd, 1 H); 6.44 (d, 1 H); 6.35 (s, 1 H); 5.95 (d, 1 H); 3.63 (s, 3 H); 3.54 (s, 2 H); 3.51 (s, 3 H); 2.41 (s, 3 H).

7.28. Example 29

This example illustrates the preparation of 2-(4-(4-(2-chloro-N,4-dimethylphenylsulfonamido)-2-methyl-1H-indol-5-yloxy)-3-methoxyphenyl)acetic acid (29).

Scheme 29.1

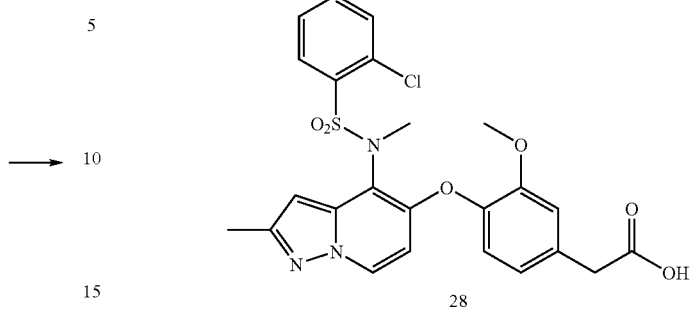

29.1. To a solution of 2-chloro-4-methylaniline (20 mmol) in acetonitrile (160 mL) 0° C. was added sequentially acetic acid (16 mL), concentrated aqueous HCl (8 mL) and NaNO$_2$ (1.66 g in 3 mL H$_2$O). After 15 min, sulfur dioxide was blow into the reaction (just above the surface) for 30 min while the reaction was kept at 0° C. the whole time. A total of 35 g of sulfur dioxide was collected. CuCl$_2$ (3.4 g, 25 mmol) was added to the reaction mixture, and the reaction was gradually warmed to room temperature over 12 h. The reaction mixture was then diluted with ether (200 mL), washed with icy water (30 mL, twice) and brine. The organic layer was dried with MgSO$_4$, filtered, and concentrated. The residue was loaded on column of silica gel, and eluted with 0-20% hexane/ethyl acetate to give 29.1. $^1$H NMR (400 MHz) (CDCl$_3$) δ 8.06 (d, 1 H); 7.35 (s, 1 H); 7.30 (d, 1 H); 2.49 (s, 3 H).

Scheme 29.2

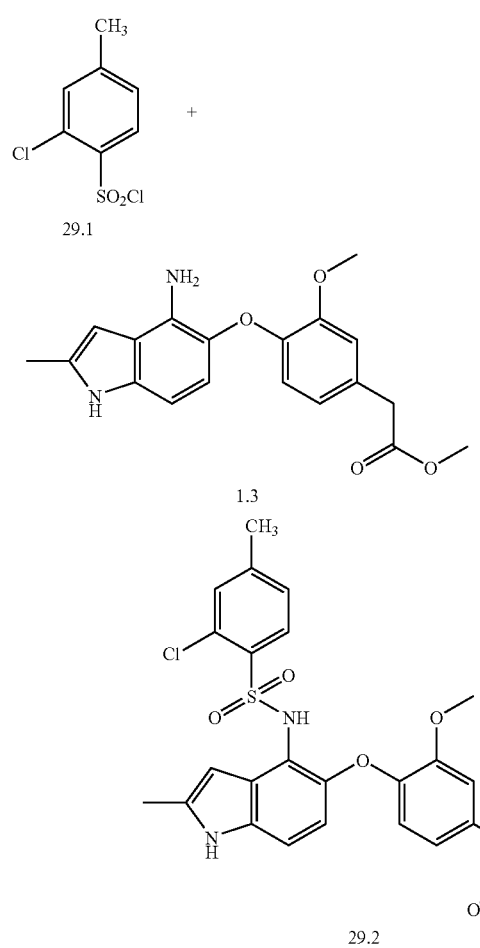

29.2 A solution of 1.3 (32 mg, 0.10 mmol) was dissolved in pyridine (0.5 mL) and to it was added 29.1 (50 mg), and the reaction was stirred overnight. The reaction was then blown dry, and the residue was loaded on column of silica gel, and eluted with 20-100% hexane/ethyl acetate to give 29.2. MS-ESI (pos.) m/z: 529.1 (M+H).

Scheme 29.3

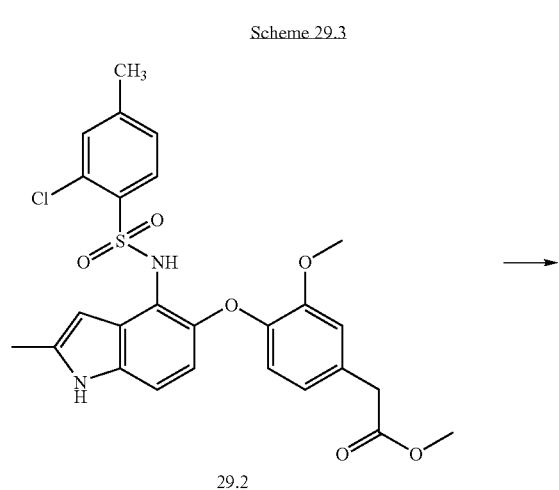

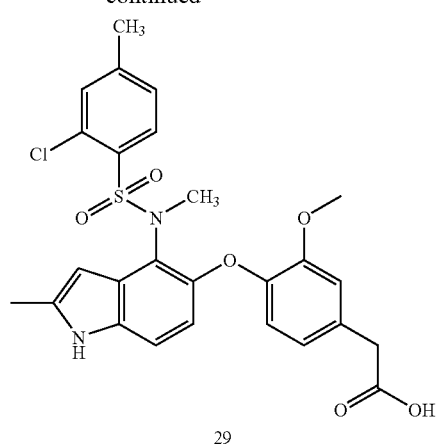

2-(4-(4-(2-Chloro-N,4-dimethylphenylsulfonamido)-2-methyl-1H-indol-5-yloxy)-3-methoxyphenyl)acetic acid (29). To a solution of 29.2 (10 mg) in methanol (0.2 mL) and DCM (1.0 mL) was added TMSCHN$_2$ (2.0M) until yellow color stayed (about 0.1 mL). The reaction mixture was evaporated and the residue was dissolved in THF (1 mL). To the solution was added aqueous LiOH (1.0 M, 0.2 mL). After 5 h at 25° C., most solvent was blown away with nitrogen and to the residue was added DMSO (3 mL) and TFA (0.1 mL). Reverse phase HPLC of the resulting homogeneous solution afforded 29. LC-MS ESI (neg.) m/z: 527.0 (M−H). $^1$H NMR (400 MHz) (dmso-d$_6$) δ 11.00 (s, 1 H); 7.64 (d, J=8.0 Hz, 1 H); 7.36 (s, 1 H), 7.12 (m, 2 H); 6.95 (s, 1 H); 6.69 (d, J=7.6 Hz, 1 H); 6.36 (d, J=8.1 Hz, 1 H); 6.25 (d, 8.6 Hz, 1 H); 6.00 (s, 1 H); 3.67 (s, 3 H); 3.53 (s, 2 H); 3.41 (s, 3 H); 2.36 (s, 3 H); 2.31 (s, 3 H).

7.29. Example 30

This example illustrates the preparation of 2-(3-chloro-4-(6-(4-chlorophenylsulfonamido)-1,3-dioxoisoindolin-5-yloxy)phenyl)acetic acid (30).

Scheme 30.1

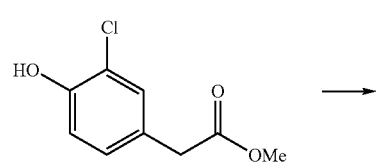

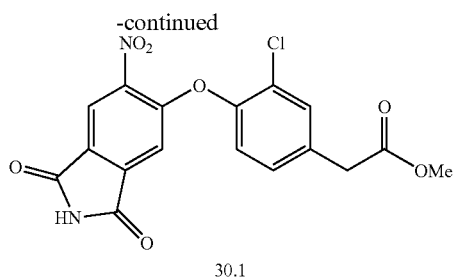

30.1

Methyl 2-(3-chloro-4-(6-nitro-1,3-dioxoisoindolin-5-yloxy)phenyl)acetate (30.1). A mixture of 4-chloro-5-nitrophthalimide (1.05 g, 4.4 mmol), methyl 2-(3-chloro-4-hydroxyphenyl)acetate (821 mg, 4.4 mmol) and potassium carbonate (1.34 g, 9.7 mmol) in 10 mL of DMSO was allowed to stir at 25° C. for 22 h. Upon completion, the mixture was added to 50 mL of water. The resulting mixture was extracted with ethyl acetate (2×30 ml,). The combined extracts were washed with water (2×30 mL) and brine, dried over anhydrous sodium sulfate and concentrated in vacuo. The crude product was purified by chromatography on a silica gel column using 20% EtOAc/hexane as the eluent to give methyl 2-(3-chloro-4-(6-nitro-1,3-dioxoisoindolin-5-yloxy)phenyl) acetate (30.1). MS ESI (pos.) m/e calcd for $(M+H)^+$ 391.0. found 391.0.

Scheme 30.2

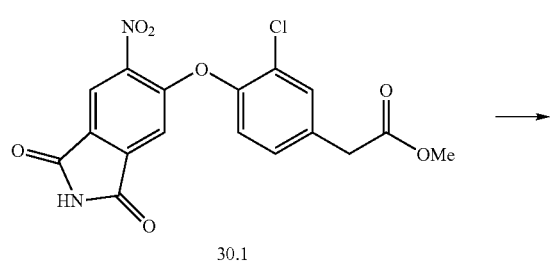

30.1

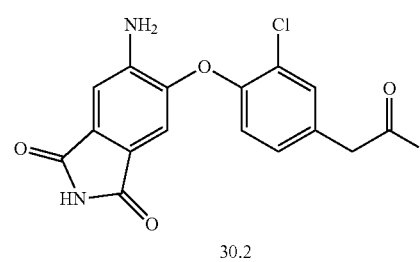

30.2

Methyl 2-(4-(6-amino-1,3-dioxoisoindolin-5-yloxy)-3-chlorophenyl)acetate (30.2). To a solution of 30.1 (162 mg, 0.42 mmol) in 10 mL of EtOAc was added $SnCl_2 \cdot 2H_2O$ (469 mg, 2.1 mmol). The mixture was heated to reflux for 3 h. After cooling to room temperature, the mixture was poured into 20 mL of water. Saturated $NaHCO_3$ was added to adjust the pH value of the mixture to 3. The mixture was filtered through Celite to remove solid precipitates. The filtrate was extracted with EtOAc. The EtOAc extract was washed with brine, dried over $Na_2SO_4$, and evaporated in vacuo to give 30.2. MS ESI (pos.) m/e calcd for $(M+H)^+$ 361.1. found 361.0.

Scheme 30.3

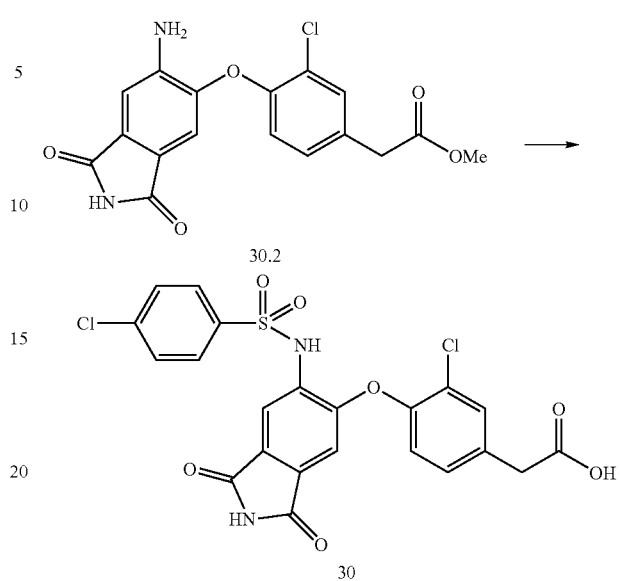

2-(3-Chloro-4-(6-(4-chlorophenylsulfonamido)-1,3-dioxoisoindolin-5-yloxy)phenyl)acetic acid (30). Compound 30.2 (25 mg, 0.07 mmol) and 4-chlorobenzenesulfonyl chloride (30 mg, 0.14 mmol) were stirred in dichloromethane (0.5 mL) with 2,6-lutidine (0.25 mL, 0.21 mmol) at 25° C. for 14 h. The reaction mixture was loaded directly on a silica gel column and purified using 20% EtOAc/hexane as the eluent to give methyl 2-(3-chloro-4-(6-(4-chlorophenylsulfonamido)-1,3-dioxoisoindolin-5-yloxy)phenyl)acetate, and a compound with LC-MS matching a bis-sulfonamide. Both acetates were hydrolyzed in MeOH/THF/water (0.3 mL each) with $LiOH \cdot H_2O$ (6 mg, 0.14 mmol) at 25° C. for 2 h to give the same desired product (30). The reaction mixtures were acidified to pH ~3 and extracted with dichloromethane to give compound 30 as a pale-yellow solid. MS ESI (pos.) m/e calcd for $(M+H_3O)^+$ 539.0. found 539.0. $^1H$ NMR (500 MHz) (DMSO-$d_6$) δ 12.46 (br. s, 1H); 10.42 (s, 1H); 7.79 (d, J=8.3 Hz, 2H); 7.64 (d, J=8.5 Hz, 2H); 7.50 (d, J=1.9 Hz, 1H); 7.24 (dd, J=11.9, 8.3 Hz, 1H); 7.18 (s, 1H); 7.08 (s, 1H); 6.98 (s, 1H); 6.81 (d, J=8.2 Hz, 1H); 3.64 (s, 2H).

7.30. Example 31

Modulation of $CRTH2$, DP and/or one or more other $PGD_2$ receptors by test compounds can be assessed by various in vitro and in vivo assays. Examples of such assays include measuring second messenger (e.g., cAMP, $IP_3$ or $Ca^{2+}$) levels, ion flux, phosphorylation levels, transcription levels, and the like. Recombinant or naturally occurring CRTH2 polypeptides, DP polypeptides and/or other $PGD_2$ receptor peptides can be used and the protein can be isolated, expressed in a cell, expressed in a membrane derived from a cell, expressed in tissue or in an animal. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and/or cytoplasmic domain of a receptor. Gene amplification can also be examined. Furthermore, ligand-binding domains of the protein of interest can be used in vitro in soluble or solid state reactions to assay for ligand binding.

CRTH2-G-protein or another PGD$_2$ receptor-G-protein interactions can also be examined, by, for example, analysis of binding of the G-protein to the receptor or its release from the receptor.

The following protocols exemplify assays in which to test compounds.

7.301. Human CRTH2 Binding Assay

Full-length human CRTH2 cDNA was generated by polymerase chain reaction (PCR) using human genomic DNA as template and subsequently cloned into pcDNA3.1(+) (Invitrogen Corp., Carlsbad, Calif.), generating a CRTH2 expression plasmid pHLT124. The plasmid was transfected into 293 cells, which normally express CRTH2, using LIPOFECTAMINE™ reagents (Invitrogen Corp., Carlsbad, Calif.). G418 (800 mg/mL) was added to the culture 48 h after transfection and cells were maintained under selection for 3 weeks to ensure that all surviving cells stably expressed CRTH2. These cells are labeled as 293(124) hereafter.

$^3$H-PGD$_2$ binding assay was performed using 293(124) cells. In brief, cells were washed and suspended in RPMI containing 0.5% BSA and 20 mM HEPES. Each assay contained 25,000 cells, appropriate amount of test compound when necessary and a mixture of 1 nM $^3$H-PGD$_2$ (Amersham Biosciences, Piscataway, N.J.) and 30 nM of unlabeled PGD$_2$ (Cayman Chemical Co., Ann Arbor, Mich.) in 200 mL final volume. The cell mixture was incubated at room temperature for 2.5 h with shaking and the cells were separated from free $^3$H-PGD$_2$ and transferred onto a filter plate using a cell harvester. Radioactivity bound to the cells was measured on a liquid scintillation counter. Nonspecific binding was determined in the presence of 10 mM of unlabeled PGD$_2$.

Exemplary compounds of the invention displayed IC$_{50}$ values as shown in Table I in the above-described CRTH2 binding assay.

7.30.2. Human DP Binding Assay

Full-length human DP cDNA was generated by PCR using human genomic DNA as a template and subsequently cloned into pcDNA3.1(+) to generate a DP expression plasmid. The plasmid was transfected into 293 cells to generate a line of cells that have stable overexpression of human DP, termed 293(128) cells, essentially as described above for CRTH2. $^3$H-PGD$_2$ binding assays were performed using 293(128) cells as described above for CRTH2 except that each assay contained 350,000 cells, and 2 nM $^3$H-PGD$_2$ and 0 nM unlabeled PGD$_2$.

Exemplary compounds of the invention displayed IC$_{50}$ values as shown in Table I in the above-described DP binding assay.

7.30.3. Cyclic AMP Assays on Human DP Function

Cyclic AMP assays on human DP function are performed using human platelets (AllCells, Berkeley, Calif.) and the 96-well Tropix cAMP ELISA System (Applied Biosystems) following the manufacturer's manual. Briefly, the human platelets rich plasma (PRP) is diluted 1:3 with human plasma and incubated with 1 mM of the phosphodiesterases inhibitor 3-isobutyl-1-methylxanthine (IBMX, Sigma) at 37 C for 20 min, to prevent hydrolysis of cAMP. 20 μl of the above PRP sample is mixed 1:1:1 with the test compound and PGD$_2$ (both prepared in the assay buffer with DMSO concentration <1%) in a 96-well plate. The assay buffer can be GIBCO OPTI-MEM I Reduced Serum medium (Invitrogen). After 20 min incubation at 37° C., 20 μl of lysis buffer from the kit is added to each well of the mixture and the plate then incubated at room temperature for 10 min with moderate shaking and at 37° C. for 10 min. After the cell lysis, 60 μl of the cell lysate together with 30 μl of diluted cAMP-AP conjugate and 60 μl anti-cAMP antibody is then transferred into a kit assay plate and the plate incubated at room temperature for 30 min with

TABLE I

| Example | STRUCTURE | IC$_{50}$ observed in CRTH2 binding assay* | IC$_{50}$ observed in DP binding assay* |
|---|---|---|---|
| 1 | 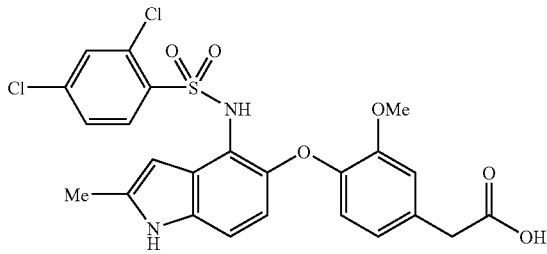 | ++++ | +++++ |
| 30 | 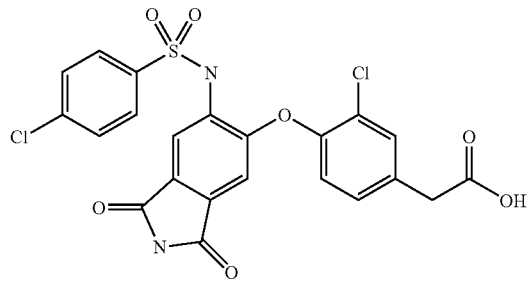 | +++ | ++ |

*Ranges for observed IC50 values are as follows:
+ IC$_{50}$ ≧ 15 μM
++ 15 μM > IC$_{50}$ ≧ 1.0 μM
+++ 1.0 μM > IC$_{50}$ ≧ 0.1 μM
++++ 0.1 μM > IC$_{50}$ ≧ 0.01 μM
+++++ IC$_{50}$ < 0.01 μM shaking. The plate is then washed with wash buffer and incubated with 100 μl per well of substrate/enhancer solution at room temperature for 60 min. Light signal intensity, which is inversely proportional to the cAMP level in each sample, is measured in a luminometer (CLIPR, Dynamic Devices). The final human plasma concentration in the assay described above is about 33%. The assays are also performed using washed platelets (prepared by centrifuging the PRP at 2000 rpm for 15 min and resuspending the platelets in the assay buffer), or in the presence of higher than about 33% of human plasma by also preparing the test compound and/or PGD$_2$ solution in human plasma.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound having formula II or III:

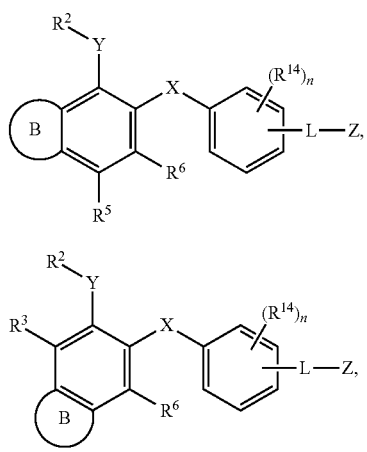

or a pharmaceutically acceptable salt, thereof, wherein
B is a fused 5-membered ring consisting of carbon atoms and 1 heteroatom, wherein the heteroatom is nitrogen; optionally, B is substituted with halogen, $(C_1$-$C_3)$alkyl, halo$(C_1$-$C_3)$alkyl, cyclo$(C_3$-$C_5)$alkyl, amino$(C_1$-$C_3)$alkyl, hydroxy, oxo, —OR', —CONR'R", —N(R")C(O)R', —CO$_2$R', or —CN;
X is —O—;
Y is —S(O)$_k$NR$^{10}$;
Z is —CO$_2$R$^{12}$;
L is $(C_1$-$C_6)$alkylene;
R$^2$ is a substituted or unsubstituted aryl, wherein the substituted aryl is substituted with 1 to 5 substituents independently selected from -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro$(C_1$-$C_4)$alkoxy, or perfluoro$(C_1$-$C_4)$alkyl;

R$^3$, R$^5$ and R$^6$ are independently hydrogen, halogen, $(C_1$-$C_8)$alkyl, fluoro$(C_1$-$C_4)$alkyl, —NR'R", —OR', —NO$_2$, —CN, —C(O)R', —CO$_2$R', —C(O)NR'R", $(C_1$-$C_4)$alkylene-C(O)NR'R", —S(O)$_m$R', —S(O)$_k$NR'R", —OC(O)OR', —OC(O)R', —OC(O)NR'R", —N(R''')C(O)NR'R", —N(R")C(O)R', —N(R")S(O)$_k$R' or —N(R")C(O)OR';

R$^{10}$ is selected from hydrogen or $(C_1$-$C_8)$alkyl;

R$^{12}$ is selected from hydrogen or $(C_1$-$C_6)$alkyl;

each R$^{14}$ is independently halogen, $(C_1$-$C_8)$alkyl, fluoro$(C_1$-$C_4)$alkyl, $(C_2$-$C_5)$alkenyl, —OR', —NR'R", —NO$_2$, —CN, —C(O)R' or aryl;

each R', R" and R''' is independently hydrogen or $(C_1$-$C_6)$alkyl;

subscript k is 2;

subscript m is 0, 1, 2 or 3; and subscript n is 0, 1, 2, 3 or 4.

2. The compound of claim 1, wherein B is aromatic.

3. The compound of claim 1, wherein B is selected from the group consisting of

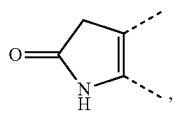 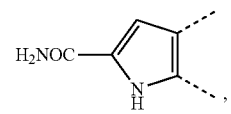

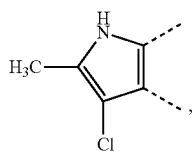 and 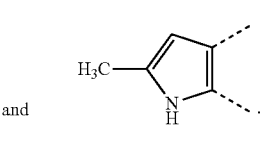.

4. The compound of claim 1, where R$^2$ is a benzene ring.

5. The compound of claim 1, having formula IIa or IIb:

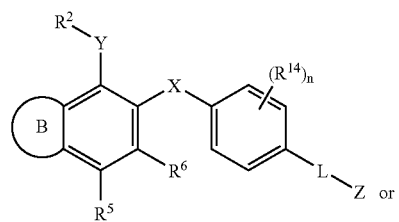

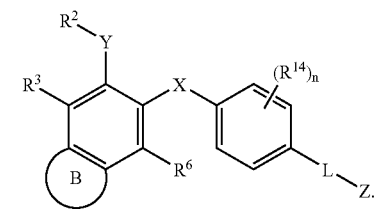

6. The compound of claim 1, wherein subscript n is 0, 1 or 2.

7. The compound of claim 6 selected from the group consisting of:

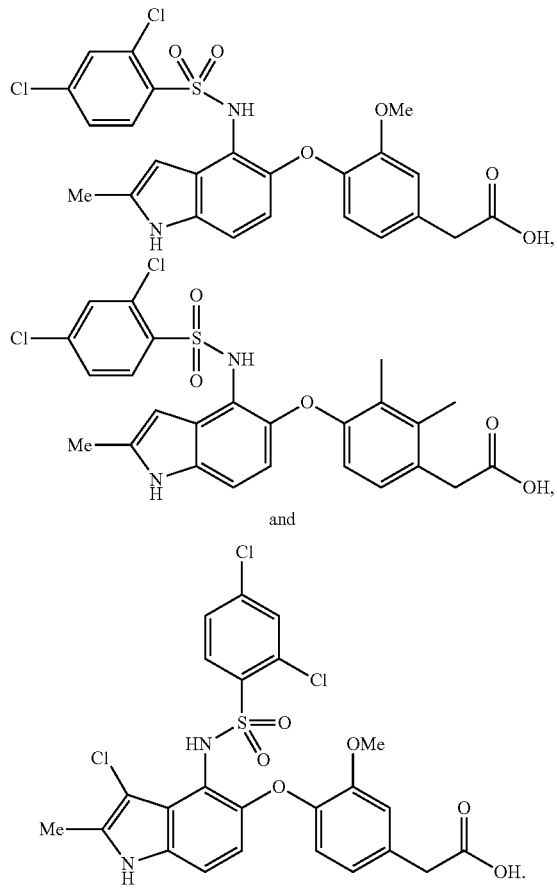

8. A pharmaceutical composition comprising a pharmaceutically acceptable carrier or excipient and a compound of claim 1.

9. A pharmaceutical composition comprising a pharmaceutically acceptable carrier or excipient and a compound of claim 7.

10. The compound of claim 1, wherein $R^2$ is 2,4-dichlorophenyl.

11. The compound of claim 1, wherein $R^2$ is 2-chloro-4-propylphenyl.

12. The compound of claim 1, wherein $R^2$ is 2-chloro-4-(2,2,2-trifluoroethoxy)phenyl.

13. The compound of claim 1, wherein $R^2$ is 2-chloro-4-ethoxyphenyl.

14. The compound of claim 1, wherein $R^2$ is 2,4-dimethylphenyl.

15. The compound of claim 1, wherein $R^2$ is 2-chloro-4-methylphenyl.

16. The compound of claim 1, wherein $R^2$ is 4-chlorophenyl.

17. The compound of claim 1, wherein $R^2$ is 4-tolyl, 2-naphthyl, phenyl, 2,4-dichlorophenyl, 4-methoxyphenyl, 4-trifluoromethoxyphenyl, 2-chlorophenyl, 4-chlorophenyl, 3-chlorophenyl, 2,4-dichloro-5-methylphenyl, 4-n-pentylphenyl, 4-cyanophenyl, 4-n-butoxyphenyl, 2-cyano-3-chlorophenyl, 3-chloro-4-methylphenyl, 2-methoxy-5-bromophenyl, or 2,4-difluorophenyl.

18. The compound of claim 1, wherein Z is —CO$_2$H.

19. The compound of claim 1, wherein Y is —SO$_2$NH—.

* * * * *